US012559487B2

(12) United States Patent
Kamioka et al.

(10) Patent No.: US 12,559,487 B2
(45) Date of Patent: Feb. 24, 2026

(54) CROSSLINKED OPTICALLY ACTIVE SECONDARY AMINE DERIVATIVE

(71) Applicant: Sumitomo Pharma Co., Ltd., Osaka (JP)

(72) Inventors: Seiji Kamioka, Toyonaka (JP); Naoaki Shimada, Takatsuki (JP); Wataru Hirose, Setagaya (JP); Hitoshi Ban, Nishinomiya (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 844 days.

(21) Appl. No.: 17/763,265

(22) PCT Filed: Sep. 25, 2020

(86) PCT No.: PCT/JP2020/036219
§ 371 (c)(1),
(2) Date: Mar. 24, 2022

(87) PCT Pub. No.: WO2021/060453
PCT Pub. Date: Apr. 1, 2021

(65) Prior Publication Data

US 2022/0380365 A1 Dec. 1, 2022

(30) Foreign Application Priority Data

Sep. 27, 2019 (JP) ................................ 2019-176324

(51) Int. Cl.

| | |
|---|---|
| ***C07D 471/04*** | (2006.01) |
| ***A61K 31/439*** | (2006.01) |
| ***A61K 31/4545*** | (2006.01) |
| ***A61K 31/496*** | (2006.01) |
| ***A61K 31/55*** | (2006.01) |
| ***A61K 31/551*** | (2006.01) |
| ***A61K 45/06*** | (2006.01) |
| ***A61P 35/00*** | (2006.01) |
| ***C07D 519/00*** | (2006.01) |

(52) U.S. Cl.
CPC .......... *C07D 471/04* (2013.01); *A61K 31/439* (2013.01); *A61K 31/4545* (2013.01); *A61K 31/496* (2013.01); *A61K 31/55* (2013.01); *A61K 31/551* (2013.01); *A61K 45/06* (2013.01); *A61P 35/00* (2018.01); *C07D 519/00* (2013.01)

(58) Field of Classification Search
CPC .. C07D 471/04; C07D 519/00; A61K 31/439; A61K 31/4545; A61K 31/496; A61K 31/55; A61K 31/551; A61K 45/06; A61P 35/00; A61P 35/02
See application file for complete search history.

(56) References Cited

U.S. PATENT DOCUMENTS

| | | | |
|---|---|---|---|
| 10,683,302 | B2 | 6/2020 | Cacatian et al. |
| 2019/0010167 | A1 | 1/2019 | Claremon et al. |
| 2019/0202830 | A1 | 7/2019 | Cacatian et al. |
| 2019/0211036 | A1 | 7/2019 | Angibaud et al. |
| 2021/0024547 | A1 | 1/2021 | Kamioka et al. |
| 2021/0198283 | A1 | 7/2021 | Kamioka et al. |
| 2021/0338668 | A1 | 11/2021 | Kamioka et al. |

FOREIGN PATENT DOCUMENTS

| | | | | |
|---|---|---|---|---|
| WO | WO 2017/112768 A1 | 6/2017 | | |
| WO | WO 2017/214367 A1 | 12/2017 | | |
| WO | WO 2018/050686 A1 | 3/2018 | | |
| WO | WO-2018053267 A1 * | 3/2018 | | ........... A61K 31/437 |
| WO | WO 2018/106818 A1 | 6/2018 | | |
| WO | WO 2019/189732 A1 | 10/2019 | | |
| WO | WO 2020/032105 A1 | 2/2020 | | |
| WO | WO-2020045334 A1 * | 3/2020 | | ......... A61K 31/4747 |

OTHER PUBLICATIONS

WO 2020045334 A1 (Sumitomo Dainippon Pharma Co Ltd) Mar. 5, 2020, Retrieved from Google Patents (Year: 2020).*
International Search Report issued Nov. 24, 2020, in PCT/JP2020/036219, 3 pages.
International Preliminary Report on Patentability and Written Opinion issued Mar. 15, 2022, in PCT/JP2020/036219, 4 pages.
Look A. T, "Oncogenic Transcription Factors in the Human Acute Leukemias", Science, 278 (5340): 1059-1064 (1997).
Yokoyama A, et al., "The Menin Tumor Suppressor Protein Is an Essential Oncogenic Cofactor for MLL-Associated Leukemogenesis", Cell 123 (2): 207-218 (2005).

(Continued)

*Primary Examiner* — Joseph K Mckane
(74) *Attorney, Agent, or Firm* — Oblon, McClelland, Maier & Neustadt, L.L.P.

(57) ABSTRACT

The present invention relates to the compound of formula (1a) wherein p is 1 or 2, $R^1$-$R^4$ are hydrogen atom or the like, Ring A is cycloalkylene or the like, L is single bond or the like, and R is methyl or the like, or a pharmaceutically acceptable salt thereof, which has an anticancer effect by inhibiting the binding between a MLL fusion protein that is fused with AF4, AF9, or the like, which is a representative fusion partner gene causing MLL leukemia, and menin.

(1a)

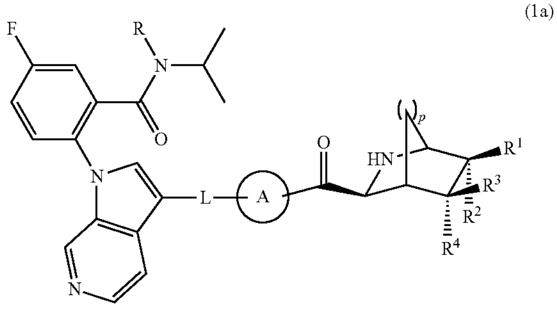

40 Claims, No Drawings

(56) References Cited

OTHER PUBLICATIONS

Yokoyama A, et al., "Menin Critically Links MLL Proteins with LEDGF on Cancer-Associated Target Genes", Cancer Cell. 14(1): 36-46 (2008).

Malik, R. et al., "Targeting the MLL complex in castration-resistant prostate cancer", Nature Medicine. 21(4):344-352 (2015).

Imachi, H. et al., "Menin, a product of the MENI gene, binds to estrogen receptor to enhance its activity in breast cancer cells: possibility of a novel predictive factor for tamoxifen resistance", Breast Cancer Res Treat. 122(2):395-407 (2010).

Svoboda, L. K et al., "Tumorigenicity of Ewing sarcoma is critically dependent on the trithorax proteins MLL1 and menin", Oncotarget. 8(1):458-471 (2017).

* cited by examiner

CROSSLINKED OPTICALLY ACTIVE SECONDARY AMINE DERIVATIVE

This application is a National Stage application of PCT/JP2020/036219, filed Sep. 25, 2020, the entire contents of which is incorporated herein by reference, which application claims priority to Japanese application JP2019-176324, filed Sep. 27, 2019, the entire contents of which is incorporated herein by reference.

TECHNICAL FIELD

The present invention relates to a crosslinked optically-active secondary amine derivative useful as a medicament, or a pharmaceutically acceptable salt thereof, and a pharmaceutical composition comprising it, or a medicament comprising the composition for treating or preventing conditions related to the binding between menin and MLL.

BACKGROUND OF THE INVENTION

MLL leukemia is a disease that accounts for about 6 to 7% of acute myeloid leukemia (AML) and acute lymphoblastic leukemia (ALL), and about 1100 people are newly diagnosed with MLL leukemia each year in America. It has been reported that major fusion partner genes that cause MLL leukemia are likely to be AF9, ELL, ENL, AF10, and AF6 in AML, and AF4, ENL, and AF9 in ALL (Non-patent literature 1).

It is inferred that a MLL fusion protein fused with a fusion partner gene can cause unrestrained proliferation of undifferentiated hematopoietic cells to lead to leukemia (Non-patent literature 2). It is reported that a MLL fusion protein firstly binds to menin to form a complex. Accordingly, it is expected that canceration caused by a MLL fusion protein can be prevented by inhibiting the first binding between a MLL fusion protein and menin (Non-patent literature 3).

It is reported that MLL acts as an activation cofactor of an androgen signal in prostate cancer. Accordingly, it is expected that a small molecular inhibitor which is targeted to inhibiting the binding between menin and a MLL fusion protein is useful as a medicament for treating the cancer (Non-patent literature 4).

It is reported that menin acts as an activation cofactor of an estrogen signal in breast cancer. Accordingly, it is expected that a small molecular inhibitor which is targeted to inhibiting the binding between menin and a MLL fusion protein is useful as a medicament of the cancer (Non-patent literature 5).

It is reported that menin or MLL is important for tumor progression in Ewing's sarcoma, liver cancer, and p53 gain-of-function mutation cancer, and it is expected that a small molecular inhibitor which is targeted to inhibiting the binding between menin and a MLL fusion protein is useful as a medicament of the cancers (Non-patent literature 6).

Patent literatures 1 to 3 disclose small molecular inhibitors which are targeted to inhibiting the binding between menin and a MLL fusion protein. The present compound of the following formula (1) which is a crosslinked optically active secondary amine derivative, however, is not disclosed or suggested in them.

PRIOR ART

Patent Reference

[Patent Literature 1] WO 2017/112768
[Patent Literature 2] WO 2017/214367
[Patent Literature 3] WO 2018/050686

Non-Patent Reference

[Non-patent Literature 1] Look A. T, Science, 278 (5340): 1059-1064 (1997)
[Non-patent Literature 2] Yokoyama A, et al., Cell 123 (2): 207-218 (2005)
[Non-patent Literature 3] Yokoyama A, et al., Cancer Cell. 14(1): 34-46 (2008)
[Non-patent Literature 4] Malik, R. et al., Nature Medicine. 21(4):344-352 (2015)
[Non-patent Literature 5] Imachi, H et al., Breast Cancer Res Treat. 122(2):395-407 (2010)
[Non-patent Literature 6] Svoboda, M. K. et al., Oncotarget. 8(1):458-471 (2017)

SUMMARY OF INVENTION

Technical Problem

The purpose of the present invention may be to provide a compound which has an antitumor effect by inhibiting the binding between a MLL (mixed lineage leukemia) fusion protein that is fused with AF4, AF9, or the like, which is a representative fusion partner gene causing MLL leukemia, and menin. More preferably, the purpose of the present invention may be to provide a compound which has an antitumor effect by inhibiting the binding between menin and a MLL fusion protein, and which is expected to have high safety by having a gap between the concentration at which the compound can inhibit cell proliferation and the concentration at which the compound can inhibit hERG current. In other words, the purpose of the present invention is to provide an antitumor medicament with high therapeutic effect.

Solution to Problem

The present inventors have extensively studied to reach the above purpose, and then have found that a compound of the following formula (1) or a pharmaceutically acceptable salt thereof (hereinafter, it may be referred to as "the present compound") has an excellent antitumor effect through a potent inhibitory effect on the binding between menin and a MLL fusion protein.

Accordingly, the present invention is described as follows:

(Item 1)

A compound of formula (1):

(1)

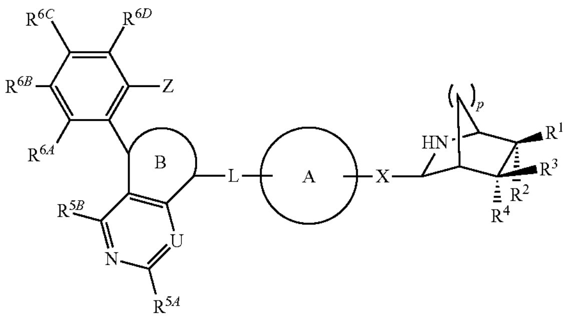

or a pharmaceutically acceptable salt thereof, wherein p is 1 or 2;

$R^1$, $R^2$, $R^3$, and $R^4$ are each independently hydrogen atom, halogen, cyano, nitro, carboxyl, sulfonic acid, —$OR^7$, —$SR^7$, —$COR^8$, —$CO_2R^8$, —$CONR^9R^{10}$, —$SO_2R^8$, —$SO_2NR^9R^{10}$, —$OCOR^8$, —$OCO_2R^8$, —$OCONR^9R^{10}$, —$NR^9R^{10}$, —$NR^{11}COR^8$, —$NR^{11}CO_2R^8$, —$NR^{11}CONR^9R^{10}$, —$NR^{11}SO_2R^8$, —$NR^{11}SO_2NR^9R^{10}$, or -M-Q; $R^1$ or and $R^2$ and/or $R^3$ and $R^4$ may be combined together to form each independently =O, =$CR^{12A}R^{13A}$, =N—$NR^{12B}R^{13B}$, or =N—$OR^{12B}$;

M is, each independently if there are plural, optionally-substituted $C_{1-6}$ alkylene, optionally-substituted $C_{2-6}$ alkenylene, optionally-substituted $C_{2-6}$ alkynylene, optionally-substituted $C_{3-10}$ cycloalkylene, optionally-substituted 3- to 10-membered saturated heterocyclyl, optionally-substituted $C_{6-10}$ arylene, or optionally-substituted 5- to 12-membered heteroarylene;

Q is, each independently if there are plural, hydrogen atom, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^7$ is, each independently if there are plural, hydrogen atom, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^8$ is, each independently if there are plural, $C_{1-6}$ alkyl;

$R^9R^{10}$, and $R^{11}$ are each independently hydrogen atom or $C_{1-6}$ alkyl, and if there are plural $R^9$, $R^{10}$, or $R^{11}$, each $R^9$, $R^{10}$, or $R^{11}$ may be the same or different, or when $R^9$ and $R^{10}$ are both $C_{1-6}$ alkyl, they may be combined with the nitrogen atom to which they are each attached to form 3- to 8-membered nitrogen-containing saturated heterocycle;

$R^{12A}$ and $R^{13A}$ are each independently hydrogen atom, halogen, cyano, nitro, carboxyl, sulfonic acid, —$COR^{14}$, —$CO_2R^{14}$, —$CONR^{15}R^{16}$, —$SO_2R^{14}$, —$SO_2NR^{15}R^{16}$, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{12A}$ or $R^{13A}$, each $R^{12A}$ or $R^{13A}$ may be the same or different, or when $R^{12A}$ and $R^{13A}$ are both optionally-substituted $C_{1-6}$ alkyl, they may be combined with the carbon atom to which they are attached to form 3- to 8-membered saturated carbocycle;

$R^{12B}$ and $R^{13B}$ are each independently hydrogen atom, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{12B}$ or $R^{13B}$, each $R^{12B}$ or $R^{13B}$ may be the same or different, or when $R^{12B}$ and $R^{13B}$ are both optionally-substituted $C_{1-6}$ alkyl, they may be combined with the nitrogen atom to which they are attached to form 3- to 8-membered nitrogen-containing saturated heterocycle;

$R^{14}$ is, each independently if there are plural, $C_{1-6}$ alkyl;

$R^{15}$ and $R^{16}$ are each independently hydrogen atom or $C_{1-6}$ alkyl, and if there are plural $R^{15}$ or $R^{16}$, each $R^{15}$ or $R^{16}$ may be the same or different, or when $R^{15}$ and $R^{16}$ are both $C_{1-6}$ alkyl, they may be combined with the nitrogen atom to which they are each attached to form 3- to 8-membered nitrogen-containing saturated heterocycle;

X is —C(O)—, —NHC(O)—, —C(O)—NH—, or optionally-substituted $C_{1-6}$ alkylene;

Ring A is optionally-substituted $C_{3-10}$ cycloalkylene, optionally-substituted 3- to 10-membered saturated heterocyclyl, optionally-substituted $C_{6-10}$ arylene, or optionally-substituted 5- to 12-membered heteroarylene; L is single bond or optionally-substituted $C_{1-6}$ alkylene;

$R^{5A}$, $R^{5B}$, $R^{6A}$, $R^{6B}$, $R^{6C}$, and $R^{6D}$ are each independently hydrogen atom, halogen, cyano, nitro, carboxyl, sulfonic acid, —$OR^{17}$, —$SR^{17}$, —$COR^{18}$, —$CO_2R^{18}R^{20}$, —$CONR^{19}R^{20}$, —$SO_2R^{18}$, —$SO_2NR^{19}R^{20}$, —$OCOR^{18}$, —$OCO_2R^{18}$, —$OCONR^{19}R^{20}$, —$NR^{21}COR^{18}$, —$NR^{21}CO_2R^{18}$, —$NR^{21}CONR^{19}R^{20}$, —$NR^{21}SO_2R^{18}$, —$NR^{21}SO_2NR^{19}R^{20}$, optionally-substituted $C_{1-6}$ alkyl, optionally-substituted $C_{2-6}$ alkenyl, or optionally-substituted $C_{2-6}$ alkynyl;

$R^{17}$, $R^{19}$, $R^{20}$, and $R^{21}$ are each independently hydrogen atom or $C_{1-6}$ alkyl, and if there are plural $R^{17}$, $R^{19}$, $R^{20}$, or $R^{21}$, each $R^{17}$, $R^{19}$, $R^{20}$, or $R^{21}$ may be the same or different, or when $R^{19}$ and $R^{20}$ are both $C_{1-6}$ alkyl, they may be combined with the nitrogen atom to which they are each attached to form 3- to 8-membered nitrogen-containing saturated heterocycle;

$R^{18}$ is, each independently if there are plural, $C_{1-6}$ alkyl;

U is $CR^{22}$ or nitrogen atom;

$R^{22}$ is hydrogen atom, halogen atom, $C_{1-3}$ alkyl (which may be substituted with 1 to 5 the same or different substituents selected from fluorine atom, —$OR^{23}$ and —$NR^{23}R^{24}$), —$CO_2R^{25}$, —$CONR^{26}R^{27}$, or cyano;

$R^{23}$ and $R^{24}$ are each independently hydrogen atom or $C_{1-6}$ alkyl, and if there are plural $R^{23}$ or $R^{24}$, each $R^{23}$ or $R^{24}$ may be the same or different, or when $R^{23}$ and $R^{24}$ are both $C_{1-6}$ alkyl, they may be combined with the nitrogen atom to which they are attached to form 3- to 8-membered nitrogen-containing saturated heterocycle;

$R^{25}$ is $C_{1-6}$ alkyl;

$R^{26}$ and $R^{27}$ are each independently hydrogen atom or $C_{1-6}$ alkyl, or when $R^{26}$ and $R^{27}$ are both $C_{1-6}$ alkyl, they may be combined with the nitrogen atom to which they are attached to form 3- to 8-membered nitrogen-containing saturated heterocycle;

Ring B is (B-1), (B-2), (B-3), (B-4), or (B-5):

(B-1)

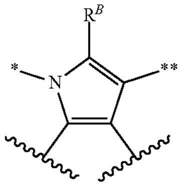

(B-2)

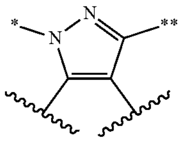

-continued (B-3)

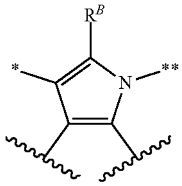

(B-4)

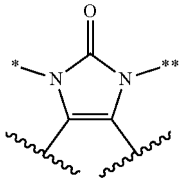

(B-5)

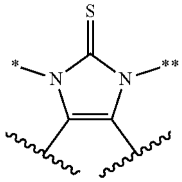

wherein * is a bonding site to the benzene ring, and ** is a bonding site to L;

$R^B$ is hydrogen atom, halogen, cyano, hydroxy, optionally-substituted $C_{1-4}$ alkyl, optionally-substituted $C_{1-4}$ alkoxy, amino, optionally-substituted $C_{1-4}$ alkylamino, or optionally-substituted $C_{2-8}$ dialkylamino;

Z is hydrogen atom, halogen, cyano, nitro, carboxyl, sulfonic acid, $—OR^{30}$, $—SR^{30}$, $—COR^{31}$, $—CO_2R^{31}$, $—CONR^{32}R^{33}$, $—SO_2R^{31}$, $—SO_2NR^{32}R^{33}$, $—OCOR^{31}$, $—OCO_2R^{31}$, $—OCONR^{32}R^{33}$, $—NR^{32}R^{33}$, $—NR^{34}COR^{31}$, $—NR^{34}CO_2R^{31}$, $—NR^{34}CONR^{32}R^{33}$, $—NR^{34}SO_2R^{31}$, $—NR^{34}SO_2NR^{32}R^{33}$, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl;

$R^{30}$, $R^{32}$, $R^{33}$, and $R^{34}$ are each independently hydrogen atom, $C_{1-6}$ alkyl (which may be substituted with 1 to 5 the same or different substituents selected from the group consisting of fluorine atom, chlorine atom, bromine atom and hydroxy), or $C_{3-10}$ cycloalkyl, or when $R^{32}$ and $R^{33}$ are both $C_{1-6}$ alkyl, they may be combined with the nitrogen atom to which they are attached to form 3- to 8-membered nitrogen-containing saturated heterocycle; and $R^{31}$ is $C_{1-6}$ alkyl optionally-substituted with 1 to 5 the same or different substituents selected from the group consisting of fluorine atom, chlorine atom, bromine atom, and hydroxy.

(Item 2)

The compound of Item 1 or a pharmaceutically acceptable salt thereof, wherein $R^1$, $R^2$, $R^3$, and $R^4$ are each independently hydrogen atom, halogen, $—OR^7$, or -M-Q; or $R^1$ and $R^2$ and/or $R^3$ and $R^4$ may be combined together to form each independently =O or $=CR^{12A}R^{13A}$; and $R^{12A}$ and $R^{13A}$ are each independently hydrogen atom, halogen, cyano, optionally-substituted $C_{1-6}$ alkyl, optionally-substituted $C_{2-6}$ alkenyl, optionally-substituted $C_{2-6}$ alkynyl, optionally-substituted $C_{3-10}$ cycloalkyl, optionally-substituted 3- to 10-membered saturated heterocyclyl, optionally-substituted $C_{6-10}$ aryl, or optionally-substituted 5- to 12-membered heteroaryl, and if there are plural $R^{12A}$ or $R^{13A}$, each $R^{12A}$ or $R^{13A}$ may be the same or different, or when $R^{12A}$ and $R^{13A}$ are both optionally-substituted $C_{1-6}$ alkyl, they may be combined with the carbon atom to which they are attached to form 3- to 8-membered saturated carbocycle.

(Item 3)

The compound of Item 1 or 2 or a pharmaceutically acceptable salt thereof, wherein the optionally-substituted $C_{1-6}$ alkylene, the optionally-substituted $C_{2-6}$ alkynylene, the optionally-substituted $C_{2-6}$ alkynylene, the optionally-substituted $C_{3-10}$ cycloalkylene, the optionally-substituted 3- to 10-membered saturated heterocyclyl, the optionally-substituted $C_{6-10}$ arylene, the optionally-substituted 5- to 12-membered heteroarylene, the optionally-substituted $C_{1-4}$ alkyl, the optionally-substituted $C_{1-6}$ alkyl, the optionally-substituted $C_{2-6}$ alkenyl, the optionally-substituted $C_{2-6}$ alkynyl, the optionally-substituted $C_{1-4}$ alkoxy, optionally-substituted alkylamino, the optionally-substituted $C_{2-8}$ dialkylamino, the optionally-substituted $C_{3-10}$ cycloalkyl, the optionally-substituted $C_{6-10}$ aryl, and the optionally-substituted 5- to 12-membered heteroaryl in M, Q, X, Ring A, L, Z, $R^{5A}$, $R^{5B}$, $R^{6A}$, $R^{6C}$, $R^{6D}$, $R^7$, $R^{12A}$, $R^{12B}$, $R^{13A}R^{13B}$, and $R^B$ may be independently substituted with 1 to 5 the same or different substituents selected from the group consisting of (1) halogen,
(2) hydroxy,
(3) $C_{6-10}$ aryl,
(4) 5- to 12-membered heteroaryl,
(5) $C_{1-6}$ alkyl,
(6) $C_{2-6}$ alkenyl,
(7) $C_{2-6}$ alkynyl,
(8) $C_{1-6}$ alkoxy,
(9) $C_{3-10}$ cycloalkyl,
(10) 3- to 10-membered saturated heterocyclyl,
(11) carboxyl,
(12) $—COR^{35A}$,
(13) $—CO_2R^{35A}$,
(14) $—CONR^{36A}R^{37A}$,
(15) $—NR^{36A}R^{37A}$,
(16) $—NR^{36A}COR^{35A}$,
(17) $—NR^{36A}SO_2R^{35A}$,
(18) $—SO_2R^{35A}$,
(19) $—SO_2NR^{36A}R^{37A}$,
(20) sulfonic acid,
(21) phosphoric acid,
(22) cyano, and
(23) nitro wherein the said (3) $C_{6-10}$ aryl, (4) 5- to 12-membered heteroaryl, (5) $C_{1-6}$ alkyl, (6) $C_{2-6}$ alkenyl, (7) $C_{2-6}$ alkynyl, (8) $C_{1-6}$ alkoxy, (9) $C_{2-10}$ cycloalkyl, and (10) 3- to 10-membered saturated heterocyclyl may be independently substituted with 1 to 5 the same or different substituents selected from the group consisting of (a) halogen,
(b) hydroxy,
(c) $C_{6-10}$ aryl,
(d) 5- to 10-membered heteroaryl,
(e) $C_{1-6}$ alkyl,
(f) $C_{2-6}$ alkenyl, (g) $C_{2-6}$ alkynyl,
(h) $C_{1-6}$ alkoxy,
(i) $C_{3-10}$ cycloalkyl,
(j) 3- to 10-membered saturated heterocyclyl,
(k) carboxyl,
(l) —$COR^{5B}$,
(m) —$CO_2R^{35B}$,
(n) —$CONR^{36B}R^{37B}$,
(o) —$NR^{36B}R^{37B}$,
(p) —$NR^{36B}COR^{35B}$,
(q) —$NR^{36B}SO_2R^{35B}$,
(r) —$SO_2R^{35B}$,
(s) —$SO_2NR^{36B}R^{37B}$,
(t) sulfonic acid,
(u) phosphoric acid,
(v) cyano, and
(w) nitro;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 8-membered nitrogen-containing saturated heterocycle;

$R^{35B}$ is, each independently if there are plural, $C_{1-6}$ alkyl; and $R^{36B}$ and $R^{37B}$ are each independently hydrogen atom or $C_{1-6}$ alkyl, and if there are plural $R^{36B}$ or $R^{37B}$, each $R^{36B}$ or $R^{37B}$ may be the same or different, or when $R^{36B}$ and $R^{37B}$ are both $C_{1-6}$ alkyl, they may be combined with the nitrogen atom to which they are attached to form 3- to 8-membered nitrogen-containing saturated heterocycle.

(Item 4)

The compound of any one of Items 1 to 3 or a pharmaceutically acceptable salt thereof, wherein the optionally-substituted $C_{1-6}$ alkylene, the optionally-substituted $C_{2-6}$ alkenylene, the optionally-substituted $C_{2-6}$ alkynylene, the optionally-substituted $C_{3-10}$ cycloalkylene, the optionally-substituted 3- to 10-membered saturated heterocyclyl, the optionally-substituted $C_{6-10}$ arylene, the optionally-substituted 5- to 12-membered heteroarylene, the optionally-substituted $C_{1-4}$ alkyl, the optionally-substituted $C_{1-6}$ alkyl, the optionally-substituted $C_{2-6}$ alkenyl, the optionally-substituted $C_{2-6}$ alkynyl, the optionally-substituted $C_{1-4}$ alkoxy, the optionally-substituted $C_{1-4}$ alkylamino, the optionally-substituted $C_{2-8}$ dialkylamino, the optionally-substituted $C_{3-10}$ cycloalkyl, the optionally-substituted $C_{6-10}$ aryl, and the optionally-substituted 5- to 12-membered heteroaryl in M, Q, X, Ring A, L, Z, $R^{5A}$, $R^{5B}$, $R^{6A}$, $R^{6B}$, $R^{6C}$, $R^{6D}$, $R^7$, $R^{12A}$, $R^{12B}$, $R^{13A}$, $R^{13B}$, and $R^B$ may be independently substituted with 1 to 5 the same or different substituents selected from the group consisting of (1) halogen,
(2) hydroxy,
(3) phenyl,
(4) 5- to 6-membered heteroaryl,
(5) $C_{1-6}$ alkyl optionally-substituted with 1 to 3 hydroxy,
(6) $C_{2-6}$ alkynyl,
(7) $C_{1-6}$ alkoxy,
(8) $C_{3-7}$ cycloalkyl,
(9) 3- to 7-membered saturated heterocyclyl,
(10) —$COR^{35A}$,
(11) —$CO_2R^{35A}$,
(12) —$CONR^{36A}R^{37A}$,
(13) —$NR^{36A}R^{37A}$,
(14) —$NR^{36A}COR^{35A}$,
(15) —$NR^{36A}SO_2R^{35A}$,
(16) —$SO_2R^{35A}$,
(17) —$SO_2NR^{36A}R^{37A}$,
(18) cyano, and
(19) nitro;

$R^{35A}$ is, each independently if there are plural, alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 5)

The compound of any one of Items 1 to 4 or a pharmaceutically acceptable salt thereof, wherein X is —C(O)—.

(Item 6)

The compound of any one of Items 1 to 5 or a pharmaceutically acceptable salt thereof, wherein Ring A is (A-1), (A-2), (A-3), or (A-4):

(A-1)

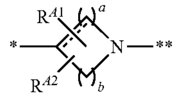

(A-2)

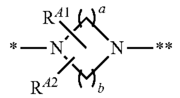

(A-3)

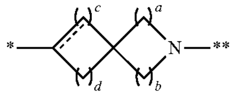

(A-4)

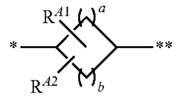

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene; and a, b, c, and d are independently 1, 2, or 3.

(Item 7)

The compound of any one of Items 1 to 6 or a pharmaceutically acceptable salt thereof, wherein Ring B is (B-1).

(Item 8)

The compound of any one of Items 1 to 7 or a pharmaceutically acceptable salt thereof, wherein L is single bond or methylene.

(Item 9)

The compound of any one of Items 1 to 8 or a pharmaceutically acceptable salt thereof, wherein $R^{5A}$, $R^{5B}$, $R^{6A}$, $R^{6B}$, and $R^{6D}$ are hydrogen atom, and $R^{6C}$ is fluorine atom.

(Item 10)

The compound of any one of Items 1 to 9 or a pharmaceutically acceptable salt thereof, wherein U is CH or nitrogen atom.

(Item 11)

The compound of any one of Items 1 to 10 or a pharmaceutically acceptable salt thereof, wherein U is CH.

(Item 12)

The compound of any one of Items 1 to 11 or a pharmaceutically acceptable salt thereof, wherein Z is —$CONR^{32}R^{33}$, 3- to 6-membered saturated heterocyclyl (which may be saturated with 1 to 3 the same or different substituents selected from $C_{1-3}$ alkyl and $C_{3-6}$ cycloalkyl), phenyl (which may be substituted with 1 to 3 the same or different substituents selected from cyano, $C_{1-3}$ alkyl, and $C_{3-6}$ cycloalkyl, wherein the alkyl or the cycloalkyl may be substituted with 1 to 3 hydroxy), or 5- to 6-membered heteroaryl optionally-substituted with 1 to 3 $C_{1-3}$ alkyl; and $R^{32}$ and $R^{33}$ are each independently hydrogen atom or $C_{1-3}$ alkyl, or when $R^{32}$ and $R^{33}$ are both $C_{1-6}$ alkyl, they may be combined with the nitrogen atom to which they are attached to form 3- to 6-membered nitrogen-containing saturated heterocycle.

(Item 13)

The compound of any one of Items 1 to 12 or a pharmaceutically acceptable salt thereof, wherein Z is (Z-1), (Z-2), (Z-3), (Z-4), or (Z-5):

(Z-1)

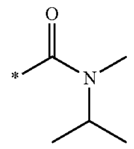

(Z-2)

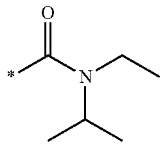

(Z-3)

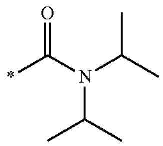

(Z-4)

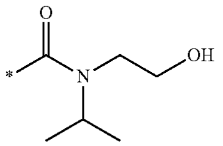

(Z-5)

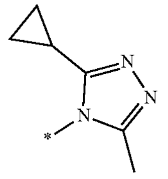

wherein is a bonding site to the benzene ring.

(Item 14)

The compound of Item 13 or a pharmaceutically acceptable salt thereof, wherein Z is (Z-1) or (Z-3).

(Item 15)

The compound of any one of Items 1 to 14 or a pharmaceutically acceptable salt thereof, wherein M is, each independently if there are plural, $C_{1-6}$ alkylene (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkenylene, the alkynylene, the cycloalkylene, the saturated heterocyclyl, the arylene, and the heteroarylene may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$CONR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

Q is, each independently if there are plural, hydrogen atom, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl (which may be substituted with 1 to 5 the same or different substituents selected from the group consisting of fluorine atom, chlorine atom, bromine atom, hydroxy, phenyl, 5- to 6-membered heteroaryl, $C_{2-4}$ alkynyl, $C_{3-7}$ cycloalkyl, 3- to 7-membered saturated heterocyclyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{12A}$ and $R^{13A}$ are each independently hydrogen atom, halogen, cyano, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2R^{36A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 8-membered nitrogen-containing saturated heterocycle.

(Item 16)

The compound of Item 1 of formula (Ia):

(1a)

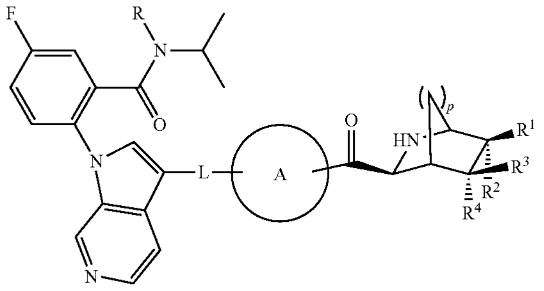

or a pharmaceutically acceptable salt thereof, wherein p is 1 or 2;

$R^1$, $R^2$, $R^3$, and $R^4$ are each independently hydrogen atom, halogen, —$OR^7$, or -M-Q; or $R^1$ and $R^2$ and/or $R^3$ and $R^4$ may be combined together to form each independently =O or =$CR^{12A}R^{13A}$;

M is, each independently if there are plural, $C_{1-6}$ alkylene (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkenylene, the alkynylene, the cycloalkylene, the saturated heterocyclyl, the arylene, and the heteroarylene may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

Q is, each independently if there are plural, hydrogen atom, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl (which may be substituted with 1 to 5 the same or different substituents selected from the group consisting of fluorine atom, chlorine atom, bromine atom, hydroxy, phenyl, 5- to 6-membered heteroaryl, $C_{2-4}$ alkynyl, $C_{3-7}$ cycloalkyl, 3- to 7-membered saturated heterocyclyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano) $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{12A}$ and $R^{13A}$ are each independently hydrogen atom, halogen, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

Ring A is (A-1), (A-2), (A-3), or (A-4):

(A-1)

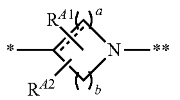

(A-2)

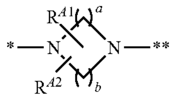

-continued (A-3)

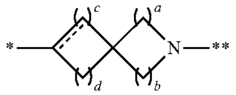

(A-4)

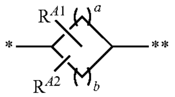

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or —$CH_2$—; and

R is methyl or isopropyl.

(Item 17)

The compound of any one of Items 1 to 16 or a pharmaceutically acceptable salt thereof, wherein M is, each independently if there are plural, $C_{1-6}$ alkylene which may be substituted with 1 to 5 the same or different substituents selected from the group consisting of fluorine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano.

(Item 18)

The compound of any one of Items 1 to 17 or a pharmaceutically acceptable salt thereof, wherein Q is, each independently if there are plural, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano.

(Item 19)

The compound of any one of Items 1 to 18 or a pharmaceutically acceptable salt thereof, wherein $R^7$ is, each independently if there are plural, hydrogen atom, $C_{1-6}$ alkyl (which may be substituted with 1 to 5 the same or different substituents selected from the group consisting of fluorine atom, phenyl, $C_{3-7}$ cycloalkyl, and 3- to 7-membered saturated heterocyclyl), $C_{2-6}$ alkenyl, $C_{2-6}$ alkynyl, $C_{3-10}$ cycloalkyl, 3- to 10-membered saturated heterocyclyl (wherein the cycloalkyl and the saturated heterocyclyl may be each independently substituted with 1 to 5 the same or different substituents selected from the group consisting of fluorine atom and $C_{1-3}$ alkyl), $C_{6-10}$ aryl, or 5- to 12-membered heteroaryl, wherein the aryl and the heteroaryl may be each independently substituted with 1 to 5 the same or different substituents selected from the group consisting of fluorine atom, chlorine atom, bromine atom, and $C_{1-3}$ alkyl.

(Item 20)

The compound of any one of Items 1 to 19 or a pharmaceutically acceptable salt thereof, wherein $R^7$ is, each independently if there are plural, hydrogen atom, $C_{1-6}$ alkyl (which may be substituted with one phenyl), or $C_{2-6}$ alkenyl.

(Item 21)

The compound of any one of Items 1 to 20 or a pharmaceutically acceptable salt thereof, wherein $R^{12A}$ and $R^{13A}$ are each independently hydrogen atom, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{4-3}$ alkoxy, —$CONR^{36}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are each attached to form 3- to 8-membered saturated carbocycle.

(Item 22)

The compound of any one of Items 1 to 21 or a pharmaceutically acceptable salt thereof, wherein $R^1$, $R^2$, $R^3$, and $R^4$ are each independently hydrogen atom, halogen, —$OR^7$, or -M-Q; or $R^1$ and $R^2$ and/or $R^3$ and $R^4$ may be combined together to form each independently =O or =$CR^{12A}R^{13A}$;

M is, each independently if there are plural, $C_{1-6}$ alkylene which may be substituted with 1 to 3 the same or different substituents selected from the group consisting of fluorine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

Q is, each independently if there are plural, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 3 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl (which may be substituted with one phenyl), or $C_{2-6}$ alkenyl;

$R^{12A}$ and $R^{13A}$ are each independently hydrogen atom, $C_{1-6}$ alkyl (which may be substituted with 1 to 3 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 3 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{37A}$, —$NR^{36A}SO_2R^{35A}$, —$SO_2R^{35A}$, —$SO_2NR^{37A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

Ring A is (A-1), (A-2), or (A-3):

(A-1)

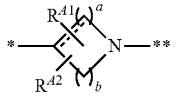

(A-2)

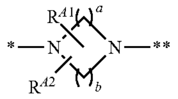

(A-3)

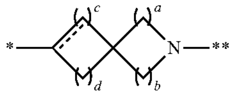

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are independently 1, 2, or 3; and

L is single bond or —$CH_2$—.

(Item 23)

The compound of any one of Items 1 to 22 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently =O or =$CR^{12A}R^{13A}$.

(Item 24)

The compound of any one of Items 1 to 23 or a pharmaceutically acceptable salt thereof, wherein M is, each independently if there are plural, $C_{1-3}$ alkylene which may be substituted with 1 to 3 the same or different substituents selected from the group consisting of fluorine atom, $C_{2-4}$ alkynyl, $C_{1-3}$ alkoxy, —$NR^{36A}R^{37A}$, and cyano; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-conLaining saturated heterocycle.

(Item 25)

The compound of any one of Items 1 to 24 or a pharmaceutically acceptable salt thereof, wherein M is, each independently if there are plural, $C_{1-3}$ alkylene.

(Item 26)

The compound of any one of Items 1 to 25 or a pharmaceutically acceptable salt thereof, wherein Q is, each independently if there are plural, $C_{3-6}$ cycloalkyl, 3- to 6-membered saturated heterocyclyl, phenyl, or 5- to 6-membered heteroaryl, wherein the cycloalkyl, the saturated heterocyclyl, the phenyl, and the heteroaryl may be each independently substituted with 1 to 3 the same or different substituents selected from the group consisting of fluorine atom, chlorine atom, bromine atom, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 27)

The compound of any one of Items 1 to 26 or a pharmaceutically acceptable salt thereof, wherein Q is, each independently if there are plural, $C_{3-6}$ cycloalkyl, 3- to 6-membered saturated heterocyclyl, phenyl, or 5- to 6-membered heteroaryl, wherein the cycloalkyl, the saturated heterocyclyl, the phenyl, and the heteroaryl may be each independently substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 28)

The compound of any one of Items 1 to 27 or a pharmaceutically acceptable salt thereof, wherein Q is, each independently if there are plural, $C_{3-6}$ cycloalkyl which may be substituted with 1 to 3 the same or different substituents selected from the group consisting of fluorine atom, $C_{1-3}$ alkyl, —$NR^{36A}SO_2R^{35A}$, —$SO_2NR^{36A}R^{37A}$, and cyano;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 29)

The compound of any one of Items 1 to 28 or a pharmaceutically acceptable salt thereof, wherein $R^{12A}$ and $R^{13A}$ are each independently hydrogen atom, $C_{1-6}$ alkyl (which may be substituted with 1 to 3 the same or different substituents selected from the group consisting of fluorine atom, $—NR^{36A}SO_2R^{35A}$, $—SO_2NR^{36A}R^{37A}$, and cyano), $C_{3-10}$ cycloalkyl (which may be substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano), and if there are plural $R^{12A}$ or $R^{13A}$, each $R^{12A}$ or $R^{13A}$ may be the same or different, or when $R^{12A}$ and $R^{13A}$ are both $C_{1-3}$ alkyl, they may be combined with the carbon atom to which they are attached to form 3- to 6-membered saturated carbocycle;

$R^{35A}$ is, each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$, or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 30)

The compound of any one of Items 1 to 29 or a pharmaceutically acceptable salt thereof, wherein $R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $—NR^{36A}SO_2R^{35A}$, $—SO^2NR^{36A}R^{37A}$, and cyano, and if there are plural $R^{12A}$ and $R^{13A}$, each $R^{12A}$ and $R^{13A}$ may be the same or different; $R^{35A}$ is each independently if there are plural, $C_{1-6}$ alkyl; and $R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle.

(Item 31)

The compound of any one of Items 1 to 30 or a pharmaceutically acceptable salt thereof, wherein Ring A is (A-1) or (A-3):

(A-1)

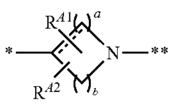

(A-3)

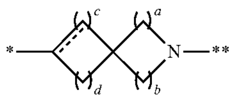

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene; and a, b, c, and d are independently 1, 2, or 3.

(Item 32)

The compound of any one of Items 1 to 31 or a pharmaceutically acceptable salt thereof, wherein L is single bond.

(Item 33)

The compound of any one of Items 1 to 31 or a pharmaceutically acceptable salt thereof, wherein L is methylene.

(Item 34)

The compound of any one of Items 1 to 30 or a pharmaceutically acceptable salt thereof, wherein Ring A is (A-1):

(A-1)

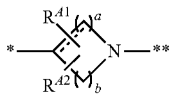

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with alkylene;

a, b, c, and d are independently 1, 2, or 3; and

L is single bond.

(Item 35)

The compound of any one of Items 1 to 30 or a pharmaceutically acceptable salt thereof, wherein Ring A is (A-1):

(A-1)

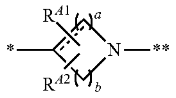

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are independently 1, 2, or 3; and

L is methylene.

(Item 36)

The compound of any one of Items 1 to 30 or a pharmaceutically acceptable salt thereof, wherein Ring A is (A-3):

(A-3)

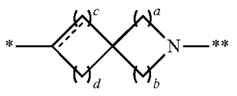

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are independently 1, 2, or 3; and

L is single bond.

(Item 37)

The compound of any one of Items 1 to 30 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently =O or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{12A}$ and $R^{13A}$ are each independently hydrogen atom or $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

Ring A is (A-1), (A-2), or (A-3):

(A-1)

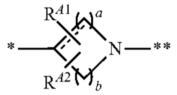

(A-2)

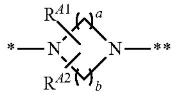

(A-3)

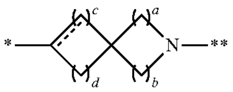

wherein * is a bonding site to L, ** is a bonding site to X, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are independently 1, 2, or 3; and

L is single bond or $-CH_2-$.

(Item 38)

The compound of any one of Items 1 to 37 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=CR^{12A}R^{13A}$.

(Item 39)

The compound of any one of Items 1 to 38 or a pharmaceutically acceptable salt thereof, wherein M is methylene.

(Item 40)

The compound of any one of Items 1 to 39 or a pharmaceutically acceptable salt thereof, wherein Q is, each independently if there are plural, $C_{3-6}$ cycloalkyl which may be substituted with 1 to 3 the same or different substituents selected from the group consisting of fluorine atom and $C_{1-3}$ alkyl.

(Item 41)

The compound of any one of Items 1 to 40 or a pharmaceutically acceptable salt thereof, wherein Q is, each independently if there are plural, $C_{3-6}$ cycloalkyl.

(Item 42)

The compound of any one of Items 1 to 41 or a pharmaceutically acceptable salt thereof, wherein $R^{12A}$ and $R^{13A}$ are each independently hydrogen atom or $C_{3-6}$ cycloalkyl.

(Item 43)

The compound of any one of Items 1 to 42 or a pharmaceutically acceptable salt thereof, wherein $R^{12A}$ and $R^{13A}$ are hydrogen atom.

(Item 44)

The compound of any one of Items 1 to 43 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene; and

Q is, each independently if there are plural, $C_{3-6}$ cycloalkyl.

(Item 45)

The compound of any one of Items 1 to 44 or a pharmaceutically acceptable salt thereof, wherein $R^1$ and $R^2$ are hydrogen atom; and $R^3$ and $R^4$ are each independently hydrogen atom or fluorine atom;

provided that both $R^3$ and $R^4$ are not simultaneously hydrogen atom.

(Item 46)

The compound of any one of Items 1 to 44 or a pharmaceutically acceptable salt thereof, wherein $R^1$ and $R^2$ are each independently hydrogen atom or -M-Q; and $R^3$ and $R^4$ are each independently hydrogen atom or fluorine atom;

provided that both $R^1$ and $R^2$ are not simultaneously hydrogen atom.

(Item 47)

The compound of any one of Items 1 to 44 or a pharmaceutically acceptable salt thereof, wherein $R^1$ is hydrogen atom, $R^2$ is -M-Q, $R^3$ is hydrogen atom, and $R^4$ is hydrogen atom or fluorine atom.

(Item 48)

The compound of any one of Items 1 to 44 or a pharmaceutically acceptable salt thereof, wherein $R^1$ is -M-Q, $R^2$ is hydrogen atom, $R^3$ is hydrogen atom or fluorine atom, and $R^4$ is hydrogen atom.

(Item 49)

The compound of any one of Items 1 to 44 or a pharmaceutically acceptable salt thereof, wherein $R^1$, $R^2$, $R^3$, and $R^4$ are each independently hydrogen atom; or $R^1$ and $R^2$ and/or $R^3$ and $R^4$ may be combined together to form $=CH_2$;

provided that all of $R^1$, $R^2$, $R^3$ and $R^4$ are not simultaneously hydrogen atom.

(Item 50)

The compound of any one of Items 1 to 44 or a pharmaceutically acceptable salt thereof, wherein $R^1$ and $R^2$ are combined together to form $=CH_2$; and $R^3$ and $R^4$ are hydrogen atom.

(Item 51)

The compound of any one of Items 1 to 44 or a pharmaceutically acceptable salt thereof, wherein $R^1$ and $R^2$ are hydrogen atom; and $R^3$ and $R^4$ are combined together to form $=CH_2$.

(Item 52)

The compound of any one of Items 6 to 51 or a pharmaceutically acceptable salt thereof, wherein the sum of a and b is 2.

(Item 53)

The compound of any one of Items 6 to 51 or a pharmaceutically acceptable salt thereof, wherein the sum of a and b is 3.

(Item 54)

The compound of any one of Items 6 to 51 or a pharmaceutically acceptable salt thereof, wherein the sum of a and b is 4.

(Item 55)

The compound of any one of Items 6 to 51 or a pharmaceutically acceptable salt thereof, wherein the sum of a and b is 5.

(Item 56)

The compound of any one of Items 6 to 51 or a pharmaceutically acceptable salt thereof, wherein the sum of a and b is 6.

(Item 57)

The compound of any one of Items 1 to 56 or a pharmaceutically acceptable salt thereof, wherein p is 1.

(Item 58)

The compound of any one of Items 1 to 56 or a pharmaceutically acceptable salt thereof, wherein p is 2.

(Item 59)

The compound of Item 1 or a pharmaceutically acceptable salt thereof, selected from:

2-(3-{1-[(3S)-2-azabicyclo[2.2.2]octane-3-carbonyl]piperidin-4-yl}-1H-pyrrolo[2,3-c]pyridin-1-yl)-5-fluoro-N,N-di(propan-2-yl)benzamide (Example 1), 2-(3-{1-[(3S)-2-azabicyclo[2.2.2]octane-3-carbonyl]-1,2,3,6-tetrahydropyridin-4-yl}-1H-pyrrolo[2,3-c]pyridin-1-yl)-5-fluoro-N-methyl-N-(propan-2-yl)benzamide (Example 2), 2-(3-{1-[(3S)-2-azabicyclo[2.2.2]octane-3-carbonyl]-1,2,3,6-tetrahydropyridin-4-yl}-1H-pyrrolo[2,3-c]pyridin-1-yl)-5-fluoro-N,N-di(propan-2-yl)benzamide (Example 3), 2-(3-{1-[(3S)-2-azabicyclo[2.2.2]octane-3-carbonyl]piperidin-4-yl}-1H-pyrrolo[2,3-c]pyridin-1-yl)-5-fluoro-N-methyl-N-(propan-2-yl)benzamide (Example 4), 5-fluoro-2-(3-{1-[(1S,3S,4R)-5-methylidene-2-azabicyclo[2.2.2]octane-3-carbonyl]piperidin-4-yl}-1H-pyrrolo[2,3-c]pyridin-1-yl)-N,N-di(propan-2-yl)benzamide (Example 5), 2-(3-{1-[(1S,3S,4R,6S)-6-(cyclopropylmethyl)-2-azabicyclo[2.2.2]octane-3-carbonyl]piperidin-4-yl}-1H-pyrrolo[2,3-c]pyridin-1-yl)-5-fluoro-N,N-di(propan-2-yl)benzamide (Example 6), 2-(3-{1-[(3S)-2-azabicyclo[2.2.2]octane-3-carbonyl]pyrrolidin-3-yl}-1H-pyrrolo[2,3-c]pyridin-1-yl)-5-fluoro-N-methyl-N-(propan-2-yl)benzamide (Example 7), 2-(3-{1-[(3S)-2-azabicyclo[2.2.2]octane-3-carbonyl]pyrrolidin-3-yl}-1H-pyrrolo[2,3-c]pyridin-1-yl)-5-fluoro-N,N-di(propan-2-yl)benzamide (Example 8), 2-(3-{1-[(3S)-2-azabicyclo[2.2.2]octane-3-carbonyl]piperidin-3-yl}-1H-pyrrolo[2,3-c]pyridin-1-yl)-5-fluoro-N-methyl-N-(propan-2-yl)benzamide (Example 9), 2-(3-{1-[(1R,3S,4S)-2-azabicyclo[2.2.1]heptane-3-carbonyl]azepan-4-yl}-1H-pyrrolo[2,3-c]pyridin-1-yl)-5-fluoro-N-methyl-N-(propan-2-yl)benzamide (Example 10), 2-(3-{1-[(3S)-2-azabicyclo[2.2.2]octane-3-carbonyl]azepan-4-yl}-1H-pyrrolo[2,3-c]pyridin-1-yl)-5-fluoro-N-methyl-N-(propan-2-yl)benzamide (Example 11), 5-fluoro-2-(3-{1-[(1S,3S,4S,5S)-5-fluoro-2-azabicyclo[2.2.2]octane-3-carbonyl]azepan-4-yl}-1H-pyrrolo[2,3-c]pyridin-1-yl)-N-methyl-N-(propan-2-yl)benzamide (Example 12), 5-fluoro-N-methyl-2-(3-{1-[(1S,3S,4R)-5-methylidene-2-azabicyclo[2.2.1]heptane-3-carbonyl]azepan-4-yl}-1H-pyrrolo[2,3-c]pyridin-1-yl)-N-(propan-2-yl)benzamide (Example 13), 2-(3-{1-[(3S)-2-azabicyclo[2.2.2]octane-3-carbonyl]-1,2,3,4,7,8-hexahydroazocin-5-yl}-1H-pyrrolo[2,3-c]pyridin-1-yl)-5-fluoro-N,N-di(propan-2-yl)benzamide (Example 14), 2-(3-{1-[(3S)-2-azabicyclo[2.2.2]octane-3-carbonyl]azocan-5-yl}-1H-pyrrolo[2,3-c]pyridin-1-yl)-5-fluoro-N-methyl-N-(propan-2-yl)benzamide (Example 15), 5-fluoro-N-methyl-2-(3-{1-[(1S,3S,4R)-5-methylidene-2-azabicyclo[2.2.2]octane-3-carbonyl]azocan-5-yl}-1H-pyrrolo[2,3-c]pyridin-1-yl)-N-(propan-2-yl)benzamide (Example 16), 2-(3-{1-[(3S)-2-azabicyclo[2.2.2]octane-3-carbonyl]azocan-5-yl}-1H-pyrrolo[2,3-c]pyridin-1-yl)-5-fluoro-N,N-di(propan-2-yl)benzamide (Example 17), 5-fluoro-2-(3-{1-[(1S,3S,4R)-5-methylidene-2-azabicyclo[2.2.2]octane-3-carbonyl]azocan-5-yl}-1H-pyrrolo[2,3-c]pyridin-1-yl)-N,N-di(propan-2-yl)benzamide (Example 18), 2-(3-{8-[(3S)-2-azabicyclo[2.2.2]octane-3-carbonyl]-8-azabicyclo[3.2.1]oct-2-en-3-yl}-1H-pyrrolo[2,3-c]pyridin-1-yl)-5-fluoro-N,N-di(propan-2-yl)benzamide (Example 19a)

2-(3-{8-[(3S)-2-azabicyclo[2.2.2]octane-3-carbonyl]-8-azabicyclo[3.2.1]oct-2-en-3-yl}-1H-pyrrolo[2,3-c]pyridin-1-yl)-5-fluoro-N,N-di(propan-2-yl)benzamide (Example 19b)

2-(3-{8-[(3S)-2-azabicyclo[2.2.2]octane-3-carbonyl]-8-azabicyclo[3.2.1]octan-3-yl}-1H-pyrrolo[2,3-c]pyridin-1-yl)-5-fluoro-N-methyl-N-(propan-2-yl)benzamide (Example 20)

5-fluoro-N-methyl-2-(3-{8-[(1S,3S,4R)-5-methylidene-2-azabicyclo[2.2.2]octane-3-carbonyl]-8-azabicyclo[3.2.1]octan-3-yl}-1H-pyrrolo[2,3-c]pyridin-1-yl)-N-(propan-2-yl)benzamide (Example 21)

2-(3-{8-[(3S)-2-azabicyclo[2.2.2]octane-3-carbonyl]-8-azabicyclo[3.2.1]octan-3-yl}-1H-pyrrolo[2,3-c]pyridin-1-yl)-5-fluoro-N,N-di(propan-2-yl)benzamide (Example 22)

5-fluoro-2-(3-{8-[(1S,3S,4R)-5-methylidene-2-azabicyclo[2.2.2]octane-3-carbonyl]-8-azabicyclo[3.2.1]octan-3-yl}-1H-pyrrolo[2,3-c]pyridin-1-yl)-N,N-di(propan-2-yl)benzamide (Example 23)

2-(3-{2-[(1R,3S,4S)-2-azabicyclo[2.2.1]heptane-3-carbonyl]-2-azaspiro[3.4]octan-6-yl}-1H-pyrrolo[2,3-c]pyridin-1-yl)-5-fluoro-N-methyl-N-(propan-2-yl)benzamide (Example 24)

2-[3-({1-[(3S)-2-azabicyclo[2.2.2]octane-3-carbonyl]pyrrolidin-3-yl}methyl)-1H-pyrrolo[2,3-c]pyridin-1-yl]-5-fluoro-N-methyl-N-(propan-2-yl)benzamide (Example 25)

2-[3-({1-[(3S)-2-azabicyclo[2.2.2]octane-3-carbonyl]azetidin-3-yl}methyl)-1H-pyrrolo[2,3-c]pyridin-1-yl]-5-fluoro-N-methyl-N-(propan-2-yl)benzamide (Example 26), 2-[3-({1-[(3S)-2-azabicyclo[2.2.2]octane-3-carbonyl]piperidin-4-yl}methyl)-1H-pyrrolo[2,3-c]pyridin-1-yl]-5-fluoro-N-methyl-N-(propan-2-yl)benzamide (Example 27), 2-[3-({4-[(3S)-2-azabicyclo[2.2.2]octane-3-carbonyl]piperazin-1-yl}methyl)-1H-pyrrolo[2,3-c]pyridin-1-yl]-5-fluoro-N-methyl-N-(propan-2-yl)benzamide (Example 28), 2-[3-({4-[(3S)-2-azabicyclo[2.2.2]octane-3-carbonyl]-1,4-diazepan-1-yl}methyl)-1H-pyrrolo[2,3-c]pyridin-1-yl]-5-fluoro-N-methyl-N-(propan-2-yl)benzamide (Example 29), and (3S)—N-[(1S)-3-(1-{4-fluoro-2-[methyl(propan-2-yl)carbamoyl]phenyl}-1H-pyrrolo[2,3-c]pyridin-3-yl)cyclohexyl]-2-azabicyclo[2.2.2]octane-3-carboxamide (Example 30).

(Item 60)

The compound of Item 1 or a pharmaceutically acceptable salt thereof, selected from:

5-fluoro-2-(3-{1-[(1S,3S,4R)-5-methylidene-2-azabicyclo[2.2.2]octane-3-carbonyl]piperidin-4-yl}-1H-pyrrolo[2,3-c]pyridin-1-yl)-N,N-di(propan-2-yl)benzamide (Example 5), 2-(3-{1-[(1S,3S,4R,6S)-6-(cyclopropylmethyl)-2-azabicyclo[2.2.2]octane-3-carbonyl]piperidin-4-yl}-1H-pyrrolo[2,3-c]pyridin-1-yl)-5-fluoro-N,N-di(propan-2-yl)benzamide (Example 6), 5-fluoro-N-methyl-2-(3-{1-[(1S,3S,4R)-5-methylidene-2-azabicyclo[2.2.1]heptane-3-carbonyl]azepan-4-yl}-1H-pyrrolo[2,3-c]pyridin-1-yl)-N-(propan-2-yl)benzamide (Example 13), and 2-[3-({1-[(3S)-2-azabicyclo[2.2.2]octane-3-carbonyl]pyrrolidin-3-yl}methyl)-1H-pyrrolo[2,3-c]pyridin-1-yl]-5-fluoro-N-methyl-N-(propan-2-yl)benzamide (Example 25)

(Item 61)

A medicament comprising the compound of any one of Items 1 to 60 or a pharmaceutically acceptable salt thereof as an active ingredient.

(Item 62)

An antitumor medicament comprising the compound of any one of Items 1 to 60 or a pharmaceutically acceptable salt thereof as an active ingredient.

(Item 63)

The antitumor medicament of Items 62, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

(Item 64)

The antitumor medicament of Item 62 or 63, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic myeloid leukemia, malignant lymphoma (including B-cell lymphoma), myeloma (including multiple myeloma), brain tumor, prostate cancer, breast cancer, neuroblastoma, Ewing's sarcoma, or liver cancer.

(Item 65)

The antitumor medicament of any one of Items 62 to 64, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, multiple myeloma, neuroblastoma, or prostate cancer.

(Item 66)

The antitumor medicament of any one of Items 62 to 65, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, or multiple myeloma.

(Item 67)

The antitumor medicament of any one of Items 62 to 66, wherein the tumor is MLL acute leukemia, or NPM mutated acute leukemia.

(Item 68)

The antitumor medicament of any one of Items 62 to 67, wherein the tumor is accompanied by high expression of HOXa gene cluster, or MEIS gene cluster.

(Item 69)

The antitumor medicament of any one of Items 62 to 68, wherein the tumor is accompanied by p53 gain-of-function mutation.

(Item 70)

A method for treating a tumor comprising administrating the compound of any one of Items 1 to 60 or a pharmaceutically acceptable salt thereof to a patient in need thereof.

(Item 71)

The method of Item 70, wherein the tumor is involved in Menin-MLL.

(Item 72)

Use of the compound of any one of Items 1 to 60 or a pharmaceutically acceptable salt thereof in the manufacture of an antitumor medicament.

(Item 73)

The compound of any one of Items 1 to 60 or a pharmaceutically acceptable salt thereof for use in the treatment of a tumor.

(Item 74)

A pharmaceutical composition comprising the compound of any one of Items 1 to 60 or a pharmaceutically acceptable salt thereof in combination with at least one different agent, wherein the different agent is at least one agent selected from the group consisting of an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, an biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

(Item 75)

The compound of any one of Items 1 to 60 or a pharmaceutically acceptable salt thereof for treating a tumor, which is used in combination with at least one different agent, wherein the different agent is at least one agent selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

Effect of the Invention

The present invention provides an inhibitor of the binding between menin and MLL fusion protein, comprising a crosslinked optically-active secondary amine derivative or a pharmaceutically acceptable salt thereof. The compound of the present invention is useful as a medicament for diseases involved in the binding between menin and MLL, and is applicable to a patient suffering from, specifically, MLL acute leukemia, NPM mutated acute leukemia, prostate cancer, breast cancer, Ewing's sarcoma, liver cancer, p53 gain-of-function mutated cancer, and the like.

DESCRIPTION OF EMBODIMENTS

Hereinafter, terms used herein are explained as follows.

The "halogen atom" includes, for example, fluorine atom, chlorine atom, bromine atom, iodine atom, and the like. It is preferably fluorine atom.

The "$C_{1-6}$ alkyl" means alkyl having 1 to 6 carbon atoms, and "$C_6$ alkyl" means alkyl having 6 carbon atoms. The same is applied to the case of the other carbon numbers. The "$C_{1-6}$ alkyl" means straight or branched chain saturated hydrocarbon group having 1 to 6 carbon atoms. The $C_{1-6}$ alkyl includes preferably "$C_{1-4}$ alkyl", more preferably "$C_{1-3}$ alkyl". The "$C_{1-3}$ alkyl" includes, for example, methyl, ethyl, propyl, 1-methylethyl, and the like. The "$C_{1-4}$ alkyl" includes, for example, butyl, 1,1-dimethylethyl, 1-methylpropyl, 2-methylpropyl, and the like, besides the examples listed in the said "$C_{1-3}$ alkyl". The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like, besides the examples listed in the said "$C_{1-4}$ alkyl".

The "$C_{1-4}$ alkyl" in "$C_{1-4}$ alkylamino" is as defined in the above-mentioned "$C_{1-4}$ alkyl", and the "$C_{2-8}$ alkyl" in "$C_{2-8}$ dialkylamino" means that the sum of the carbons included in the two alkyl groups is 2-8.

The "$C_{2-6}$ alkenyl" means straight or branched chain unsaturated hydrocarbon group having 2 to 6 carbon atoms and 1 to 3 double bonds. The "$C_{2-6}$ alkenyl" includes preferably "$C_{2-4}$ alkenyl". The "$C_{2-4}$ alkenyl" includes, for example, vinyl, propenyl, methylpropenyl, butenyl, and the like. The "$C_{2-6}$ alkenyl" includes, for example, pentenyl, hexenyl, and the like, besides the examples listed in the said "$C_{2-4}$ alkenyl".

The "$C_{2-6}$ alkynyl" means straight or branched chain unsaturated hydrocarbon group having 2 to 6 carbon atoms and a triple bond. The "$C_{2-6}$ alkynyl" includes preferably "$C_{2-4}$ alkynyl". The "$C_{2-4}$ alkynyl" includes, for example, propynyl, methylpropynyl, butynyl, and the like. The "$C_{2-6}$ alkynyl" includes, for example, methylbutynyl, pentynyl, hexynyl, and the like, besides the examples listed in the said "$C_{2-4}$ alkynyl".

The "$C_{1-6}$ alkoxy" means "$C_{1-6}$ alkyloxy", and the part "$C_{1-6}$ alkyl" is as defined in the said "$C_{1-6}$ alkyl". The "$C_{1-6}$ alkoxy" includes preferably "$C_{1-4}$ alkoxy", more preferably "$C_{1-3}$ alkoxy". The "$C_{1-3}$ alkoxy" includes, for example, methoxy, ethoxy, propoxy, 1-methylethoxy, and the like. The "$C_{1-4}$ alkoxy" includes, for example, butoxy, 1,1-dimethylethoxy, 1-methylpropoxy, 2-methylpropoxy, and the like, besides the examples listed in the said "$C_{1-3}$ alkyl". The "$C_{1-6}$ alkoxy" includes, for example, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like, besides the examples listed in the said "$C_{1-4}$ alkoxy".

The "$C_{1-6}$ alkylene" means divalent straight or branched chain saturated hydrocarbon group having 1 to 6 carbon atoms. The "$C_{1-6}$ alkylene" includes preferably "$C_{1-4}$ alkylene", more preferably "$C_{1-3}$ alkylene". The "$C_{1-3}$ alkylene" includes, for example, methylene, ethylene, propylene, trimethylene, and the like. The "$C_{1-4}$ alkylene" includes, for example, butylene, 1,1-dimethylethylene, 1,2-dimethylethylene, 1-methyltrimethylene, 2-methyltrimethylene, and the like, besides the examples listed in the said "$C_{1-3}$ alkylene". The "$C_{1-6}$ alkylene" includes, for example, pentylene, 1,1-dimethyltrimethylene, 1,2-dimethyltrimethylene, 1-methylbutylene, 2-methylbutylene, 1-methylpentylene, 2-methylpentylene, 3-methylpentylene, hexylene, and the like, besides the examples listed in the said "$C_{1-4}$ alkylene".

The "$C_{2-6}$ alkenylene" means divalent straight or branched chain unsaturated hydrocarbon group having 2 to 6 carbon atoms and 1 to 3 double bonds. The "$C_{2-6}$ alkenylene" includes preferably "$C_{2-4}$ alkenylene". The "$C_{2-4}$ alkenylene" includes, for example, vinylene, propenylene, methylpropenylene, butynylene, and the like. The "$C_{2-6}$ alkenylene" includes, for example, pentenylene, hexenylene, and the like, besides the examples listed in the said "$C_{2-4}$ alkenyl".

The "$C_{2-6}$ alkynylene" means divalent straight or branched chain unsaturated hydrocarbon group having 2 to 6 carbon atoms and 1 to 3 triple bonds. The "$C_{2-6}$ alkynylene" includes preferably "$C_{2-4}$ alkynylene". The "$C_{2-4}$ alkynylene" includes, for example, ethynylene, propynylene, butynylene, and the like. The "$C_{2-6}$ alkynylene" includes, for example, methylbutynylene, pentynylene, hexynylene, and the like, besides the examples listed in the said "$C_{2-4}$ alkynylene".

The "$C_{3-10}$ cycloalkyl" means cyclic saturated hydrocarbon group having 3 to 10 carbon atoms, which may have a partially-unsaturated bond or a bridged structure. The "$C_{3-10}$ cycloalkyl" includes preferably "$C_{3-7}$ cycloalkyl". The "$C_{3-7}$ cycloalkyl" includes, for example, cyclopropyl, cyclobutyl, cyclopentyl, cyclohexyl, cycloheptyl, and the like. The "$C_{3-10}$ cycloalkyl" includes, for example, cyclooctyl, cyclononyl, cyclodecyl, adamantyl, and the like, besides the examples listed in the said "$C_{3-7}$ cycloalkyl".

The "$C_{3-10}$ cycloalkyl" also encompasses bicyclic compounds, i.e., $C_{3-10}$ cycloalkyl fused with an aromatic hydrocarbon ring. The fused ring compounds includes, for example, the following structures:

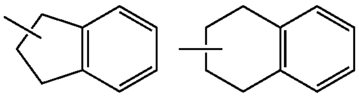

The "$C_{3-10}$ cycloalkylene" means divalent cyclic saturated hydrocarbon group having 3 to 10 carbon atoms, which may have a partially-unsaturated bond or a bridged structure. The "$C_{3-10}$ cycloalkylene" includes preferably "$C_{3-7}$ cycloalkylene". The "$C_{3-7}$ cycloalkylene" includes, for example, cyclopropylene, cyclobutylene, cycloheptylene, cyclohexylene, cycloheptylene, and the like. The "$C_{3-10}$ cycloalkylene" includes, for example, cyclooctylene, cyclononylene, cyclodecylene, adamantylene, and the like, besides the examples listed in the said "$C_{3-7}$ cycloalkylene".

The "3- to 8-membered saturated carbocycle" means cyclic saturated hydrocarbon group having 3 to 8 carbon atoms. The "3- to 8-membered saturated carbocycle" includes preferably "4- to 6-membered saturated carbocycle". The "4- to 6-membered saturated carbocycle" includes, for example, cyclobutane ring, cyclopentane ring, cyclohexane ring, and the like. The "3- to 8-membered saturated carbocycle" includes, for example, cyclopropane ring, cycloheptane ring, cyclooctane ring, and the like, besides the examples listed in the said "4- to 6-membered saturated carbocycle".

The "3- to 10-membered saturated heterocyclyl" means monovalent or divalent saturated heterocycle consisting of to 2 atoms selected independently from the group consisting of nitrogen atom, oxygen atom and sulfur atom, and 2 to 9 carbon atoms, which may include a bicyclic structure such as a bridged structure and a Spiro structure, and have a partially-unsaturated bond. The atoms of which the ring consists may include oxidized atoms such as —C(O)—, —S(O)—, and —$SO_2$—. The "3- to 10-membered saturated heterocyclyl" is preferably "4- to 7-membered monocyclic saturated heterocyclyl", more preferably "5- or 6-membered monocyclic saturated heterocyclyl". The "5- or 6-membered monocyclic saturated heterocyclyl" includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl, tetrahydrofurylene, pyrrolidinylene, imidazolidinylene, piperidinylene, morpholinylene, thiomorpholinylene, dioxothiomorpholinylene, hexamethyleneiminylene, oxazolidinylene, thiazolidinylene, oxoimidazolidinylene, dioxoimidazolidinylene, oxooxazolidinylene, dioxooxazolidinylene, dioxothiazolidinylene, tetrahydrofuranylene, tetrahydropyranylene, and the like. The "4- to 7-membered monocyclic saturated heterocyclyl" includes, for example, oxetanyl, azetidinyl, oxetanylene, azetidinylene, and the like, besides the examples listed in the said "5- or 6-membered monocyclic saturated heterocyclyl". The "3- to 10-membered saturated heterocyclyl" includes, for example, oxiranyl, aziridinyl, oxetanylene, aziridinylene, and the like, besides the examples listed in the said "4- to 7-membered monocyclic saturated heterocyclyl".

The "3- to 10-membered saturated heterocyclyl" also encompasses bicyclic compounds, i.e., "3- to 10-membered saturated heterocyclyl" fused with a 6-membered aromatic hydrocarbon ring or a 6-membered aromatic heterocycle. The 6-membered aromatic hydrocarbon ring in the fused ring includes benzene ring and the like. The 6-membered aromatic heterocycle in the fused ring includes pyridine, pyrimidine, pyridazine, and the like. The bicyclic "3- to 10-membered saturated heterocyclyl" includes dihydroindolyl, dihydroisoindolyl, dihydropurinyl, dihydrothiazolopyrimidinyl, dihydrobenzodioxanyl, isoindolyl, indazolyl, tetrahydroquinolinyl, tetrahydroisoquinolinyl, tetrahydronaphthyridinyl, dihydroindolylene, dihydroisoindolylene, dihydropurinylene, dihydrothiazolopyrimidinylene, dihydrobenzodioxanylene, isoindolylene, indazolylene, tetrahydroquinolinylene, tetrahydroisoquinolinylene, tetrahydronaphthyridinylene, and the like.

The "3- to 8-membered nitrogen-containing saturated heterocycle" means a saturated heterocycle which consists of a nitrogen atom and 2 to 7 carbon atoms. The "3- to 8-membered nitrogen-containing saturated heterocycle" includes preferably "4- to 6-membered nitrogen-containing saturated heterocycle". The "4- to 6-membered nitrogen-containing saturated heterocycle" includes, for example, azetidine ring, pyrrolidine ring, piperidine ring, and the like. The "3- to 8-membered nitrogen-containing saturated heterocycle" includes, for example, aziridine ring, azepane ring, azocane ring, and the like, besides the examples listed in the said "4- to 6-membered nitrogen-containing saturated heterocycle".

The "$C_{6-10}$ aryl" means aromatic hydrocarbon ring having to 10 carbon atoms. The "$C_{6-10}$ aryl" includes, for example, phenyl, 1-naphthyl, 2-naphthyl, and the like. It includes preferably phenyl.

The "$C_{6-10}$ aryl" also encompasses bicyclic compounds, i.e., $C_{6-10}$ aryl fused with $C_{4-6}$ cycloalkyl or 5- or 6-membered saturated heterocycle. The bicyclic "$C_{6-10}$ aryl" includes, for example, the following groups:

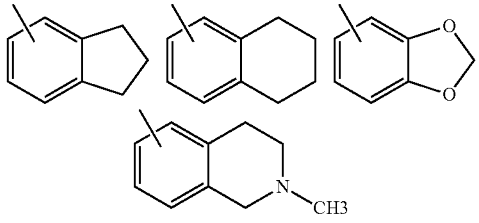

The "$C_{6-10}$ arylene" means divalent aromatic hydrocarbon group having 6 to 10 carbon atoms. The "$C_{6-10}$ arylene" includes, for example, phenylene, 1-naphthylene, 2-naphthylene, and the like. It includes preferably phenylene.

The "aromatic hydrocarbon ring" means a cyclic part of the said "$C_{6-10}$ aryl" and the said "$C_{6-10}$ arylene".

The "5- to 12-membered heteroaryl" means monocyclic 5- to 7-membered aromatic heterocyclic group or bicyclic 8- to 12-membered aromatic heterocyclic group having 1 to 4 atoms selected independently from the group consisting of nitrogen atom, oxygen atom and sulfur atom. It is preferably "5- to 7-membered monocyclic heteroaryl". It is more preferably pyridyl, pyrimidinyl, quinolyl, or isoquinolyl. It is even more preferably pyridyl. The "5- to 7-membered monocyclic heteroaryl" includes, for example, pyridyl, pyridazinyl, isothiazolyl, pyrrolyl, furyl, thienyl, triazolyl, imidazolyl, pyrimidinyl, thiadiazolyl, pyrazolyl, oxazolyl, isoxazolyl, pyrazinyl, triazinyl, triazolyl, oxadiazolyl, triazolyl, tetrazolyl, and the like. The “5- to 12-membered heteroaryl” includes indolyl, indazolyl, chromenyl, quinolyl, isoquinolyl, benzofuranyl, benzothienyl, benzooxazolyl, benzothiazolyl, benzoisoxazolyl, benzoisothiazolyl, benzotriazolyl, benzoimidazolyl, and the like, besides the examples listed in the said “5- to 7-membered monocyclic heteroaryl”.

The “5- to 12-membered heteroarylene” means divalent monocyclic 5- to 7-membered aromatic heterocyclic group or divalent bicyclic 8- to 12-membered aromatic heterocyclic group having 1 to 4 atoms selected independently from the group consisting of nitrogen atom, oxygen atom and sulfur atom. It is preferably “5- to 7-membered monocyclic heteroarylene”. It is more preferably pyridylene, pyrimidylene, quinolylene, or isoquinolylene. It is even more preferably pyridylene. The “5- to 7-membered monocyclic heteroarylene” includes, for example, pyridylene, pyridazinylene, isothiazolylene, pyrrolylene, furylene, thienylene, thiazolylene, imidazolylene, pyrimidinylene, thiadiazolylene, pyrazolylene, oxazolylene, isooxazolylene, pyrazinilene, triazinylene, triazolylene, oxadiazolylene, triazolylene, tetrazolylene, and the like. The “5- to 12-membered heteroarylene” includes indolylene, indazolylene, chromenylene, quinolylene, isoquinolylene, benzofuranylene, benzothienylene, benzooxazolylene, benzothiazolylene, benzoisooxazolylene, benzoisothiazolylene, benzotriazolylene, benzoimidazolylene, and the like, besides the examples listed in the said “5- to 7-membered monocyclic heteroarylene”.

The “aromatic heterocyclic group” means a cyclic part of the said “5- to 12-membered heteroaryl” and the said “5- to 12-membered heteroarylene”.

In the present specification, a bond across a ring group as showed in the following formula (W) means that the bond is attached to a substituable position of the “group”. For example, in the case of the following formula (W):

(W)

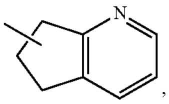

, it represents the following formula (W-1), (W-2), or (W-3):

(W-1)

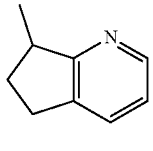

(W-2)

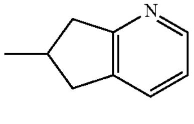

(W-3)

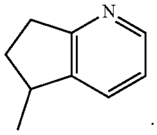

.

In the present specification, the stereochemistry of substituents in the compound of formula (I) or the example compounds can be illustrated, for example, as follows:

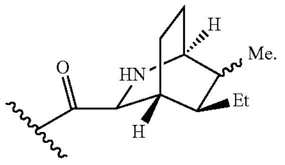 [SMILES: *C(=O)C1N[C@H]2CC[C@@H]1[C@H](CC)C2C]

In the above structure, the bonds shown as wedged line represent substituents in front of the page; the bond shown as dashed line represents a substituent in back of the page; and the bond shown as wavy line represents that the substituent exists in front and back of the page in an certain ratio, and when a bond which extends from the ring outside is shown as linear line, it represents that the bond exists either in front or back of the page.

The “cancer” and “tumor” are used interchangeably, and the both mean malignant neoplasm, which encompasses cancer, sarcoma, and hematologic malignancy. The “cancer” and “tumor” include, for example, acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, a myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms’ tumor, malignant melanoma, neuroblastoma, osteosarcoma, Ewing’s sarcoma, chondrosarcoma, soft tissue sarcoma, skin cancer, and the like. The above tumors may be accompanied by increased expression or mutation of specific genes. The tumors accompanied by increased expression of genes include, for example, tumors accompanied by high expression of HOXa gene cluster, tumors accompanied by high expression of MEIS gene cluster, and the like. The tumors accompanied by mutation of genes include tumors accompanied by p53 gain-of-function mutation and the like.

In the present compound of formula (1), preferred p, Ring A, Ring B, X, Z, L, M, Q, a, b, c, d, U, R, $R^{A1}$, $R^{A2}$, $R^{B}$, $R^{1}$, $R^{2}$, $R^{3}$, $R^{4}$, $R^{5A}$, $R^{5B}$, $R^{6A}$, $R^{6B}$, $R^{6C}$, $R^{6D}$, $R^{7}$, $R^{8}$, $R^{9}$, $R^{10}$, $R^{11}$, $R^{12A}$, $R^{12B}$, $R^{13A}$, $R^{13B}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35A}$, $R^{35B}$, $R^{36A}$, $R^{36B}$, $R^{37A}$, and $R^{37B}$ are as follows, but the technical scope of the present invention is not limited to the scope of compounds listed below.

In an embodiment, p includes 1. In another embodiment, p includes 2.

Ring A includes preferably (A-1), (A-2), (A-3), and (A-4) shown below. It is more preferably (A-1) or (A-3).

(A-1)

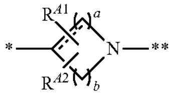

(A-2)

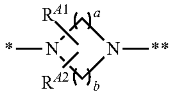

(A-3)

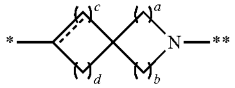

(A-4)

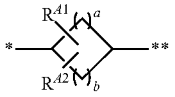

wherein * is a bonding site to L, ** is a bonding site to X, and the dot-line in the ring means that there may be optionally a unsaturated bond in the ring.

Ring B includes preferably (B-1), (B-2), (B-3), (B-4), and (B-5) shown below. It is more preferably (B-1).

(B-1)

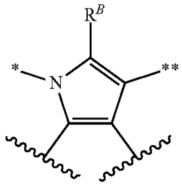

(B-2)

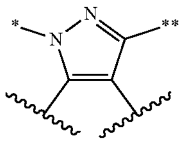

(B-3)

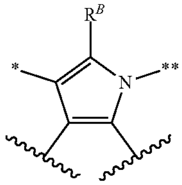

(B-4)

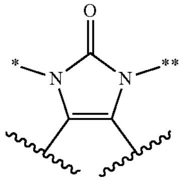

(B-5)

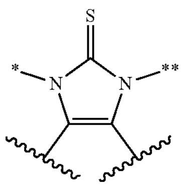

wherein * is a bonding site to the benzene ring, and ** is a bonding site to L

X is preferably —C(O)—.

Z includes preferably (Z-1), (Z-2), (Z-3), (Z-4), and (Z-5) shown below. It is more preferably (Z-1) or (Z-3).

(Z-1)

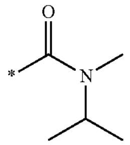

(Z-2)

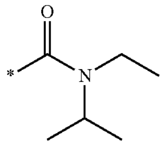

(Z-3)

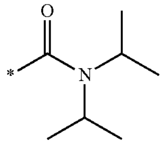

(Z-4)

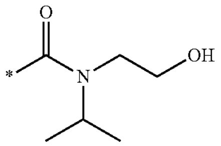

(Z-5)

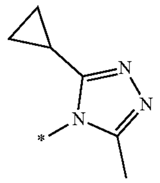

L is preferably single bond or methylene.

M includes preferably $C_{1-3}$ alkylene optionally substituted with 1 to 3 the same or different substituents selected from the group consisting of fluorine atom, $C_{2-4}$ alkynyl, $C_{1-3}$ alkoxy, $—NR^{36A}R^{37A}$, and cyano. It includes more preferably $C_{1-3}$ alkylene. It includes even more preferably methylene.

Q includes preferably $C_{3-6}$ cycloalkyl optionally-substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano; 3- to 6-membered saturated heterocyclyl optionally-substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano; phenyl optionally-substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano; and 5- to 6-membered heteroaryl optionally-substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano. It includes more preferably $C_{3-6}$ cycloalkyl optionally-substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano. It includes even more preferably $C_{3-6}$ cycloalkyl optionally-substituted with 1 to 3 the same or different substituents selected from the group consisting of fluorine atom and $C_{1-3}$ alkyl. $C_{3-6}$ cycloalkyl is especially preferable.

a and b are preferably 1, 2, or 3.

In another embodiment of a and b, the sum of a and b is 2, 3, 4, 5, or 6.

c and d are preferably 1, 2, or 3.

In another embodiment of c and d, the sum of c and d is 2, 3, 4, 5, or 6.

U is preferably CH.

R includes preferably methyl and isopropyl.

$R^{A1}$ and $R^{A2}$ include preferably hydrogen atom and $C_{1-3}$ alkyl.

In another embodiment, $R^{A1}$ and $R^{A2}$ are combined together to form a bridged structure with $C_{1-3}$ alkylene.

$R^B$ is preferably hydrogen atom.

$R^1$ includes preferably hydrogen atom and -M-Q.

$R^2$ includes preferably hydrogen atom and -M-Q.

$R^3$ includes preferably hydrogen atom and fluorine atom.

$R^4$ includes preferably hydrogen atom and fluorine atom. In another embodiment, $R^1$ and $R^2$ are combined together to form $=CR^{12A}R^{13A}$. It is more preferably $=CH_2$.

In another embodiment, $R^3$ and $R^4$ are combined together to form $=CR^{12A}R^{13A}$. It is more preferably $=CH_2$.

In another embodiment of $R^1$, $R^2$, $R^3$, and $R^4$, $R^1$ is hydrogen atom, $R^2$ is -M-Q, $R^3$ is hydrogen atom, and $R^4$ is hydrogen atom or fluorine atom.

In another embodiment of $R^1$, $R^2$, $R^3$, and $R^4$, $R^1$ is -M-Q, $R^2$ is hydrogen atom, $R^3$ is hydrogen atom or fluorine atom, and $R^4$ is hydrogen atom.

In another embodiment of $R^1$, $R^2$, $R^3$, and $R^4$, $R^1$ and $R^2$ are both hydrogen atom, and $R^3$ and $R^4$ are combined together to form $=CH_2$.

In another embodiment of $R^1$, $R^2$, $R^3$, and $R^4$, $R^3$ and $R^4$ are both hydrogen atom, and $R^1$ and $R^2$ are combined together to form $=CH_2$.

In another embodiment of $R^1$, $R^2$, $R^3$, and $R^4$, $R^1$ and $R^2$ are both hydrogen atom, $R^3$ is hydrogen atom, and $R^4$ is fluorine atom.

In another embodiment of $R^1$, $R^2$, $R^3$, and $R^4$, $R^1$ and $R^2$ are both hydrogen atom, $R^3$ is fluorine atom, and $R^4$ is hydrogen atom.

$R^{5A}$ and $R^{5B}$ are preferably hydrogen atom. $R^{6A}$, $R^{6B}$, and $R^{6D}$ are preferably hydrogen atom.

$R^{6C}$ is preferably fluorine atom.

$R^7$ is preferably hydrogen atom, $C_{1-6}$ alkyl (which may be substituted with one phenyl), or $C_{2-6}$ alkenyl.

$R^8$, $R^{14}$, $R^{18}$, $R^{25}$, $R^{31}$, $R^{35A}$, and $R^{35B}$ are preferably $C_{1-3}$ alkyl.

$R^9$, $R^{10}$, $R^{11}$, $R^{15}$, $R^{16}$, $R^{17}$, $R^{19}$, $R^{20}$, $R^{21}$, $R^{23}$, $R^{24}$, $R^{26}$, $R^{27}$, $R^{28}$, $R^{29}$, $R^{30}$, $R^{32}$, $R^{33}$, $R^{34}$, $R^{36A}$, $R^{36B}$, $R^{37A}$, and $R^{37B}$ include preferably hydrogen atom and $C_{1-3}$ alkyl.

$R^{12A}$ and $R^{13A}$ include preferably hydrogen atom and $C_{3-6}$ cycloalkyl which may be substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano. They are more preferably hydrogen atom.

$R^{12B}$ and $R^{13B}$ are preferably $C_{1-3}$ alkyl.

$R^{22}$ is preferably hydrogen atom.

In an embodiment, the present compound of formula (1) includes the following (A).

(A)

A compound or pharmaceutically acceptable salt thereof, wherein formula (1) is formula (1a);

p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=O$ or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano;

$R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $—NR^{36A}SO_2R^{35A}$, $SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

Ring A is (A-1), (A-2), or (A-3);

$R^{A1}$ and $R^{A2}$ are each independently hydrogen atom or $C_{1-3}$ alkyl, or $R^{A1}$ and RAZ may be combined with each carbon atom to which they are attached to form a bridged structure with alkylene;

a, b, c, and d are each independently 1, 2, or 3;

L is single bond or methylene; and

R is methyl or isopropyl.

An embodiment of the present compound of formula (1) includes the following (B):

(B)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=O$ or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano;

$R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

X is —C(O)—;

Ring A is (A-1), (A-2), or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene;

$R^{5A}R^{5B}$, $R^{6A}$, $R^{6B}$, $R^{6D}$ are hydrogen atom;

$R^{6C}$ is fluorine atom;

U is CH;

Ring B is (B-1);

$R^B$ is hydrogen atom; and

Z is (Z-1), (Z-2), (Z-3), (Z-4), or (Z-5).

An embodiment of the present compound of formula (1) includes the following (C):

(C)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently =O or $=CR^{12A}R^{13A}$;

M is, each independently if there are plural, $C_{1-3}$ alkylene;

Q is, each independently if there are plural, $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{12A}$ and $R^{13A}$ are each independently hydrogen atom, or $C_{3-6}$ cycloalkyl which may be substituted with 1 to 3 the same or different substituents selected from the group consisting of fluorine atom, $C_{1-3}$ alkyl, $-NR^{36A}SO_2R^{35A}$, $-SO_2NR^{36A}R^{37A}$, and cyano;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

X is —C(O)—;

Ring A is (A-1), (A-2), or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene;

$R^{5A}$, $R^{5B}$, $R^{6A}$, $R^{6B}$, and $R^{6D}$ are hydrogen atom;

$R^{6C}$ is fluorine atom;

U is nitrogen atom;

Ring B is (B-1);

$R^B$ is hydrogen atom; and

Z is (Z-3).

An embodiment of the present compound of formula (1) includes the following (D):

(D)

A compound or pharmaceutically acceptable salt thereof, wherein formula (1) is formula (1a);

p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently if there are plural, $C_{3-6}$ cycloalkyl;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene; and

R is methyl or isopropyl.

An embodiment of the present compound of formula (1) includes the following (E):

(E)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently if there are plural, $C_{3-6}$ cycloalkyl;

X is —C(O)—;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with alkylene;

a, b, c, and d are each independently 1, 2, or 3;

L is single bond or methylene;

$R^{5A}$, $R^{5B}$, $R^{6A}$, $R^{6C}$, and $R^{6D}$ are hydrogen atom;

$R^{6C}$ is fluorine atom;

U is CH;

Ring B is (B-1);

$R^B$ is hydrogen atom; and

Z is (Z-1), (Z-2), (Z-3), (Z-4), or (Z-5).

An embodiment of the present compound of formula (1) includes the following (F):

(F)

A compound or pharmaceutically acceptable salt thereof, wherein p is 1 or 2;

$R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene;

Q is, each independently if there are plural, $C_{3-6}$ cycloalkyl;

X is —C(O)—;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene;

$R^{5A}$, $R^{5B}$, $R^{6A}$, $R^{6B}$, and $R^{6D}$ are hydrogen atom;

$R^{6C}$ is fluorine atom;

U is nitrogen atom;

Ring B is (B-1);

$R^B$ is hydrogen atom; and

Z is (Z-3).

An embodiment of the present compound of formula (1) includes the following (G):

(G)

A compound or pharmaceutically acceptable salt thereof, wherein formula (1) is formula (1a);

p is 1 or 2;

$R^1$ and $R^2$ are hydrogen atom;

$R^3$ and $R^4$ are each independently hydrogen atom or fluorine atom;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene; and

R is methyl or isopropyl;

provided that both $R^3$ and $R^4$ are not simultaneously hydrogen atom.

An embodiment of the present compound of formula (1) includes the following (H):

(H)

A compound or pharmaceutically acceptable salt thereof, wherein p is 1 or 2;

$R^1$ and $R^2$ are hydrogen atom;

$R^3$ and $R^4$ are each independently hydrogen atom or fluorine atom;

X is —C(O)—;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene;

$R^{5A}$, $R^{5B}$, $R^{6A}$, $R^{6B}$, and $R^{6D}$ are hydrogen atom;

$R^{6C}$ is fluorine atom;

U is CH;

Ring B is (B-1);

$R^B$ is hydrogen atom; and

Z is (Z-1), (Z-2), (Z-3), (Z-4), or (Z-5);

provided that both $R^3$ and $R^4$ are not simultaneously hydrogen atom.

An embodiment of the present compound of formula (1) includes the following (I):

(I)

A compound or pharmaceutically acceptable salt thereof, wherein p is 1 or 2;

$R^1$ and $R^2$ are hydrogen atom;

$R^3$ and $R^4$ are each independently hydrogen atom or fluorine atom;

X is —C(O)—;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with alkylene;

a, b, c, and d are each independently 1, 2, or 3;

L is single bond or methylene;

$R^{5A}$, $R^{5B}$, $R^{6A}$, $R^{6B}$, and $R^{6D}$ are hydrogen atom;

$R^{6C}$ is fluorine atom;

U is nitrogen atom;

Ring B is (B-1);

$R^B$ is hydrogen atom; and

Z is (Z-3);

provided that both $R^3$ and $R^4$ are not simultaneously hydrogen atom.

An embodiment of the present compound of formula (1) includes the following (J):

(J)

A compound or pharmaceutically acceptable salt thereof, wherein formula (1) is formula (1a);

p is 1 or 2;

$R^1$ and $R^2$ are each independently hydrogen atom or -M-Q;

$R^3$ and $R^4$ are each independently hydrogen atom or fluorine atom;

M is, each independently if there are plural, methylene;

Q is, each independently if there are plural, $C_{3-6}$ cycloalkyl;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene; and

R is methyl or isopropyl;

provided that both $R^1$ and $R^2$ are not simultaneously hydrogen atom.

An embodiment of the present compound of formula (1) includes the following (K):

(K)

A compound or pharmaceutically acceptable salt thereof, wherein p is 1 or 2;

$R^1$ and $R^2$ are each independently hydrogen atom or -M-Q;

$R^3$ and $R^4$ are each independently hydrogen atom or fluorine atom;

M is, each independently if there are plural, methylene;

Q is, each independently if there are plural, $C_{3-6}$ cycloalkyl;

X is —C(O)—;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene;

$R^{5A}$, $R^{5B}$, $R^{6A}$, $R^{6B}$, and $R^{6D}$ are hydrogen atom;

$R^{6C}$ is fluorine atom;

U is CH;

Ring B is (B-1);

$R^B$ is hydrogen atom; and

Z is (Z-1), (Z-2), (Z-3), (Z-4), or (Z-5);

provided that both $R^1$ and $R^2$ are not simultaneously hydrogen atom.

An embodiment of the present compound of formula (1) includes the following (L):

(L)

A compound or pharmaceutically acceptable salt thereof, wherein p is 1 or 2;

$R^1$ and $R^2$ are each independently hydrogen atom or -M-Q;

$R^3$ and $R^4$ are each independently hydrogen atom or fluorine atom;

M is, each independently if there are plural, methylene;

Q is, each independently if there are plural, $C_{3-6}$ cycloalkyl;

X is —C(O)—;

Ring A is (A-1) or (A-3);

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or methylene;

$R^{5A}$, $R^{5B}$, $R^{6A}$, $R^{6B}$, and $R^{6D}$ are hydrogen atom;
$R^{6C}$ is fluorine atom;
U is nitrogen atom;
Ring B is (B-1);
$R^B$ is hydrogen atom; and
Z is (Z-3);
provided that both R' and $R^2$ are not simultaneously hydrogen atom.

An embodiment of the present compound of formula (1) includes the following (M):

(N)

A compound or pharmaceutically acceptable salt thereof, wherein
formula (1) is formula (1a);
p is 1 or 2;
$R^1$, $R^2$, $R^3$, and $R^4$ are hydrogen atom; or $R^1$ and $R^2$ and/or $R^3$ and $R^4$ may be combined together to form $=CH_2$;
Ring A is (A-1) or (A-3);
$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with
$C_{1-3}$ alkylene;
a, b, c, and d are each independently 1, 2, or 3;
L is single bond or methylene; and
R is methyl or isopropyl;
provided that all of $R^1$, $R^2$, $R^3$ and $R^4$ are not simultaneously hydrogen atom.

An embodiment of the present compound of formula (1) includes the following (N):

(N)

A compound or pharmaceutically acceptable salt thereof, wherein
p is 1 or 2;
$R^1$, $R^2$, $R^3$, and $R^4$ are hydrogen atom; or $R^1$ and $R^2$ and/or $R^3$ and $R^4$ may be combined together to form $=CH_2$;
X is —C(O)—;
Ring A is (A-1) or (A-3);
$R^{A1}$ and $R^{A2}$ are each independently hydrogen atom or $C_{1-3}$ alkyl, or RAI- and $R^{A2}$ may be combined with each carbon atom to which they are attached to form a bridged structure with
$C_{1-3}$ alkylene;
a, b, c, and d are each independently 1, 2, or 3;
L is single bond or methylene;
$R^{5A}$, $R^{5B}$, $R^{6A}$, $R^{6B}$, and $R^{6D}$ are hydrogen atom;
$R^{6C}$ is fluorine atom;
U is CH;
Ring B is (B-1);
$R^B$ is hydrogen atom; and
Z is (Z-1), (Z-2), (Z-3), (Z-4), or (Z-5);
provided that all of $R^1$, $R^2$, $R^3$ and $R^4$ are not simultaneously hydrogen atom.

An embodiment of the present compound of formula (1) includes the following (O):

(O)

A compound or pharmaceutically acceptable salt thereof, wherein
p is 1 or 2;
$R^1$, $R^2$, $R^3$, and $R^4$ are independently hydrogen atom; or $R^1$ and $R^2$ and/or $R^3$ and $R^4$ may be combined together to form $=CH_2$;
X is —C(O)—;
Ring A is (A-1), (A-2), or (A-3);
$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;
a, b, c, and d are each independently 1, 2, or 3;
L is single bond or methylene;
$R^{5A}$, $R^{5B}$, $R^{6A}$, $R^{6B}$, and $R^{6D}$ are hydrogen atom;
$R^{6C}$ is fluorine atom;
U is nitrogen atom;
Ring B is (B-1);
$R^B$ is hydrogen atom; and
Z is (Z-3);
provided that all of $R^1$, $R^2$, $R^3$ and $R^4$ are not simultaneously hydrogen atom.

Hereinafter, the processes to prepare the compound of the present invention of formula (1) are exemplified along with examples, but the processes to prepare the compound of the present invention should not be limited to the examples. Compounds used in the following process may exist as their salts unless they affect reactions.

The compounds of the present invention can be prepared from known compounds as starting materials, for example, by the following methods A, B, C, D, E, F, G, H, I, J, K, and L, or similar methods thereto, or optionally in combination with synthetic methods well-known to a person skilled in the art.

Preparation Process A

The compound of the present invention of formula (1) can be prepared, for example, by the following process:

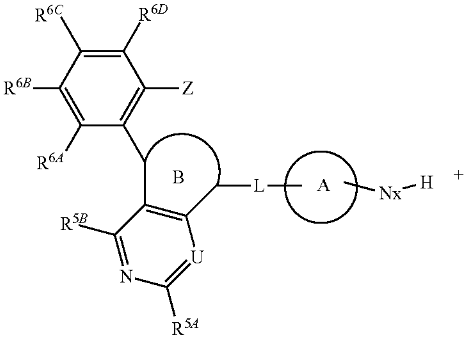

(a1)

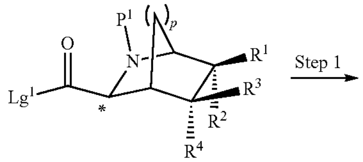

(a2)

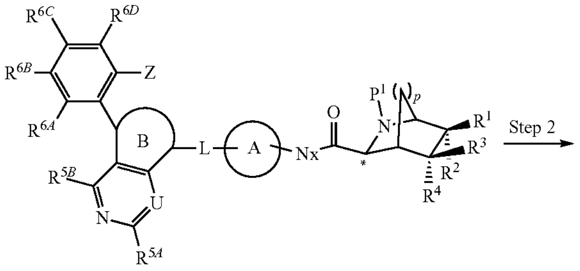

(a3)

-continued

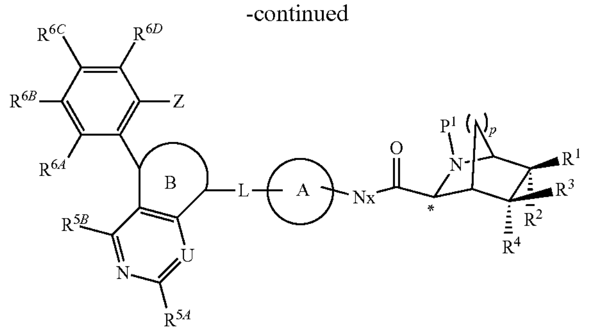

(A1)

wherein p $R^1$, $R^2$, $R^3$, $R^4$, $R^{5A}$, $R^{5B}$, $R^{6A}$, $R^{6B}$, $R^{6C}$, $R^{6D}$, U, Ring A, Ring B, L, and Z are as defined in Item 1; Nx is single bond or NH; $Lg^1$ is a leaving group; is an amino-protecting group; wherein $Lg^1$ includes, for example, halogen, hydroxy, and the like; $P^1$ includes, for example, amino-protecting groups described in Theodora W. Greene, Peter G. M. Wuts "*Protective Groups in Organic Synthesis*", John Wiley & Sons, Inc., (1999), and the like; and the stereochemistry of the carbon with * is not inverted during reactions.

(Step 1)

Compound (a3) can be prepared by reacting compound (a1) with compound (a2) such as carboxylic acid compound or acid chloride compound in the presence of an appropriate condensing agent and/or an appropriate base in an appropriate solvent.

The base used herein includes amines such as triethylamine, diisopropylethylamine, and pyridine; and carbonates of alkali metal such as potassium carbonate, sodium carbonate, and sodium bicarbonate. The base includes preferably triethylamine, diisopropylethylamine, and pyridine.

The condensing agent used herein is suitably selected from condensing agents commonly-used in organic synthetic chemistry, and includes preferably 1-ethyl-3-(3-dimethylaminopropyl)carbodiimide hydrochloride, 1-hydroxybenzotriazole, and the like.

The solvent used herein includes, for example, ether solvents such as diethyl ether, diisopropyl ether, tetrahydrofuran, methylcyclopentyl ether, and 1,4-dioxane; aromatic hydrocarbon solvents such as benzene, toluene, chlorobenzene, anisole, and xylene; ester solvents such as ethyl acetate, and methyl acetate; aprotic solvents such as acetonitrile, N,N-dimethylformamide, N,N-dimethylacetamide, N-methyl-2-pyrrolidinone, 1,3-dimethyl-2-imidazolidinone, and dimethylsulfoxide; halogenated hydrocarbon solvents such as dichloromethane (methylene chloride), chloroform, and 1,2-dichloroethane; and mixtures thereof, but should not be specifically limited thereto unless it reacts under the reaction condition of the present step. The solvent includes preferably tetrahydrofuran, toluene, acetonitrile, N,N-dimethylformamide, dichloromethane, and the like.

The reaction time is generally 5 minutes to 72 hours, preferably 30 minutes to 24 hours.

The reaction temperature is generally −78° C. to 200° C., preferably −78° C. to 80° C.

(Step 2)

Compound (A1) can be prepared by removing protecting group $P^1$ from compound (a3). The present step can be carried out, for example, according to a method described in Theodora W. Greene, Peter G. M. Wets, "*Protective Groups in Organic Synthesis*", John Wiley & Sons, Inc., (1999), or a similar method.

Preparation Process B

The compound of the present invention of formula (B1) can be prepared, for example, by the following process:

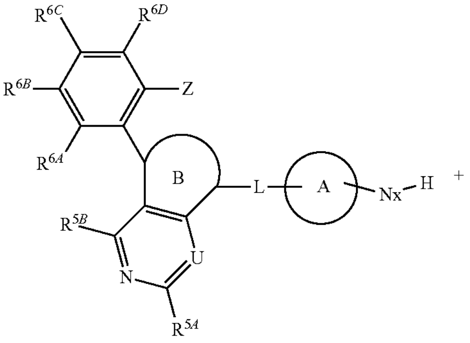

(a1)

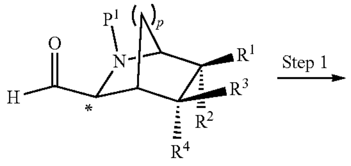

(b1)

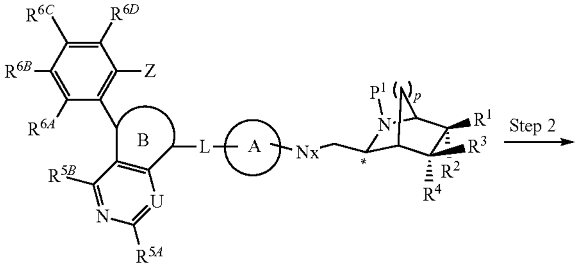

(b2)

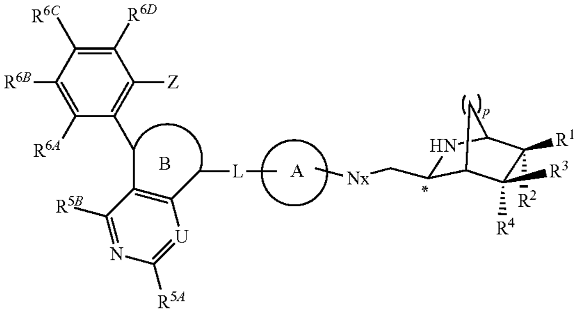

(B1)

wherein p, $R^1$, $R^2$, $R^3$, $R^4$, $R^{5A}$, $R^{5B}$, $R^{6A}$, $R^{6B}$, $R^{6C}$, $R^{6D}$, Ring A, Ring B, L, and Z are as defined in Item 1; Nx and $P^1$ are as defined in Preparation Process A; and the stereochemistry of the carbon with * is not inverted during reactions.

Compound (b1) can be obtained by a known method described in JP-A-2007-510619, *J. Chem. Soc., Chem. Commun.*, 1599-1601 (1988), *Tetrahedron Letters*, 43: 5957-5960 (2002), *Tetrahedron Asymmetry*, 2: 1263-1282 (1991), *Tetrahedron Asymmetry*, 27: 1062-1068 (2016), R. C. Larock, "*Comprehensive Organic Transformation 2nd Edition*", John Wiley & Sons, Inc., (1989) or a similar method, or can be obtained as a marketed product.

(Step 1)

Compound (b2) can be prepared from compound (a1) and compound (b1) by a known method described in *J. Am. Chem. Soc.*, 93(72): 2897-2904 (1971), *Journal of Organic Chemistry*, 37(10): 1673-1674 (1972), *Journal of Organic Chemistry*, 61(11): 3849-3862 (1996), *Tetrahedron*, 60: 7899-7906 (2004), or a similar method.

(Step 2)

Compound (B1) can be prepared by removing protecting group $P^1$ from compound (b2). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process C

In the compound of formula (a1), the compound of formula (C1) can be prepared, for example, by the following process:

(Step 1)

Compound (c3) can be prepared from Compound (c1) and Compound (c2) by a method described in *Journal of Medicinal Chemistry*, 36(25): 4006-4014 (1993), WO 2015/082499, WO 2011/113798, or a similar method.

(Step 2)

Compound (c4) can be prepared from Compound (c3) by a known method described in *Journal of Medicinal Chemistry*, 46(14): 3060-3071 (2003), WO 2015/082499, WO 2013/038189, WO 2001/0126292, or a similar method.

(Step 3)

Compound (c5) can be prepared from Compound (c4) by a known method described in *Organic Letters*, 17(21): 5484-5487 (2015), WO 2014/071247, WO 2018/053267, or a similar method.

(Step 4)

Compound (c6) can be prepared from Compound (c4) by a known method described in *Applied Organometallic Chemistry*, 29(5): 334-337 (2015), *Heterocycles*, 91 (4): 795-814 (2015), *Organic Letters*, 2(10): 1403-1406 (2000), *Tetrahedron Letters*, 51 (38): 5071-5075 (2010), WO 2018/053267, or a similar method.

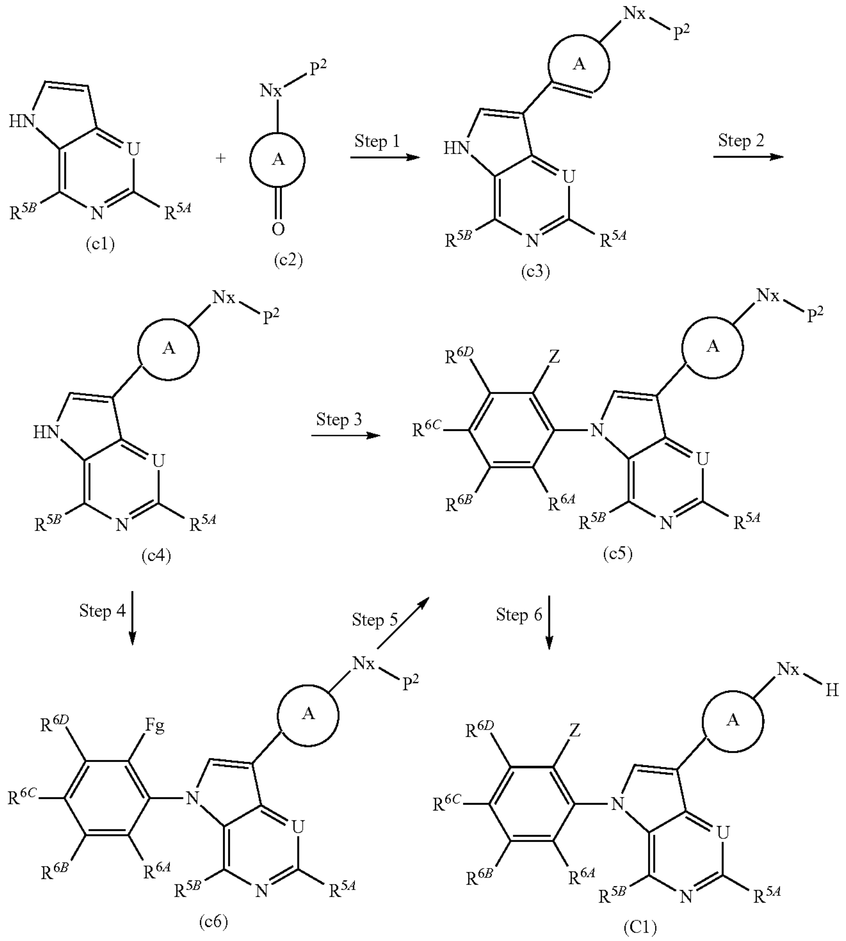

wherein $R^{5A}$, $R^{5B}$, $R^{6A}$, $R^{6B}$, $R^{6C}$, $R^{6D}$, U, Ring A, and Z are as defined in Item 1; Nx is as defined in Preparation Process A; wherein Fg is halogen, nitro, methoxycarbonyl, ethoxycarbonyl, or tert-butoxycarbonyl; $P^2$ is an amino-protecting group; and $P^2$ includes, for example, amino-protecting groups described in Theodora W. Greene, Peter G. M. Wuts "*Protective Groups in Organic Synthesis*", John Wiley & Sons, Inc., (1999), and the like.

Compound (c1) and Compound (c2) are commercially available.

(Step 5)

Compound (c5) can be prepared from Compound (c6) by a method described in WO 2018/053267 or a similar method.

(Step 6)

Compound (C1) can be prepared by removing protecting group $P^2$ from compound (c5). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process D

The compounds of formulae (c5) and (c6) can be also prepared, for example, by the following process:

Compound (d5) can be prepared from the corresponding halogenated vinyl compound in a conventional process.

(Step 1)

Compound (d1) can be prepared from compound (c1) by the method described in step 3 of preparation process C or a similar method.

(Step 2)

Compound (d2) can be prepared from compound (c1) by the method described in step 4 of preparation process C or a similar method.

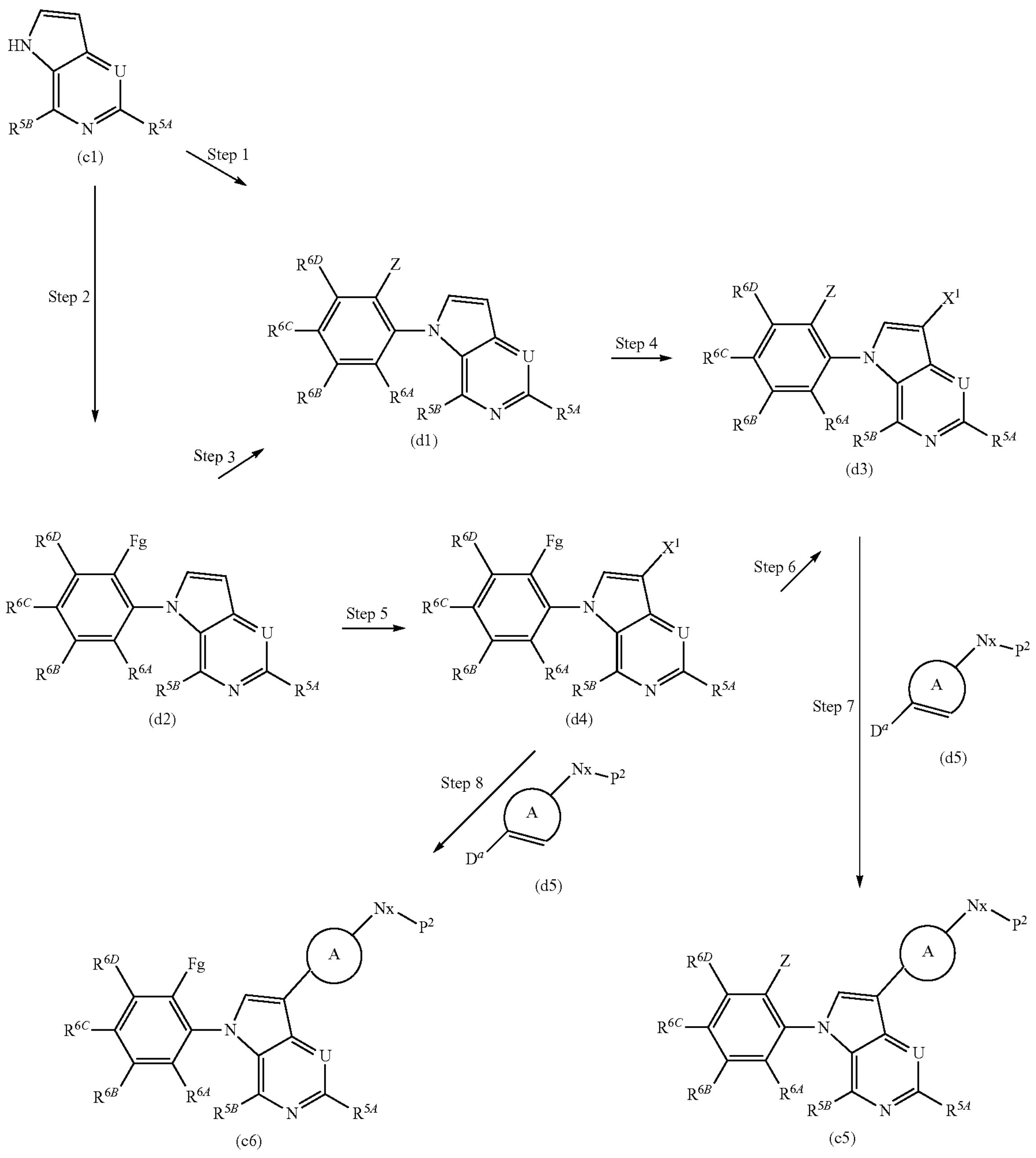

wherein $R^{5A}$, $R^{5B}$, $R^{6A}$, $R^{6B}$, $R^{6C}$, $R^{6D}$, U, Ring A, and Z are as defined in Item 1; Nx is as defined in Preparation Process A; Fg and $P^2$ are as defined in Preparation Process C; $X^1$ is halogen; and $D^a$ is alkoxyboron, alkyltin, alkylsilyl, alkylzinc, halogenated magnesium, or the like.

(Step 3)

Compound (d1) can be prepared from compound (d2) by the method described in step 5 of preparation process C or a similar method.

(Step 4)

Compound (d3) can be prepared from Compound (d1) by a method described in WO 2013/100506, WO 2011/158108, or a similar method.

(Step 5)

Compound (d4) can be prepared from compound (d2) by the method described in step 4 or a similar method.

(Step 6)

Compound (d3) can be prepared from compound (d4) by the method described in step 3 or a similar method.

(Step 7)

Compound (c5) can be prepared from Compound (d3) and Compound (d5) by a method described in *Bioorganic Medicinal Chemistry,* 26(4): 913-924 (2018), WO 2014/028597, WO 2004/092124, *Organic Letters,* 9(8): 1505-1508 (2007), or a similar method.

(Step 8)

Compound (c6) can be prepared from Compound (d4) and Compound (d5) by the method described in step 7 or a similar method.

Preparation Process E

In the compound of formula (a1), the compound of formula (E1) can be prepared, for example, by the following process:

Compound (e1) can be prepared by a method described in WO 2018/053267 or a similar method, or can be obtained as a marketed product.

(Step 1)

Compound (e2) can be prepared from Compound (c1) and Compound (e1) by a method described in *Organic Letters,* 21(7): 2081-2084 (2019), WO 2014/145051, or a similar method.

(Step 2)

Compound (e3) can be prepared from Compound (e2) by a method described in WO 2004/024730, or a similar method.

(Step 3)

Compound (e4) can be prepared from Compound (e3) by the method described in step 3 of preparation process C or a similar method.

(Step 4)

Compound (e5) can be prepared from Compound (e3) by the method described in step 4 of preparation process C or a similar method.

(Step 5)

Compound (e4) can be prepared from Compound (e5) by the method described in step 5 of preparation process C or a similar method.

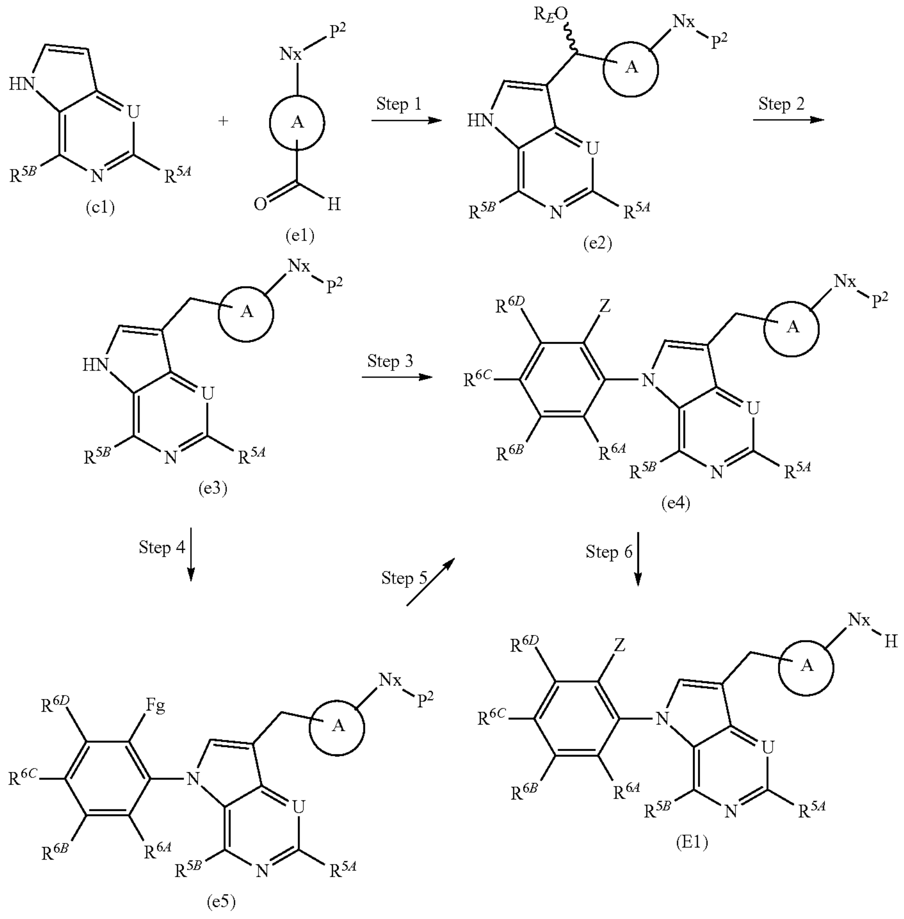

wherein $R^{5A}$, $R^{5B}$, $R^{6A}$, $R^{6B}$, $R^{6C}$, $R^{6D}$, U, Ring A, and Z are as defined in Item 1; Nx is as defined in Preparation Process A; Fg and $P^2$ are as defined in Preparation Process C; and $R_E$ is methyl or ethyl.

(Step 6)

Compound (E1) can be prepared by removing protecting group $P^2$ from compound (e4). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process F

In the compound of formula (a1), the compound of formula (F1) can be prepared, for example, by the following process:

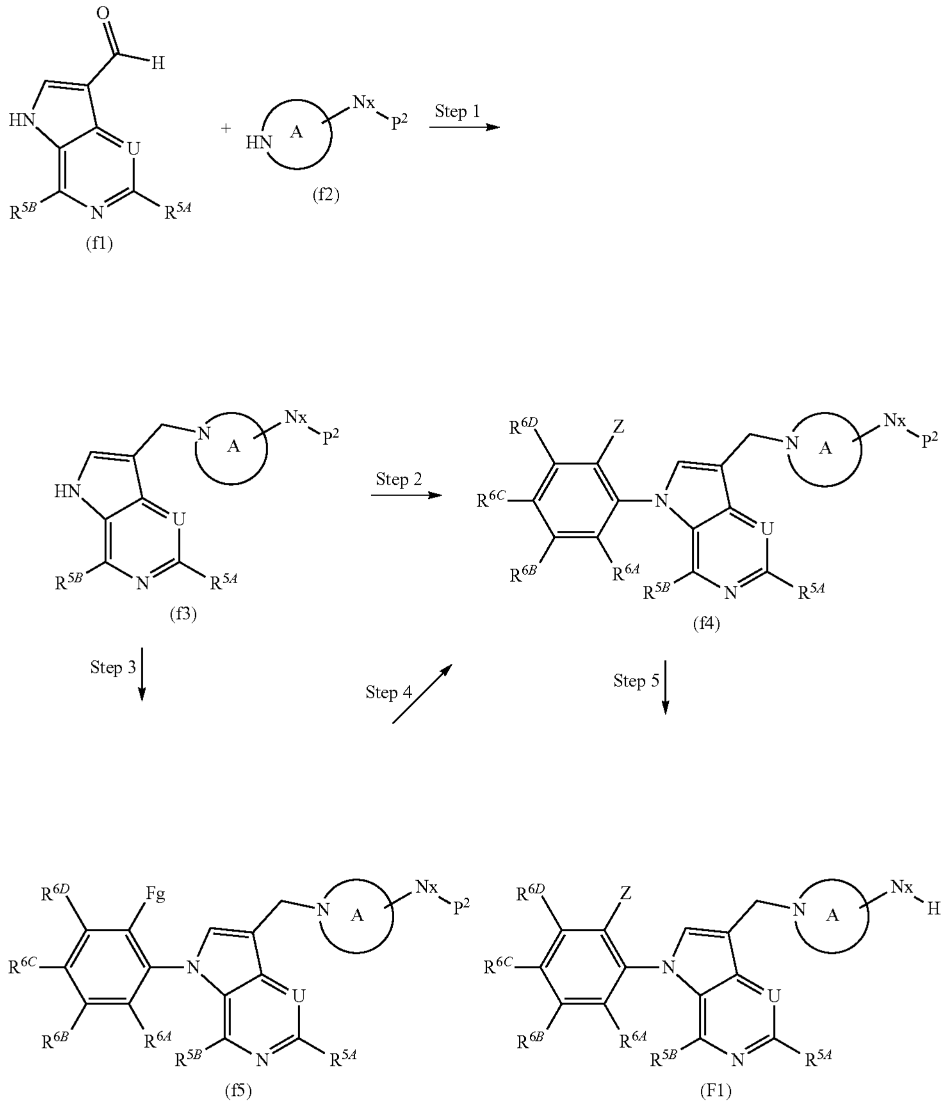

(f1) (f2) (f3) (f4) (f5) (F1)

wherein $R^{5A}$, $R^{5B}$, $R^{6A}$, $R^{6B}$, $R^{6C}$, $R^{6D}$, U, Ring A, and Z are as defined in Item 1; Nx is as defined in Preparation Process A; and Fg and $P^2$ are as defined in Preparation Process C.

Compound (f1) and Compound (f2) are commercially available.

(Step 1)

Compound (f3) can be prepared from Compound (f1) and Compound (f2) by the method described in step 1 of preparation process B or a similar method.

(Step 2)

Compound (f4) can be prepared from Compound (f3) by the method described in step 3 of preparation process C or a similar method.

(Step 3)

Compound (f5) can be prepared from Compound (f3) by the method described in step 4 of preparation process C or a similar method.

(Step 4)

Compound (f4) can be prepared from Compound (f5) by the method described in step 5 of preparation process C or a similar method.

(Step 5)

Compound (F1) can be prepared by removing protecting group $P^2$ from compound (f4). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process G

In the compound of formula (a1), the compound of formula (G1) can be prepared, for example, by the following process:

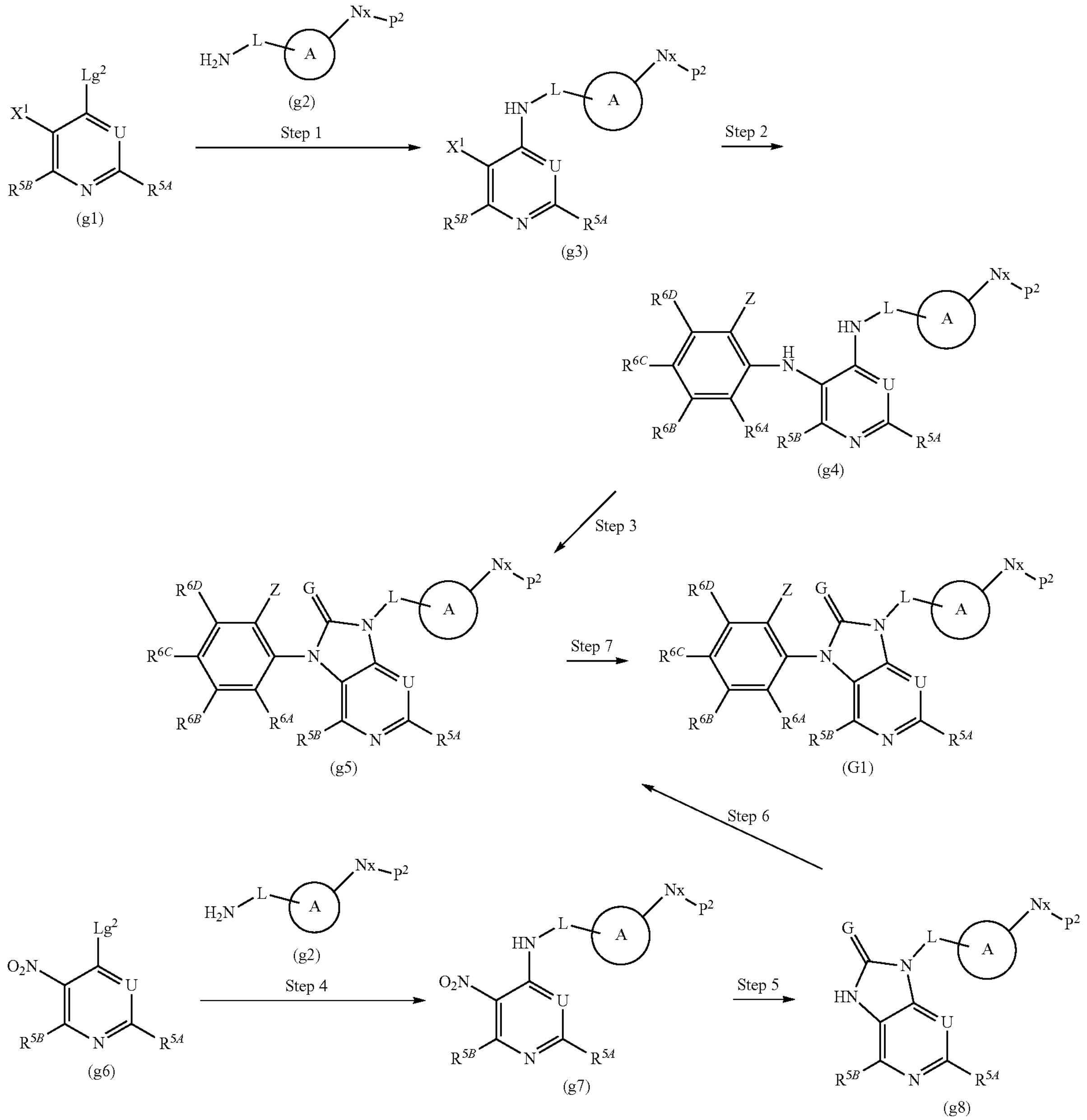

wherein $R^{5A}$, $R^{5B}$, $R^{6A}$, $R^{6B}$, $R^{6C}$, $R^{6D}$, U, L, Ring A, and Z are as defined in Item 1; Nx is as defined in Preparation Process A; Fg and $P^2$ are as defined in Preparation Process C; G is oxygen atom or sulfur atom; $X^1$ is as defined in Preparation Process U; $Lg^2$ is a leaving group which includes, for example, halogen, nitro, methanesulfonyloxy, p-toluenesulfonyloxy, trifluoromethanesulfonyloxy, phenoxy, pentafluorophenoxy, nitrophenoxy, and the like.

Compound (g1) and Compound (g2) are commercially available.

(Step 1)

Compound (g3) can be prepared from Compound (g1) and Compound (g2) by a method described in WO 2010/149956, WO 2009/044162, or a similar method.

(Step 2)

Compound (g4) can be prepared from Compound (g3) by the method described in step 3 of preparation process C or a similar method.

(Step 3)

Compound (g5) can be prepared from Compound (g4) by a method described in *Bioorganic & Medicinal Chemistry Letters,* 18(23): 6067-6070 (2008), *Bioorganic & Medicinal Chemistry,* 19(12): 3669-3677 (2011), *Bioorganic & Medicinal Chemistry,* 18(21): 7357-7364 (2070), WO 2018/021447, or a similar method.

(Step 4)

Compound (g7) can be prepared from Compound (g6) and Compound (g2) by a method described in *Bioorganic & Medicinal Chemistry Letters,* 18(18): 5023-5026 (2008), *Bioorganic & Medicinal Chemistry Letters,* 19(15): 4406-4409 (2009), *Journal of Medicinal Chemistry,* 57(17), 7325-7341 (2014), WO 2002/050062, or a similar method.

(Step 5)

Compound (g8) can be prepared from Compound (g7) by a method described in *ACS Medicinal Chemistry Letters,* 8(3): 344-349 (2017), *Tetrahedron Letters,* 52(44): 5728-5732 (2011), WO 2001/095910, *Journal of Medicinal Chemistry,* 60(14): 6289-6304 (2017), *European Journal of Medicinal Chemistry,* 156, 240-251 (2018), or a similar method.

(Step 6)

Compound (g5) can be prepared from Compound (g8) by the method described in step 3 of preparation process C or a similar method.

(Step 7)

Compound (G1) can be prepared by removing protecting group $P^2$ from compound (g5). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process H

In the compound of formula (a1), the compound of formula (H1) can be prepared, for example, by the following process:

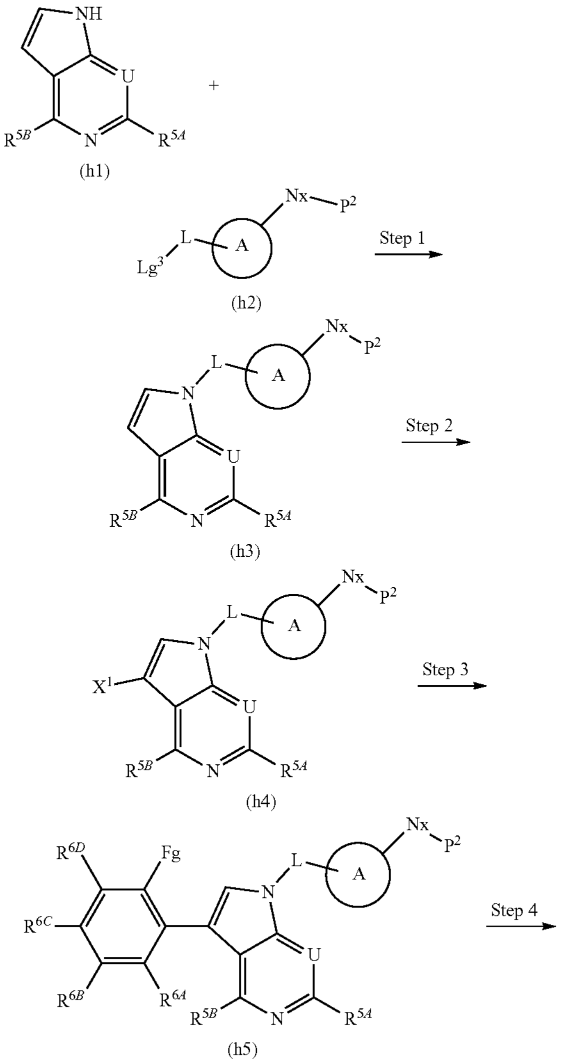

(h1) (h2) (h3) (h4) (h5)

-continued

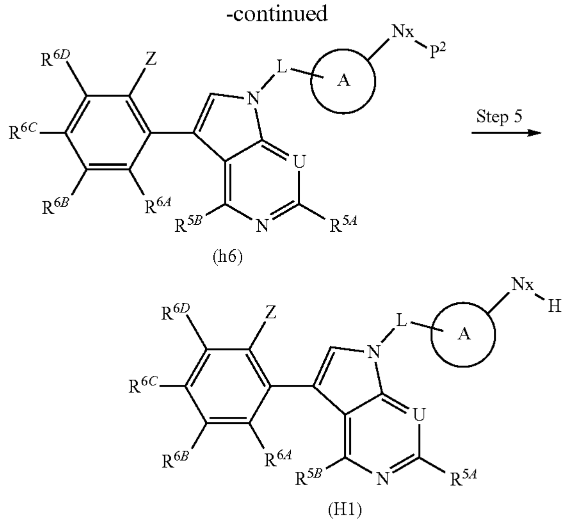

(h6) (H1)

wherein $R^{5A}$, $R^{5B}$, $R^{6A}$, $R^{6B}$, $R^{6C}$, $R^{6D}$, U, L, Ring A, and Z are as defined in Item 1; Nx is as defined in Preparation Process A; Fg and $P^2$ are as defined in Preparation Process C; $X^1$ is as defined in Preparation Process D; $Lg^3$ is a leaving group which includes, for example, halogen, methanesulfonyloxy, p-toluenesulfonyloxy, trifluoromethanesulfonyloxy, and the like.

Compound (h1) and Compound (h2) are commercially available.

(Step 1)

Compound (h3) can be prepared from Compound (h1) and Compound (h2) by the method described in *Organic Letters,* 20(24): 7898-7901 (2018), WO 2011/097079, or a similar method.

(Step 2)

Compound (h4) can be prepared from Compound (h3) by the method described in step 4 of preparation process D or a similar method.

(Step 3)

Compound (h5) can be prepared from Compound (h4) by a method described in *Journal of Organic Chemistry,* 83(16): 8926-8935 (2018), WO 2013/180265, or a similar method.

(Step 4)

Compound (h6) can be prepared from Compound (h5) by the method described in step 5 of preparation process C or a similar method.

(Step 5)

Compound (H1) can be prepared by removing protecting group $P^2$ from compound (h6). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process I

In the compound of formula (a1), the compound of formula (I1) can be prepared, for example, by the following process:

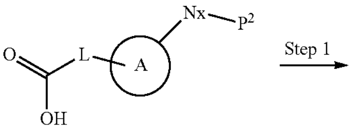

(i1)

-continued

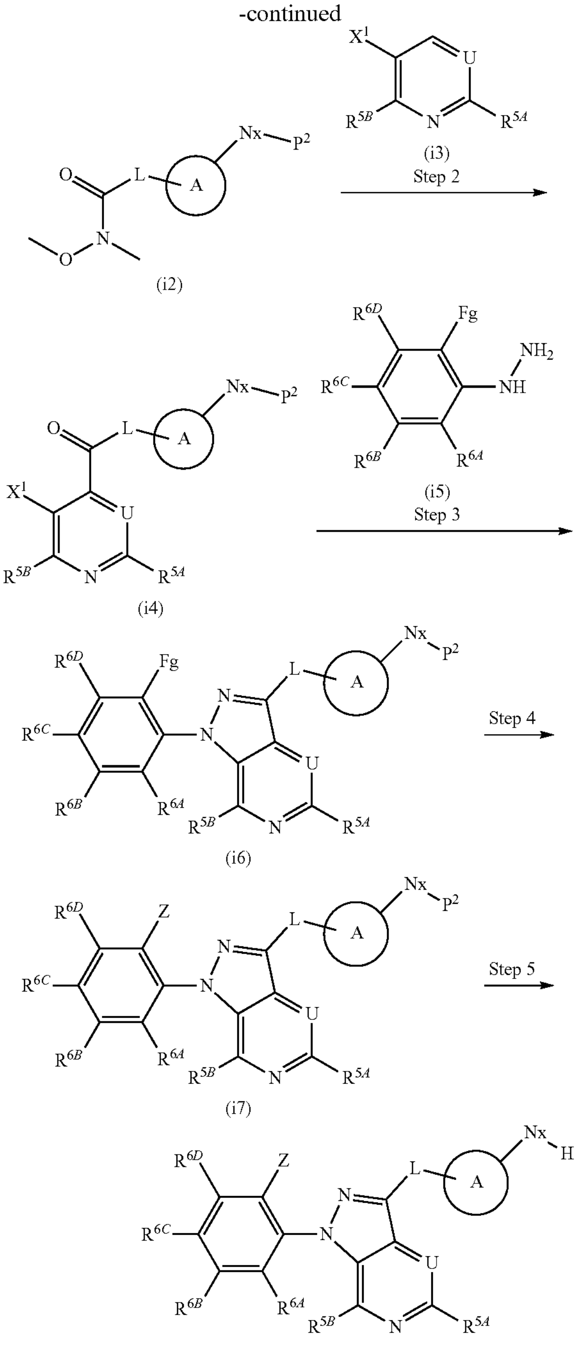

(i2) (i3) (i4) (i5) (i6) (i7) (I1)

wherein $R^{5A}$, $R^{5B}$, $R^{6A}$, $R^{6B}$, $R^{6C}$, $R^{6D}$, U, L, Ring A, and Z are as defined in Item 1; Nx is as defined in Preparation Process A; Fg and $P^2$ are as defined in Preparation Process C; and $X^1$ is as defined in Preparation Process D.

Compound (i1), Compound (i3) and Compound (i5) are commercially available.

(Step 1)

Compound (i2) can be prepared from Compound (i1) by a known method described in *Bioorganic & Medicinal Chemistry Letters,* 3(4): 753-756 (1993), *Bioorganic & Medicinal Chemistry Letters,* 14(23): 5937-5941 (2004), or a similar method.

(Step 2)

Compound (i4) can be prepared from Compound (i2) and Compound (i3) by a known method described in *Tetrahedron,* 39(12): 2009-2021 (1963), WO 2017/114351, or a similar method.

(Step 3)

Compound (i6) can be prepared from Compound (i4) and Compound (i5) by a known method described in WO 2010/036632, WO 2011/113798, WO 2005/073232, or a similar method.

(Step 4)

Compound (i7) can be prepared from Compound (i6) by the method described in step 5 of preparation process C or a similar method.

(Step 5)

Compound (I1) can be prepared by removing protecting group $P^2$ from compound (i7). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process J

In the compound of formula (f2), the compound of formula (J1) can be prepared, for example, by the following process:

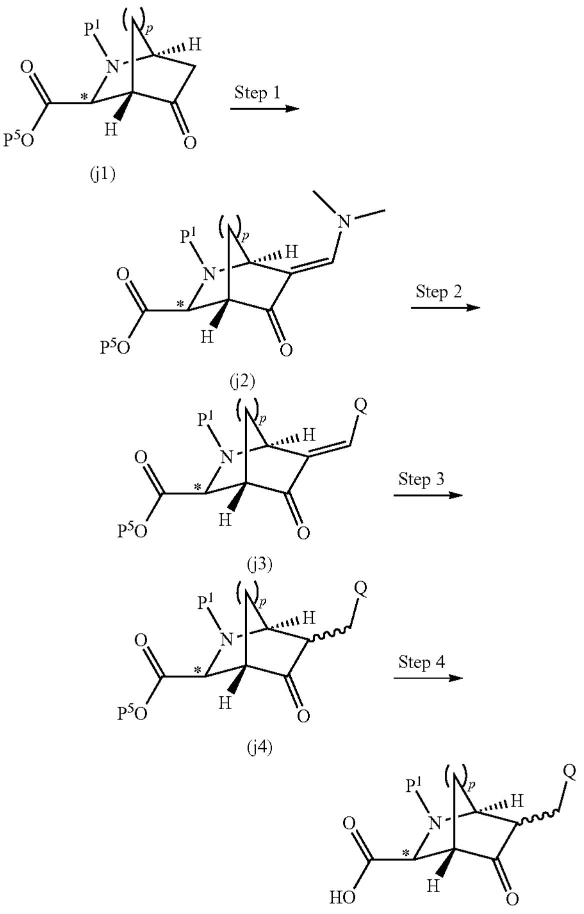

(j1) (j2) (j3) (j4) (J1)

wherein p and Q are as defined in Item 1; $P^1$ is as defined in Preparation Process A; $P^5$ is a carboxyl-protecting group which includes, for example, carboxyl-protecting groups described in Theodora W. Greene, Peter G. M. Wuts "*Pro-*

*tective Groups in Organic Synthesis*", John Wiley & Sons, Inc., (1999), and the like; and the stereochemistry of the carbon with * is not inverted during reactions.

Compound (j1) can be prepared by a method described in JP 2007-510619 A, *J. Chem. Soc., Chem. Commun.,* 1599-1601 (1988), *Tetrahedron Letters,* 43: 5957-5960 (2002), *Tetrahedron Asymmetry,* 2: 1263-1282 (1991), *Tetrahedron Asymmetry,* 27: 1062-1068 (2016), Larock R. C., "*Comprehensive Organic Transformation* 2nd Edition", John Wiley & Sons, Inc., (1989) or a similar method, or can be obtained as a marketed product.

(Step 1)

Compound (j2) can be prepared from Compound (j1) by a known method described in *Tetrahedron Letters,* 27: 2567-2570 (1986), *Synthesis,* 12: 1930-1935 (2011), *Bioorganic & Medicinal Chemistry Letters,* 23: 4493-4500 (2013), *European Journal of Organic Chemistry,* 10: 2485-2490 (1999), or a similar method.

(Step 2)

Compound (j3) can be prepared from Compound (j2) by a known method described in *Synthetic Communications,* 28: 1743-1753 (1998), *Chemistry Letters,* 6: 875-878 (1983), *Journal of Organic Chemistry,* 28: 6-16 (1963), or a similar method.

(Step 3)

Compound (j4) can be prepared from Compound (j3) by a known method described in *Tetrahedron Letters,* 23: 477-480 (1982), *Synlett,* 443-444 (1995), *Synlett,* 96-98 (1999), *Tetrahedron,* 56: 2779-2788 (2000), or a similar method.

(Step 4)

Compound (J1) can be prepared by removing protecting group $P^5$ from compound (j4). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process K

In the compound of formula (f2), the compound of formula (K1) can be prepared, for example, by the following process:

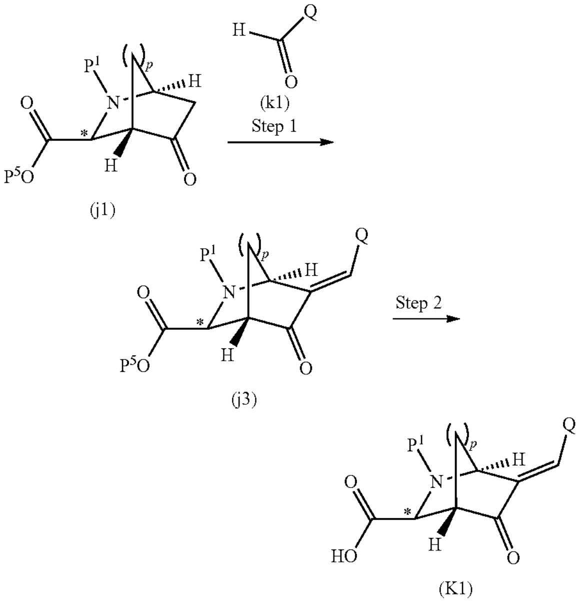

(j1) (k1) (j3) (K1)

wherein p and Q are as defined in Item 1; $P^1$ is as defined in Preparation Process A; $P^5$ is as defined in Preparation Process J; and the stereochemistry of the carbon with * is not inverted during reactions.

Compound (k1) is commercially available.

(Step 1)

Compound (j3) can be prepared from Compound (j1) and Compound (k1) by a known method described in *Journal of the American Chemical Society,* 126: 14206-14216 (2004), *Synthetic Communications,* 20: 839-847 (1990), *Synthesis,* 23: 3821-3826 (2011), *Advanced Synthesis & Catalysis,* 352: 153-162 (2010), or a similar method.

(Step 2)

Compound (K1) can be prepared by removing protecting group $P^5$ from compound (j3). The present step can be carried out, for example, by a method described in Theodora W. Greene, Peter G. M. Wuts, "*Protective Groups in Organic Synthesis*", John Wiley & Sons, Inc., (1999), or a similar method.

Preparation Process L

In the compound of formula (f2), the compound of formula (L1) can be prepared, for example, by the following process:

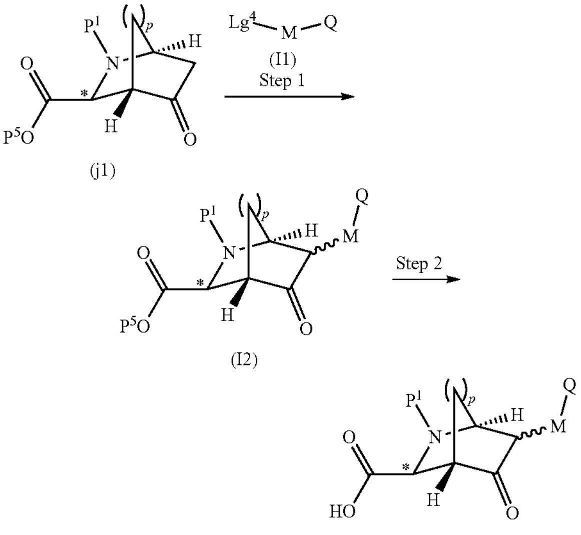

(j1) (l1) (l2) (L1)

wherein p, M, and Q are as defined in Item 1; $Lg^4$ is a leaving group; $P^1$ is as defined in Preparation Process A; $P^5$ is as defined in Preparation Process J; wherein $Lg^4$ includes, for example, halogen, methanesulfonyloxy, p-toluenesulfonyloxy, trifluoromethanesulfonyloxy, phenoxy, trifluorophenoxy, tetrafluorophenoxy, pentafluorophenoxy, nitrophenoxy, and the like; and the stereochemistry of the carbon with * is not inverted during reactions.

Compound (l1) is commercially available.

(Step 1)

Compound (l2) can be prepared from Compound (j1) and Compound (l1) by a method described in *Journal of the American Chemical Society,* 132: 1236-1237 (2010), *Journal of Medicinal Chemistry,* 49: 4409-4424 (2006), *Advanced Synthesis & Catalysis,* 357: 2803-2808 (2015), *Tetrahedron Letters,* 47(19): 3233-3237 (2006), *Angewandte Chemie, International Edition,* 44(34): 5516-5519 (2005), or a similar method.

(Step 2)

Compound (L1) can be prepared by removing protecting group $P^5$ from compound (12). The present step can be carried out, for example, by a method described in Theodora W. Greene, Peter G. M. Wuts, "*Protective Groups in Organic Synthesis*", John Wiley & Sons, Inc., (1999), or a similar method.

In the above preparation processes, starting materials or intermediates which are not described for preparation processes can be obtained as marketed products, or can be prepared from marketed products by a method well-known to those skilled in the art.

In each reaction described above, protecting groups can be used as necessary, even if the use of protecting groups is not explicitly stated. For example, when any one or more functional groups other than reaction sites are converted to undesired forms under the reaction condition, or the process described above cannot be carried out properly without protecting groups, protecting groups can be used to protect groups other than reaction sites as necessary, and can be deprotected after the reaction is completed or a series of reactions have been carried out to obtain the desired compound.

As such protecting groups, for example, the groups described in T. W. Greene, and P. G. M. Wuts, "*Protective Groups in Organic Synthesis*", John Wiley & Sons, Inc., (1999), and the like may be used. Examples of amino-protecting groups include, for example, benzyloxycarbonyl, tert-butoxycarbonyl, acetyl, benzyl, and the like. Examples of hydroxy-protecting groups include, for example, trialkylsilyl such as trimethylsilyl and tert-butyldimethylsilyl, acetyl, benzyl, and the like.

The introduction and elimination of protecting groups can be carried out by a method commonly-used in synthetic organic chemistry (for example, see "Protective Groups in Organic Synthesis" described above), or a similar method.

In the present specification, protecting groups, condensing agents and the like may be described in an abbreviated form according to IUPAC-IUB (Biochemical nomenclature committee) commonly-used herein. It should be understood that the names of compounds used in the present specification do not necessarily follow the IUPAC nomenclature.

The intermediates or the desired compounds which are described in the above preparation processes can be transformed to other compounds which fall within the present invention by optionally converting their functional groups to other groups (for example, the conversion from amino, hydroxy, carbonyl, halogen atom, and the like, while protecting or deprotecting other functional groups as necessary). The conversion of functional groups can be carried out by a general method which are commonly used (see, for example, R. C. Larock, "*Comprehensive Organic Transformations*", John Wiley & Sons Inc. (3999)).

The intermediates and the desired compounds described above can be isolated and purified by a purification method commonly-used in organic synthetic chemistry (for example, neutralization, filtration, extraction, washing, drying, enrichment, recrystallization, various chromatography, and the like). In addition, intermediates may be used in next reaction without further purification.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and acceptable salts of drug substances are conventional non-toxic salts. The suitable salt includes, for example, acid addition salts such as organic acid salts (including acetate, trifluoroacetate, maleate, fumarate, citrate, tartrate, methanesulfonate, benzenesulfonate, formate, and p-toluenesulfonate) and inorganic acid salts (including hydrochloride, hydrobromide, hydroiodide, sulfate, nitrate, and phosphate); salts with amino acids (including arginine, aspartate, and glutamate); alkali metal salts (including sodium salts, and potassium salts); alkaline earth metal salts (including calcium salts, and magnesium salts); ammonium salts; organic base salts (including trimethylamine salts, triethylamine salts, pyridine salts, picolinate, dicyclohexylamine salts, and N,N'-dibenzylethylenediamine salts); and other salts which a person skilled in the art can optionally select.

In the present invention, the compound of formula (1) encompasses deuterated compounds in which any one or more $^1H$ in the compound of formula (1) are replaced with $^2H$ (D).

The present invention encompasses compounds of formula (1) or pharmaceutically acceptable salts thereof. The compound of the present invention may exist in a form of hydrate and/or solvate of various solvents, including ethanolate, and these hydrate and/or solvate are included in the compound of the present invention.

The compound of the present invention encompasses optical isomers based on an optically active center, atropisomers based on axial or planar chirality caused by restriction of intramolecular rotation, and all other isomers which can exist as stereoisomers, tautomers, and geometric isomers, and crystalline forms in various states, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize 2 kinds of diastereomers, which are resolved by fractional crystallization or a similar method through different physical properties.

If the compound of the present invention should be obtained as a pharmaceutically acceptable salt thereof, when the compound of formula (1) is obtained as a pharmaceutically acceptable salt, it may be purified without further reaction, and when it is obtained in a free form, it may be solved or suspended in an appropriate organic solvent and an acid or base may be added therein to form a salt by a common method.

In the present invention, the "agent used in combination" is an anticancer medicament which can be used in combination with the compound of the present invention or can be combined with the compound of the present invention in a pharmaceutical composition. The "combination drug" includes, for example, an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, an biological response modifier, a hormone preparation, an immune checkpoint inhibitor, an epigenetics-associated molecular inhibitor, a protein post-translational modification inhibitor, and other anticancer medicaments. Examples of the "combination drug" include, for example, azacytidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, aLezolizumab, mogamulizumab, alemtuzumab, ofatumumab, ipilimumab, ramucirumab, brentuximab vedotin, Gemtuzumab ozogamicin, inotuzumab ozogamicin, and the like.

The administration route of the compound of the present invention may be oral, parenteral, intrarectal, or ophthalmic administration, and the daily dose depends on the type of compounds, administration methods, the condition or age of patients, and the like. For example, in the case of oral administration, about 0.01 to 1000 mg, more preferably about 0.1 to 500 mg per kg body weight of a human or mammal can be usually administrated in one to several portions. In the case of parenteral administration such as intravenous injection, for example, about 0.01 mg to 300 mg, more preferably about 1 mg to 100 mg per kg body weight of a human or mammal can be usually administrated.

The compound of the present invention can be orally or parenterally administrated directly or as a suitable drug formulation. The dosage form includes, for example, a tablet, a capsule, a powder, a granule, a liquid, a suspension, an injection, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, mannitol, crystalline cellulose, low-substituted hydroxypropylcellulose, corn starch, partially-pregelatinized starch, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, talc, and the like.

EXAMPLES

The present invention is explained in more detail in the following by referring to Reference examples, Examples, and Tests; however, the technical scope of the present invention should not be limited thereto.

In the present specification, the abbreviations shown below may be used.

THF: tetrahydrofuran

TFA: trifluoroacetic acid

DMF: N,N-dimethylformamide

DMSO: dimethylsulfoxide

MeCN: acetonitrile

Me: methyl

Et: ethyl

Ph: phenyl

Bn: benzyl

Boc: tert-butoxycarbonyl

BINAP: 2,2'-bis(diphenylphosphino)-1,1'-binaphthyl $Pd_2(dba)_3$: tris(dibenzylideneacetone)dipalladium(0)

Ac: acetyl dppf: 1,1'-bis(diphenylphosphino)ferrocene

Xantphos: 4,5-bis(diphenylphosphino)-9,9-dimethylxanthene

Dess-Martin reagent: Dess-Martin periodinane (1,1,1-triacetoxy-1,1-dihydro-1,2-benziodoxol-3-(1H)-one)

Petasis reagent: bis(cyclopentadienyl)dimethyltitanium Bredereck reagent: tert-butoxy-bis(dimethylamino) methane HATU: 1-[bis(dimethylamino)methylene]-1H-1,2,3-triazolo[4,5-b]pyridinium 3-oxide hexafluorophosphate WSCI-HCl: 1-(3-dimethylaminopropyl)-3-ethylcarbodiimide hydrochloride HOBt: 1-hydroxybenzotriazole p-: paratert-: tertiary- NMR (Nuclear Magnetic Resonance) data used for identification of compounds were obtained with a JNM-ECS400 type nuclear magnetic resonance instrument (400 MHz) from JEOL Ltd.

The symbols used in NMR are defined as follows, s: singlet, d: doublet, dd: doublet of doublet, t: triplet, td: triplet of doublet, q: quartet, m: multiplet, br: broad, brs: broad singlet, brm: broad multiplet, and J: coupling constant.

Analytical conditions of LC/MS (Liquid Chromatography-Mass Spectrometry) used for identification of compounds are shown below. In observed mass spectrometry values [MS(m/z)], monoisotopic mass (exact mass consisting of only main isotope) is shown in $[M+H]^+$, $[M-H]^-$, or $[M+2H]^{2+}$, etc., and retention time is shown as Rt (min).

The analytical conditions of LC/MS:

Analytical Condition A

Detection apparatus: ACQUITY™ SQ detector (Waters Corporation)

HPLC: ACQUITY™ UPLC system

Column: Waters ACQUITY™ UPLC BEH C18 (1.7 μm, 2.1 mm×30 mm)

Solvent: A: 0.06% formic acid/$H_2O$, B: 0.06% formic acid/MeCN

Gradient condition: 0.0 to 1.3 minutes Linear gradient from

B 2% to B 96%

Flow rate: 0.8 mL/min
UV: 220 nm and 254 nm
Column temperature: 40° C.

Analytical Condition B

Detection apparatus: LCMS-2020 (Shimadzu Corporation)
HPLC: Nexera X2
Column: Phenomenex Kinetex™ 1.7 μm C18 (50 mm×2.1 mm)
Solvent: A: 0.05% TFA/$H_2O$, B: MeCN
Gradient condition: 0.0 to 1.7 minutes Linear gradient from B 10% to B 99%
Flow rate: 0.5 mL/min
UV: 220 nm and 254 nm
Column temperature: 40° C.

Reference Example 1 tert-Butyl 4-(1H-pyrrolo[2,3-c]pyridin-3-yl)-3,6-dihydropyridine-1(2H)-carboxylate

Reference Example 2 tert-Butyl 4-(1H-pyrrolo[2,3-c]pyridin-3-yl)piperidine-1-carboxylate

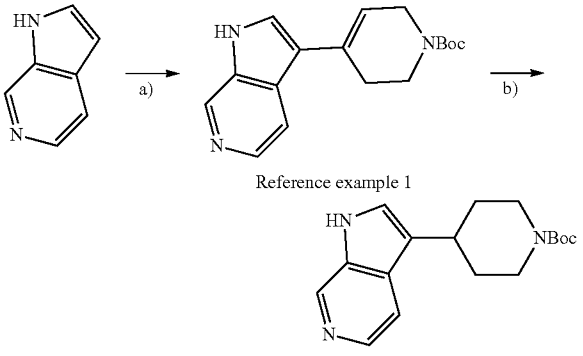

Reference example 2 a) Preparation of tert-butyl 4-(1H-pyrrolo[2,3-c]pyridin-3-yl)-3,6-dihydropyridine-1(2H)-carboxylate To a solution of 6-azaindole (3.9 g) and 1-(tert-butoxycarbonyl)-4-piperidone (6.6 g) in ethylene glycol (40 mL) was added potassium hydroxide (3.7 g), and the mixture was stirred at 100° C. for 10 hours. Water was added to the reaction solution, and the mixture was extracted with ethyl acetate. The organic layer was dried over anhydrous sodium sulfate and filtered, and the solvent of the filtrate was removed under reduced pressure. The residue was purified by silica gel column chromatography (chloroform/methanol) to yield the title compound (10.2 g).

$^1$H-NMR ($CDCl_3$) δ: 8.90 (1H, s), 8.21 (1H, d, J=5.5 Hz), 7.79 (1H, d, J=5.5 Hz), 7.46 (1H, s), 6.13 (1H, s), 4.17-4.08 (2H, m), 3.71-3.62 (2H, m), 2.58-2.50 (2H, m), 2.07 (1H, s).

b) Preparation of tert-butyl 4-(1H-pyrrolo[2,3-c]pyridin-3-yl)piperidine-1-carboxylate To a solution of tert-butyl 4-(1H-pyrrolo[2,3-c]pyridin-3-yl)-3,6-dihydropyridine-1(2H)-carboxylate (10.2 g) in methanol (100 mL) was added 10% palladium hydroxide/carbon (4.8 g), and the mixture was stirred at room temperature under ambient-pressured hydrogen atmosphere for 12 hours. The reaction mixture was filtered through Celite, and the filtrate was concentrated under reduced pressure to yield the title compound (9.5 g). LC-MS; $[M+H]^+$ 302.29/Rt (min) 0.652 (Analytical condition A)

Reference Examples 3-10

The following Reference examples 3 to 10 were prepared according to similar methods to Reference examples 1 and 2 by using each corresponding starting compound.

| Reference example | Structure | LC-MS; $[M + H]^+$ Rt (min) Analytical condition |
|---|---|---|
| 3 | 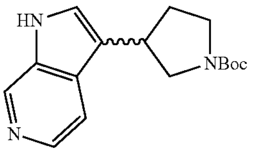 [SMILES: CC(C)(C)OC(=O)N1CCC(c2c[nH]c3cnccc23)C1] | 288.1/0.606/Analytical condition A |
| 4 | 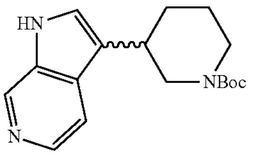 [SMILES: CC(C)(C)OC(=O)N1CCCC(c2c[nH]c3cnccc23)C1] | 302.0/0.723/Analytical condition A |
| 5 | 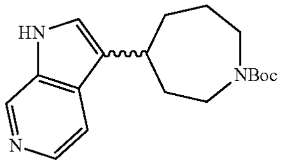 [SMILES: CC(C)(C)OC(=O)N1CCCC(c2c[nH]c3cnccc23)CC1] | 316.0/656/Analytical condition A |
| 6 | 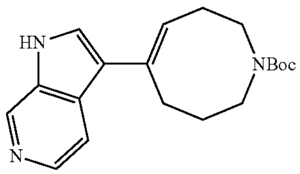 [SMILES: CC(C)(C)OC(=O)N1CC/C=C(/c2c[nH]c3cnccc23)CCC1] | 328.17/0.687/Analytical condition A |
| 7 | 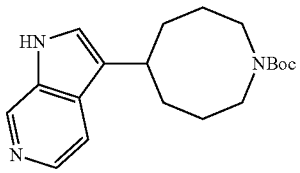 [SMILES: CC(C)(C)OC(=O)N1CCCC(c2c[nH]c3cnccc23)CCC1] | 330.17/0.792/Analytical condition A |
| 8 | 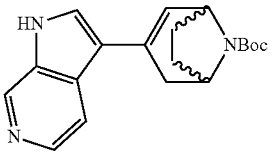 [SMILES: CC(C)(C)OC(=O)N1C2C=C(c3c[nH]c4cnccc34)CC1CC2] | 326.17/0.705/Analytical condition A |
| 9 | 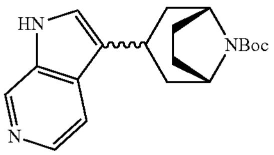 [SMILES: CC(C)(C)OC(=O)N1[C@@H]2CC[C@H]1CC(c1c[nH]c3cnccc13)C2] | 327.9/0.895/Analytical condition A |

-continued

| Reference example | Structure | LC-MS; [M + H]+ Rt (min) Analytical condition |
|---|---|---|
| 10 | 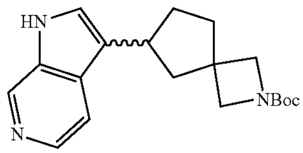 [SMILES: CC(C)(C)OC(=O)N1CC2(CCC(c3c[nH]c4cnccc34)C2)C1] | 328.0/0.885/Analytical condition A |

Reference Example 11 tert-Butyl 3-[(1H-pyrrolo[2,3-c]pyridin-3-yl)methyl]pyrrolidine-1-carboxylate

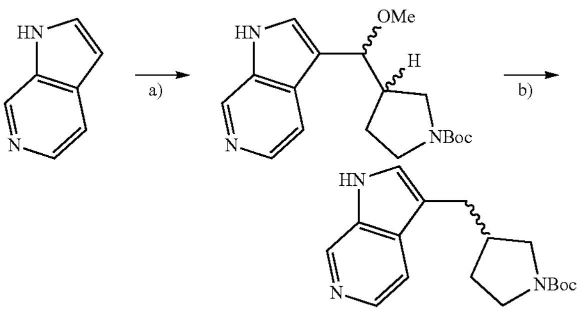

Reference example 11 a) Preparation of tert-butyl 3-[methoxy(1H-pyrrolo[2,3-c]pyridin-3-yl)methyl]pyrrolidine-1-carboxylate 6-Azaindole (2.00 g) was suspended in methanol (50.0 mL), and tert-butyl 3-formyl-pyrrolidine-1-carboxylate (6.75 g), 28% sodium methoxide in methanol (13.1 g) were added to the suspension at 0° C. The mixture was stirred at 80° C. for 18 hours. The reaction solution was left to stand until cool and then concentrated under reduced pressure. The residue was quenched with brine. The obtained aqueous solution was extracted with chloroform twice. The organic layer was washed with brine, dried over anhydrous sodium sulfate, and filtered, and the solvent of the filtrate was removed under reduced pressure. The residue was purified by silica gel column chromatography (chloroform/methanol) to yield the title compound (5.00 g).

LC-MS; $[M+H]^+$ 299.97/Rt (min) 0.808 (Analytical condition A)

b) Preparation of tert-butyl 3-[(1H-pyrrolo[2,3-c]pyridin-3-yl)methyl]pyrrolidine-1-carboxylate tert-Butyl 3-[methoxy(1H-pyrrolo[2,3-c]pyridin-3-yl)methyl]pyrrolidine-1-carboxylate (5.00 g) was dissolved in chloroform (50.0 mL), and triethylsilane (24.0 mL) and trifluoroacetic acid (12.0 mL) were added to the solution at 0° C. The mixture was stirred at 40° C. for 5 hours. The reaction solution was left to stand until cool and then concentrated under reduced pressure. The residue was dissolved in ethyl acetate (100 mL) and water (100 mL), and potassium carbonate (6.26 g) and di-tert-butyl dicarbonate (16.5 g) were added to the solution at 0° C. The mixture was stirred at room temperature for 5 hours. The reaction solution was quenched with brine. The obtained aqueous solution was extracted with ethyl acetate twice. The organic layer was washed with brine, dried over anhydrous sodium sulfate, and filtered, and the solvent of the filtrate was removed under reduced pressure. The residue was purified by amino silica gel column chromatography (chloroform/methanol) to yield the title compound (1.49 g). LC-MS; $[M+H]^+$ 301.97/Rt (min) 0.781 (Analytical condition A)

Reference Examples 12-13

The following Reference examples 12 and 13 were prepared according to a similar method to Reference example 11 by using each corresponding starting compound.

| Reference example | Structure | LC-MS; [M + H]+ Rt (min) Analytical condition |
|---|---|---|
| 12 | 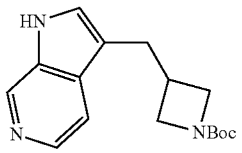 [SMILES: CC(C)(C)OC(=O)N1CC(Cc2c[nH]c3cnccc23)C1] | 287.97/0.614/Analytical condition A |
| 13 | 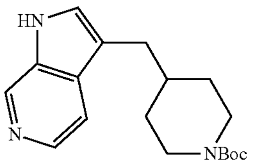 [SMILES: CC(C)(C)OC(=O)N1CCC(Cc2c[nH]c3cnccc23)CC1] | 316.3/0.642/Analytical condition A |

Reference Example 14 tert-Butyl 4-[(1H-pyrrolo[2,3-c]pyridin-3-yl)methyl]piperazine-1-carboxylate

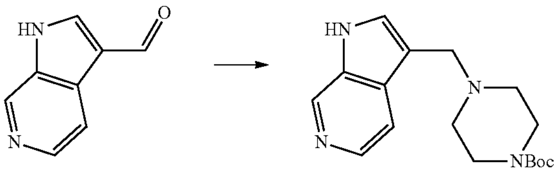
Reference example 14

1H-Pyrrolo[2,3-c]pyridine-3-carbaldehyde (500 mg) was dissolved in methylene chloride (15.0 mL), and tert-butyl 1-piperazine-carboxylate (1.59 g) and sodium triacetoxyborohydride (1.81 g) were added to the solution at 0° C. The mixture was stirred at room temperature for 5 hours. The reaction solution was quenched with saturated aqueous sodium bicarbonate. The obtained aqueous solution was extracted with chloroform twice. The organic layer was washed with brine, dried over anhydrous sodium sulfate, and filtered, and the solvent of the filtrate was removed under reduced pressure. The residue was purified by silica gel column chromatography (chloroform/methanol) to yield the title compound (500 mg).

LC-MS; $[M+H]^+$ 317.02/Rt (min) 0.567 (Analytical condition A)

Reference Example 15

The following Reference example 15 was prepared according to a similar method to Reference example 14 by using the corresponding starting compound.

| Reference example | Structure | LC-MS; $[M+H]^+$ Rt (min) Analytical condition |
|---|---|---|
| 15 | 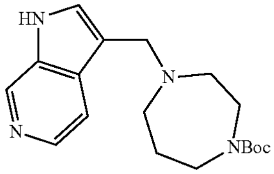 [SMILES: CC(C)(C)OC(=O)N1CCCN(Cc2c[nH]c3cnccc23)CC1] | 331.0/0.362/Analytical condition A |

Reference Example 16 tert-Butyl [(1S)-3-(1H-pyrrolo[2,3-c]pyridin-3-yl) cyclohexyl]carbamate

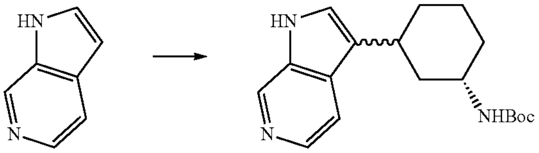

Reference example 16

6-Azaindole (2.00 g) and (3S)—N-Boc-aminocyclohexanone (3.97 g) were dissolved in ethylene glycol (5.00 mL), and potassium hydroxide (1.90 q) was added to the solution at 0° C. The mixture was stirred at 100° C. for 10 hours. The reaction solution was left to stand until cool and then quenched with brine. The obtained aqueous solution was extracted with chloroform twice. The organic layer was washed with brine, dried over anhydrous sodium sulfate, and filtered, and the solvent of the filtrate was removed under reduced pressure. The obtained redisue was dissolved in methanol (50.0 mL), and ammonium formate (10.6 g) and 10% palladium/carbon (1.01 g) were added to the solution. The mixture was heated under reflux for 3 hours. The reaction solution was left to stand until cool and then cooled to room temperature. The cooled reaction mixture was filtered with Celite, and brine was added to the filtrate. The obtained aqueous solution was extracted with chloroform twice. The organic layer was washed with brine, dried over anhydrous sodium sulfate, and filtered, and the solvent of the filtrate was removed under reduced pressure. The residue was purified by silica gel column chromatography (chloroform/methanol) to yield the title compound (2.00 g). LC-MS; $[M+H]^+$ 316.16/Rt (min) 0.667 (Analytical condition A)

Reference Example 17

5-Fluoro-2-[3-(piperidin-4-yl)-1H-pyrrolo[2,3-c] pyridin-1-yl]-N,N-di(propan-2-yl)benzamide

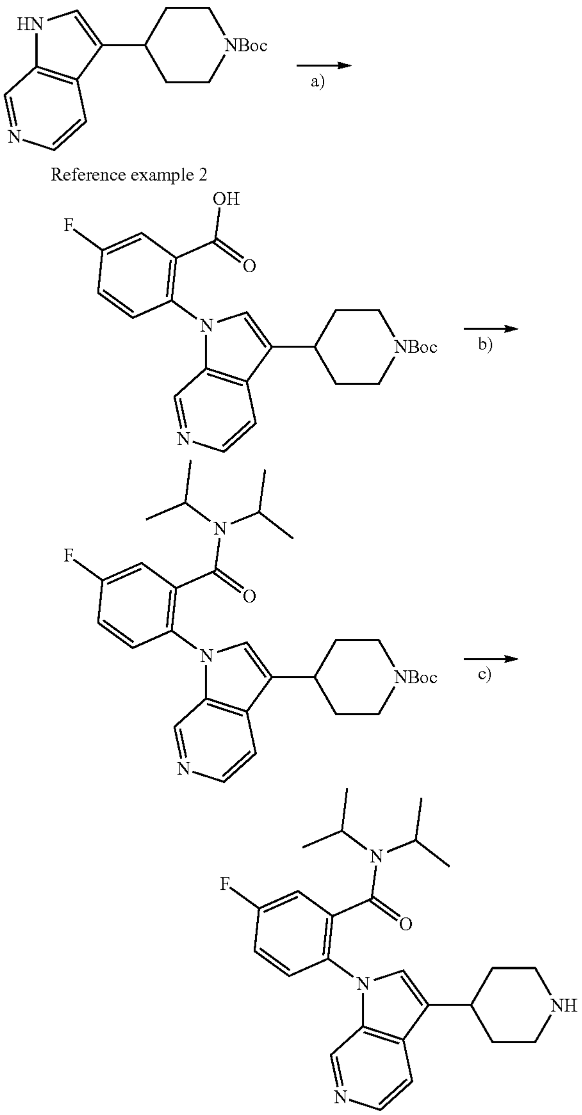

Reference example 17 a) Preparation of 2-{3-[1-(tert-butoxycarbonyl)piperidin-4-yl]-1H-pyrrolo[2,3-c]pyridin-1-yl}-5-fluorobenzoic acid A solution of tert-butyl 4-(1H-pyrrolo[2,3-c]pyridin-3-yl) piperidine-1-carboxylate (500 mg), 5-fluoro-2-iodobenzoic acid (662 mg), copper(I) iodide (95 mg), and 1,10-phenanthroline (90 mg) in DMF (100 mL) was stirred at 70° C. for 24 hours, and concentrated under reduced pressure to give the title compound as a crude product.

LC-MS; $[M+H]^+$ 440.4/Rt (min) 0.652 (Analytical condition A)

b) Preparation of tert-butyl 4-(1-{2-[di(propan-2-yl) carbamoyl]-4-fluorophenyl}-1H-pyrrolo[2,3-c]pyridin-3-yl)piperidine-1-carboxylate 2-{3-[1-(tert-Butoxycarbonyl)piperidin-4-yl]-1H-pyrrolo [2,3-c]pyridin-1-yl}-5-fluorobenzoic acid which was prepared in the above Spte a) as a crude product was suspended in chloroform (10 mL). To the suspension were added HATU (1.89 g), N,N-diisopropylamine (839 mg), and triethylamine (2.3 mL), and the mixture was stirred at room temperature for 2 hours. To the reaction solution was added saturated aqueous sodium bicarbonate, and the mixture was extracted with chloroform. The organic layer was dried over anhydrous magnesium sulfate and filtered, and the solvent of the filtrate was removed under reduced pressure. The residue was purified by silica gel column chromatography (chloroform/methanol) to yield the title compound.

LC-MS; $[M+H]^+$ 523.5/Rt (min) 0.807 (Analytical condition A)

c) Preparation of 5-fluoro-2-{3-(piperidin-4-yl)-1H-pyrrolo[2,3-c]pyridin-1-yl}-N,N-di(propan-2-yl) benzamide To a solution of tert-butyl 4-(1-{2-[di(propan-2-yl)carbamoyl]-4-fluorophenyl}-1H-pyrrolo[2,3-c]pyridin-3-yl)piperidine-1-carboxylate prepared in the above Step b) in methylene chloride (10 mL) was added trifluoroacetic acid (1.3 mL). The mixture was stirred at room temperature for 3 hours and then concentrated under reduced pressure. The residue was purified by amine silica gel column chromatography (chloroform/methanol) to yield the title compound (500 mg).

LC-MS; $[M+2H]^{2+}$ 212.2/Rt (min) 0.547 (Analytical condition A)

Reference Examples 18-37

The following Reference examples 18 to 37 were prepared according to similar methods to Reference examples 1 and 2 by using each corresponding starting compound.

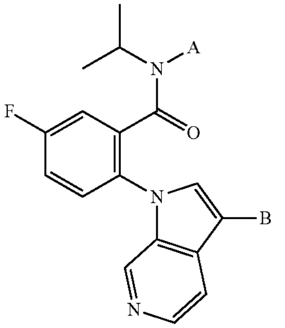

| Reference example | A | B | LC-MS; $[M + H]^+$ or $[M + 2H]^{2+}$ Rt (min) Analytical condition |
|---|---|---|---|
| 18 | Me | 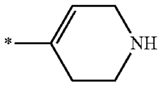 [SMILES: *C1=CCNCC1] | 197.2/0.392/Analytical condition A |
| 19 | i-Pr | 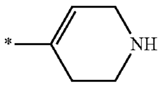 [SMILES: *C1=CCNCC1] | 211.26/0.481/Analytical condition A |

-continued

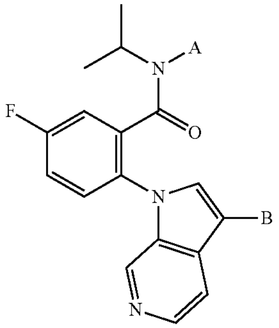

| Reference example | A | B | LC-MS; $[M + H]^+$ or $[M + 2H]^{2+}$ Rt (min) Analytical condition |
|---|---|---|---|
| 20 | Me | 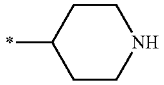 | 198.15/0.383/Analytical condition A |
| 21 | Me | 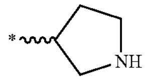 | 381.3/0.334/Analytical condition A |
| 22 | i-Pr | 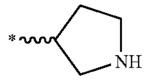 | 205.5/0.504/Analytical condition A |
| 23 | Me | 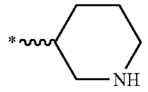 [SMILES: *C1CCCNC1] | 198.13/0.424/Analytical condition A |
| 24 | Me | 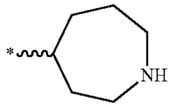 [SMILES: *C1CCCNCC1] | 409.0/0.339/Analytical condition A |
| 25 | i-Pr | 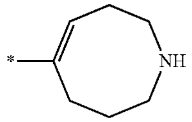 [SMILES: */C1=C/CCNCCC1] | 449.5/0.577/Analytical condition A |
| 26 | Me | 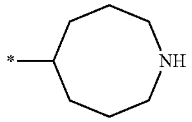 [SMILES: *C1CCCNCCC1] | 212.16/0.522/Analytical condition A |
| 27 | i-Pr | 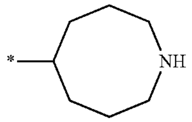 | 226.2/0.600/Analytical condition A |
| 28 | i-Pr | 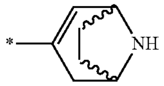 | 447.4/0.556/Analytical condition A |
| 29 | Me | 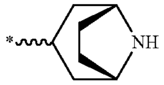 [SMILES: *C1C[C@H]2CC[C@@H](C1)N2] | 211.71/0.351/Analytical condition A |

-continued

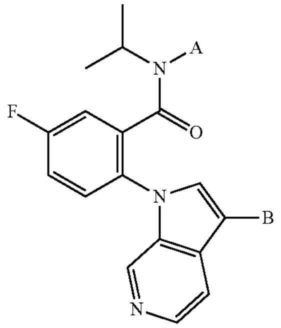

| Reference example | A | B | LC-MS; [M + H]$^+$ or [M + 2H]$^{2+}$ Rt (min) Analytical condition |
|---|---|---|---|
| 30 | i-Pr | 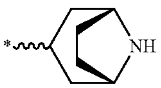 [SMILES: *C1C[C@H]2CC[C@@H](C1)N2] | 225.32/0.537/Analytical condition A |
| 31 | Me | 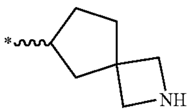 [SMILES: *C1CCC2(CNC2)C1] | 421.3/0.368/Analytical condition A |
| 32 | Me | 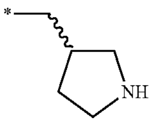 [SMILES: *CC1CCNC1] | 395.1/0.452/Analytical condition A |
| 33 | Me | 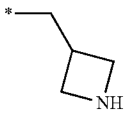 [SMILES: *CC1CNC1] | 191.1/0.376/Analytical condition A |
| 34 | Me | 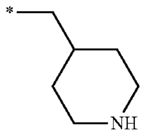 [SMILES: *CC1CCNCC1] | 205.13/0.390/Analytical condition A |
| 35 | Me | 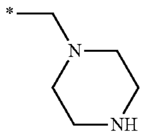 [SMILES: *CN1CCNCC1] | 205.88/0.351/Analytical condition A |
| 36 | Me | 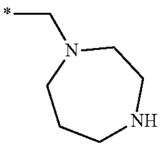 [SMILES: *CN1CCCNCC1] | 212.2/0.349/Analytical condition A |
| 37 | Me | 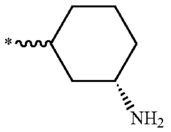 | 205.25/0.406/Analytical condition A |

Reference Example 38

(1S,3S,4S,5R)-2-(tert-Butoxycarbonyl)-5-hydroxy-2-azabicyclo[2.2.2]octane-3-carboxylic acid

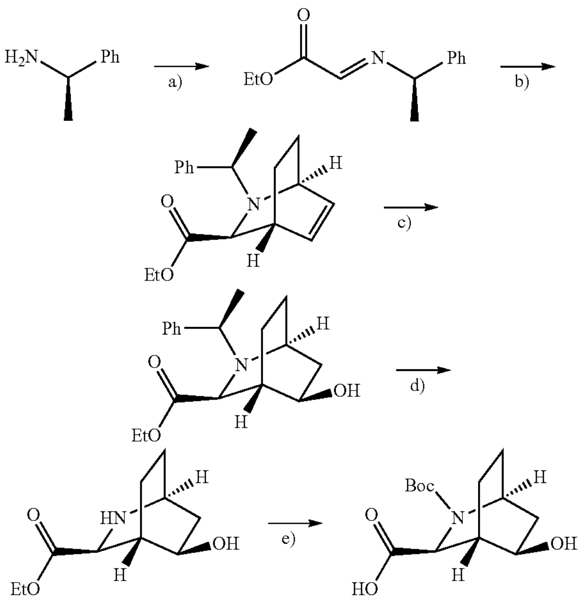

Reference example 38 a) Preparation of ethyl (2E)-{[(1R)-1-phenylethyl]imino}acetate

To (R)-1-phenylethylamine (63 mL) was added ethyl oxoacetate (100 mL), and the mixture was stirred at room temperature for an hour. The mixture was concentrated under reduced pressure to yield the title compound as a crude product. The obtained product was used in the next step without purification.

b) Preparation of ethyl (1S,3S,4R)-2-[(1R)-1-phenylethyl]-2-azabicyclo[2.2.2]oct-5-ene-3-carboxylate To a solution of ethyl (2E)-{[(1R)-1-phenylethyl]imino}acetate which was prepared in the above Spte a) as a crude product in dichloromethane (475 mL) was added molecular sieve 4A (powder, 10 g), and the reaction mixture was cooled to −70° C. To the reaction mixture were added dropwise trifluoroacetic acid (32 mL) and boron trifluoride diethyl ether complex (53 mL), and the mixture was stirred for 15 hours. Then 1,3-cyclohexadiene (42 mL) was added dropwise to the reaction mixture. The reaction mixture was warmed to room temperature and stirred overnight. To the reaction solution was added saturated aqueous sodium bicarbonate, and the mixture was extracted with ethyl acetate. The organic layer was washed with saturated aqueous sodium bicarbonate. The organic layer was dried over sodium sulfate and filtered, and the solvent of the filtrate was removed under reduced pressure. The residue was purified by silica gel column chromatography (hexane/ethyl acetate) to yield the title compound (59.4 g). LC-MS; [M+H]$^+$ 286.2/Rt (min) 0.53 (Analytical condition A)

c) Preparation of ethyl (1S,3S,4S,5R)-5-hydroxy-2-[(1R)-1-phenylethyl]-2-azabicyclo[2.2.2]octane-3-carboxylate To a solution of ethyl (1S,3S,4R)-2-[(1R)-1-phenylethyl]-2-azabicyclo[2.2.2]oct-5-ene-3-carboxylate (85.5 g) in THF (500 mL) was added dropwise 1.0 mol/L borane-THF complex (300 mL) at 0 to 5° C., and the mixture was stirred at room temperature overnight. To the reaction solution were added 3 mol/L aqueous sodium hydroxide (62 mL) and 30% aqueous hydrogen peroxide (62 mL) at ice temperature, and the reaction mixture was stirred for 30 minutes. Then, aqueous sodium thiosulfate was added to the reaction mixture, and the mixture was stirred for an hour. To the reaction solution was added ethyl acetate/chloroform, and the mixture was extracted. The organic layer was washed with brine. The organic layer was dried over sodium sulfate and filtered, and the solvent of the filtrate was removed under reduced pressure. The residue was purified by silica gel column chromatography (hexane/ethyl acetate) to yield the title compound (51.7 g) as a crude product.

LC-MS; $[M+H]^+$ 304.2/Rt (min) 0.53 (Analytical condition A)

d) Preparation of ethyl (1S,3S,4S,5R)-5-hydroxy-2-azabicyclo[2.2.2]octane-3-carboxylate To a solution of the crude product (51.7 g) prepared in the above Step c) in ethanol (500 mL) was added 10% palladium hydroxide (10.2 g), and the mixture was stirred at room temperature for 6 hours under pressured hydrogen atmosphere (0.3 to 0.4 MPa). The reaction mixture was filtered, and the filtrate was concentrated under reduced pressure. The residue was purified by silica gel column chromatography (chloroform/methanol) to yield the title compound, ethyl (1S,3S,4S,5R)-5-hydroxy-2-azabicyclo[2.2.2]octane-3-carboxylate (19.0 g). LC-MS; $[M+H]^+$ 200.2/Rt (min) 0.27 (Analytical condition A) e) Preparation of (1S,3S,4S,5R)-2-(tert-butoxycarbonyl)-5-hydroxy-2-azabicyclo[2.2.2]octane-3-carboxylic acid Reference Example 38

To a solution of ethyl (1S,3S,4S,5R)-5-hydroxy-2-azabicyclo[2.2.2]octane-3-carboxylate (10.48 g) in 1,4-dioxane (153 mL) was added 1 mol/L aqueous sodium hydroxide (238 mL), and the mixture was stirred at room temperature for an hour. Then, the reaction solution was cooled to 0° C., and di-tert-butyl dicarbonate (11.48 g) was added to the reaction solution. The reaction solution was stirred for an hour, and then acidified with 1 mol/L aqueous hydrochloric acid. Brine was added to the acidified solution, and the mixture was extracted with a mixture of 10% ethanol/chloroform. The organic layer was dried over sodium sulfate and filtered, and the solvent of the filtrate was removed under reduced pressure. The residue was washed with diisopropyl ether, collected on a filter, dried to yield the title compound (8.40 g).

$^1$H-NMR (DMSO-$D_6$) δ: 12.55 (1H, br s), 4.86 (1H, br s), 3.96-3.81 (3H, m), 2.09-1.69 (4H, m), 1.59-1.49 (1H, m), 1.36 (3H, s), 1.31 (6H, s), 1.29-1.17 (2H, m).

Reference Example 39

(1S,3S,4S,5R)-2-(tert-Butoxycarbonyl)-5-hydroxy-2-azabicyclo[2.2.1]heptane-3-carboxylic acid

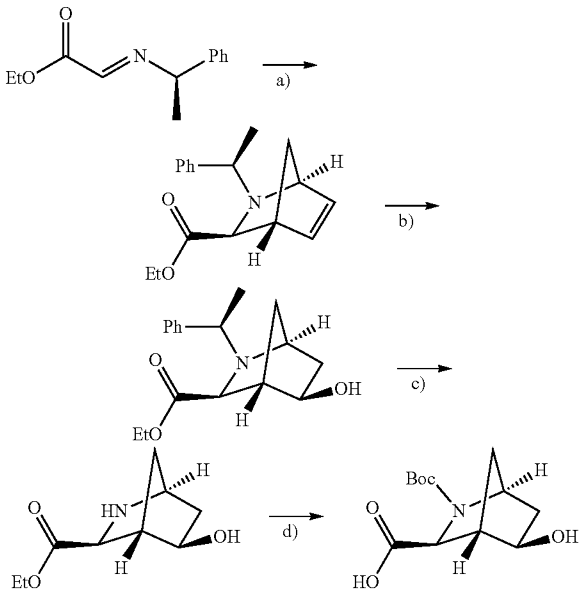

Reference example 39 a) Preparation of ethyl (1S,3S,4R)-2-[(1R)-1-phenylethyl]-2-azabicyclo[2.2.1]hept-5-ene-3-carboxylate The title compound (10.8 g) was prepared from ethyl (2E)-{[(1R)-1-phenylethyl]imino}acetate (12.0 g) and cyclopentadiene (4.92 mL) according to a similar method to Step b) in Reference example 38.

LC-MS; $[M+H]^+$ 272.2/Rt (min) 0.54 (Analytical condition A)

b) Preparation of ethyl (1S,3S,4S,5R)-5-hydroxy-2-[(1R)-1-phenylethyl]-2-azabicyclo[2.2.1]heptane-3-carboxylate The title compound (7.49 g) was prepared from ethyl (1S,3S,4R)-2-[(1R)-1-phenylethyl]-2-azabicyclo[2.2.1]hept-5-ene-3-carboxylate (10.8 g) according to a similar method to Step c in Reference example 38.

LC-MS; $[M+H]^+$ 290.2/Rt (min) 0.46 (Analytical condition A)

Preparation of ethyl (1S,3S,4S,5R)-5-hydroxy-2-azabicyclo[2.2.1]heptane-3-carboxylate The title compound (2.89 g) was prepared from ethyl (1S,3S,4S,5R)-5-hydroxy-2-[(1R)-1-phenylethyl]-2-azabicyclo[2.2.1]heptane-3-carboxylate (7.49 g) according to a similar method to Step d) in Reference example 38.

LC-MS; $[M+H]^+$ 186.1/Rt (min) 0.27 (Analytical condition A)

d) Preparation of (1S,3S,4S,5R)-2-(tert-butoxycarbonyl)-5-hydroxy-2-azabicyclo[2.2.1]heptane-3-carboxylic acid Reference Example 39

The title compound (980 mg) was prepared from ethyl (1S,3S,4S,5R)-5-hydroxy-2-azabicyclo[2.2.1]heptane-3-carboxylate (2.88 g) according to a similar method to Step e in Reference example 38.

$^{1}$H-NMR (DMSO-$D_6$) δ: 4.99 (1H, br s), 4.11-3.95 (1H, m), 3.95-3.82 (1H, m), 3.48-3.40 (1H, m), 2.41-2.31 (1H, m), 1.90-1.75 (1H, m), 1.69-1.49 (2H, m), 1.45-1.19 (10H, m).

Reference Example 40

3-Benzyl 2-tert-butyl (1S,3S,4S)-5-oxo-2-azabicyclo[2.2.2]octane-2,3-dicarboxylate

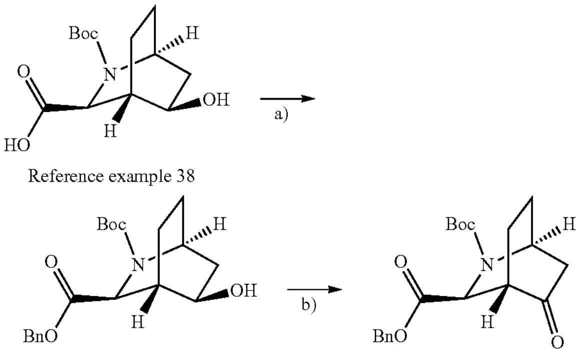

Reference example 38

Reference example 40 a) Preparation of 3-benzyl 2-tert-butyl (1S,3S,4S,5R)-5-hydroxy-2-azabicyclo[2.2.2]octane-2,3-dicarboxylate To a solution of (1S,3S,4S,5R)-2-(tert-butoxycarbonyl)-5-hydroxy-2-azabicyclo[2.2.2]octane-3-carboxylic acid (28.0 g) and potassium carbonate (28.5 g) in acetonitrile (300 mL) was added benzyl bromide (12.3 mL) at room temperature, and the mixture was stirred overnight. The reaction solution was concentrated under reduced pressure. To the obtained residue was added water, and the mixture was extracted with ethyl acetate. The organic layer was dried over sodium sulfate and filtered, and the solvent of the filtrate was removed under reduced pressure. The residue was purified by silica gel column chromatography (hexane/ethyl acetate) to yield the title compound (33.1 g).

LC-MS; $[M+H]^+$ 362.3/Rt (min) 0.95 (Analytical condition A)

b) Preparation of 3-benzyl 2-tert-butyl (1S,3S,4S)-5-oxo-2-azabicyclo[2.2.2]octane-2,3-dicarboxylate (Reference Example 40)

To a solution of 3-benzyl 2-tert-butyl (1S,3S,4S,5R)-5-hydroxy-2-azabicyclo[2.2.2]octane-2,3-dicarboxylate (33.0 g) in dichloromethane (400 mL) was added Dess-Martin reagent (46.5 g) at room temperature, and the mixture was stirred at room temperature overnight. To the reaction solution were added aqueous sodium thiosulfate and aqueous sodium bicarbonate, and the mixture was extracted with chloroform. The organic layer was dried over sodium sulfate and filtered, and the solvent of the filtrate was removed under reduced pressure. The residue was purified by silica gel column chromatography (hexane/ethyl acetate) to yield the title compound (33.8 g) as a crude product.

LC-MS; $[M+H]^+$ 360.2/Rt (min) 1.02 (Analytical condition A)

$^{1}$H-NMR ($CDCl_3$) δ: 7.38-7.28 (5H, m), 5.33-5.05 (2H, m), 4.66-4.42 (2H, m), 2.80-2.69 (1H, m), 2.59-2.45 (1H, m), 2.36-2.16 (2H, m), 1.82-1.62 (3H, m), 1.45 (2.5H, s), 1.31 (6.5H, s).

Reference Example 41

3-Benzyl 2-tert-butyl (1S,3S,4S)-5-oxo-2-azabicyclo[2.2.1]heptane-2,3-dicarboxylate

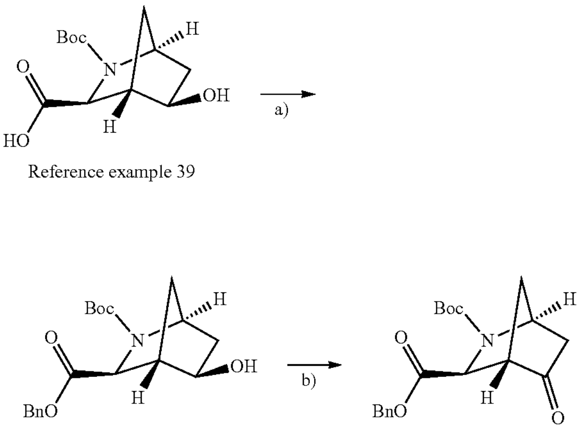

Reference example 39

Reference example 41 a) Preparation of 3-benzyl 2-tert-butyl (1S,3S,4S,5R)-5-hydroxy-2-azabicyclo[2.2.1]heptane-2,3-dicarboxylate The title compound (1.73 g) was prepared from (1S,3S,4S,5R)-2-(tert-butoxycarbonyl)-5-hydroxy-2-azabicyclo[2.2.1]heptane-3-carboxylic acid (1.5 g) according to a similar method to Step a) in Reference example 40.

LC-MS; $[M+H]^+$ 348.2/Rt (min) 0.92 (Analytical condition A)

b) Preparation of 3-benzyl 2-tert-butyl (1S,3S,4S)-5-oxo-2-azabicyclo[2.2.1]heptane-2,3-dicarboxylate (Reference Example 41)

The title compound (1.40 g) was prepared from 3-benzyl 2-tert-butyl (1S,3S,4S,5R)-5-hydroxy-2-azabicyclo[2.2.1]heptane-2,3-dicarboxylate (1.73 g) according to a similar method to Step b) in Reference example 40.

LC-MS; $[M+H]^+$ 346.2/Rt (min) 1.01 (Analytical condition A)

Reference Example 42

(1S,3S,4R)-2-(tert-Butoxycarbonyl)-5-methylidene-2-azabicyclo[2.2.2]octane-3-carboxylic acid

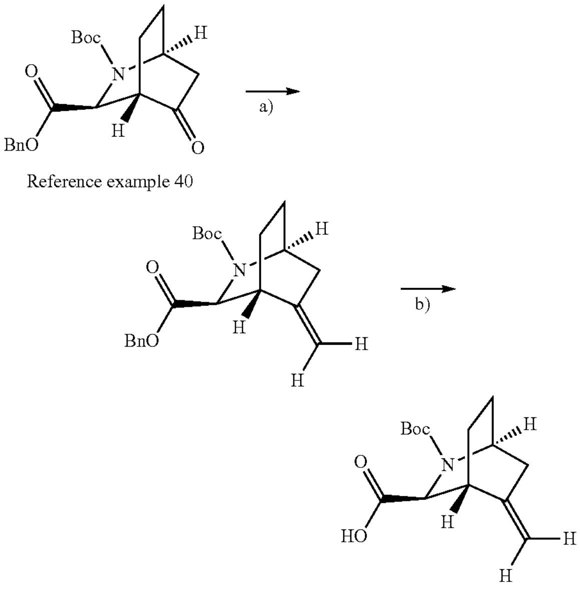

Reference example 40

Reference example 42 a) Preparation of 3-benzyl 2-tert-butyl (1S,3S,4R)-5-methylidene-2-azabicyclo[2.2.2]octane-2,3-dicarboxylate To a solution of 3-benzyl 2-tert-butyl (1S,3S,4S)-5-oxo-2-azabicyclo[2.2.2]octane-2,3-dicarboxylate (3.0 g) in THF (30 mL) was added Petasis reagent (5% THF/toluene solution, 35 g) at room temperature, and the mixture was stirred at 95° C. for 5 hours. The reaction mixture was cooled to room temperature, and Petasis reagent (5% THF/toluene solution, 10 g) was further added to the reaction mixture. The mixture was stirred under reflux at 130° C. The reaction mixture was left to stand until cool, and then diethyl ether was added to the reaction mixture. The precipitated orange solid was removed with filter, and the filtrate was concentrated. The residue was purified by silica gel column chromatography (hexane/ethyl acetate) to yield the title compound (1.9 g).

LC-MS; $[M+H]^+$ 358.0/Rt (min) 1.21 (Analytical condition A)

b) Preparation of (1S,3S,4R)-2-(tert-butoxycarbonyl)-5-methylidene-2-azabicyclo[2.2.2]octane-3-carboxylic acid Reference Example 42

To a solution of 3-benzyl 2-tert-butyl (1S,3S,4R)-5-methylidene-2-azabicyclo[2.2.2]octane-2,3-dicarboxylate (1.9 g) in methanol (60 mL) was added 5 mol/L aqueous sodium hydroxide (5.1 mL), and the mixture was stirred at 50° C. for 5 hours. The reaction solution was cooled to room temperature, then neutralized with 1 mol/L hydrochloric acid, and extracted with chloroform. The organic layer was dried over sodium sulfate, and filtered, and the solvent of the filtrate was removed under reduced pressure. The residue was purified by silica gel column chromatography (chloroform/methanol) to yield the title compound (0.99 g).

LC-MS; $[M+H]^+$ 268.0/Rt (min) 0.83 (Analytical condition A)

Reference Example 43

(1S,3S,4R)-2-(tert-Butoxycarbonyl)-5-methylidene-2-azabicyclo[2.2.1]heptane-3-carboxylic acid

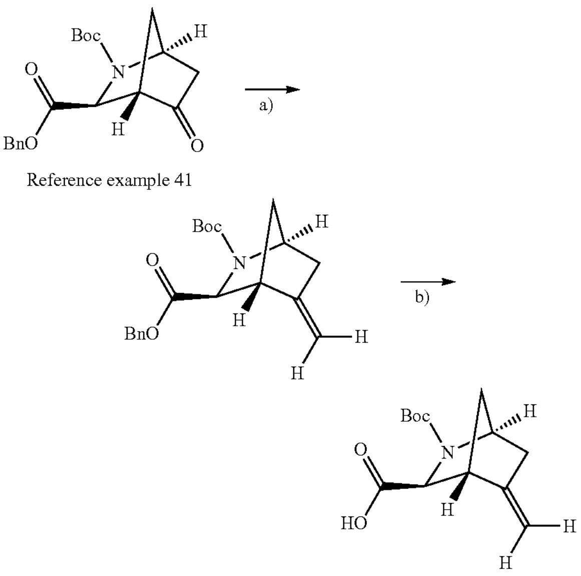

Reference example 41

Reference example 43 a) Preparation of 3-benzyl 2-tert-butyl (1S,3S,4R)-5-methylidene-2-azabicyclo[2.2.1]heptane-2,3-dicarboxylate The title compound (1.10 g) was prepared from 3-benzyl 2-tert-butyl (1S,3S,4S)-5-oxo-2-azabicyclo[2.2.1]heptane-2,3-dicarboxylate (1.40 g) according to a similar method to Step a) in Reference example 42.

LC-MS; $[M+H]^+$ 344.2/Rt (min) 1.18 (Analytical condition A)

b) Preparation of (1S,3S,4R)-2-(tert-butoxycarbonyl)-5-methylidene-2-azabicyclo[2.2.1]heptane-3-carboxylic acid Reference Example 43

The title compound (0.69 g) was prepared from 3-benzyl 2-tert-butyl (1S,3S,4R)-5-methylidene-2-azabicyclo[2.2.1]heptane-2,3-dicarboxylate (1.10 g) according to a similar method to Step b) in Reference example 42.

LC-MS; $[M+H]^+$ 254.3/Rt (min) 0.82 (Analytical condition A)

Reference Example 44

3-Benzyl 2-tert-butyl (1S,3S,4S,6E)-6-(cyclopropylmethylidene)-5-oxo-2-azabicyclo[2.2.2]octane-2,3-dicarboxylate

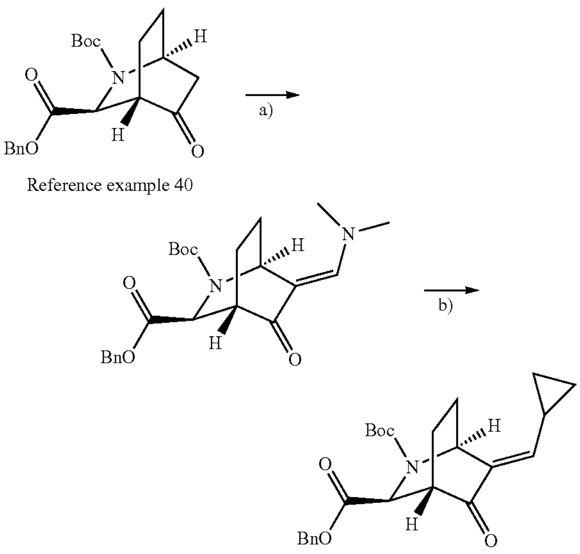

Reference example 44 a) Preparation of 3-benzyl 2-tert-butyl (1S,3S,4S,6E)-6-[(dimethylamino)methylidene]-5-oxo-2-azabicyclo[2.2.2]octane-2,3-dicarboxylate To a solution of 3-benzyl 2-tert-butyl (1S,3S,4S)-5-oxo-2-azabicyclo[2.2.2]octane-2,3-dicarboxylate (33.8 g) in N,N-dimethylformamide (180 mL) was added Bredereck reagent (32.8 g), and the mixture was stirred at 100° C. for 2 hours. The reaction solution was concentrated under reduced pressure, and the residue was purified by silica gel column chromatography (hexane/ethyl acetate) to yield the title compound (39.0 g) as a crude product.

LC-MS; $[M+H]^+$ 415.4/Rt (min) 0.95 (Analytical condition A)

b) Preparation of 3-benzyl 2-tert-butyl (1S,3S,4S,6E)-6-(cyclopropylmethylidene)-5-oxo-2-azabicyclo[2.2.2]octane-2,3-dicarboxylate (Reference Example 44)

A solution of 3-benzyl 2-tert-butyl (1S,3S,4S,6E)-6-[(dimethylamino)methylidene]-5-oxo-2-azabicyclo[2.2.2]octane-2,3-dicarboxylate (39.0 g) in tetrahydrofuran (300 mL) was cooled to 0° C., and cyclopropylmagnesium bromide (0.5 moL/L tetrahydrofuran solution, 245 mL) was added dropwise to the solution. The mixture was stirred at room temperature for 6 hours. Saturated aqueous ammonium chloride was added to the reaction solution, and the mixture was extracted with ethyl acetate. The organic layer was dried over sodium sulfate and filtered, and the solvent of the filtrate was removed under reduced pressure. The residue was purified by silica gel column chromatography (hexane/ethyl acetate) to yield the title compound (32.3 g).

LC-MS; $[M+H]^+$ 412.4/Rt (min) 1.16 (Analytical condition A)

$^1$H-NMR ($CDCl_3$) 7.39-7.27 (5H, m), 5.91 (1H, t, J=11.0 Hz), 5.38-5.04 (3H, m), 4.50-4.36 (1H, m), 2.90-2.76 (1H, m), 2.37-2.22 (1H, m), 1.82-1.59 (4H, m), 1.44 (3H, s), 1.31 (6H, s), 1.09-0.95 (2H, m), 0.73-0.58 (2H, m).

Reference Example 45

3-Benzyl 2-tert-butyl (1S,3S,4S,5R)-6-(cyclopropylmethyl)-5-hydroxy-2-azabicyclo[2.2.2]octane-2,3-dicarboxylate

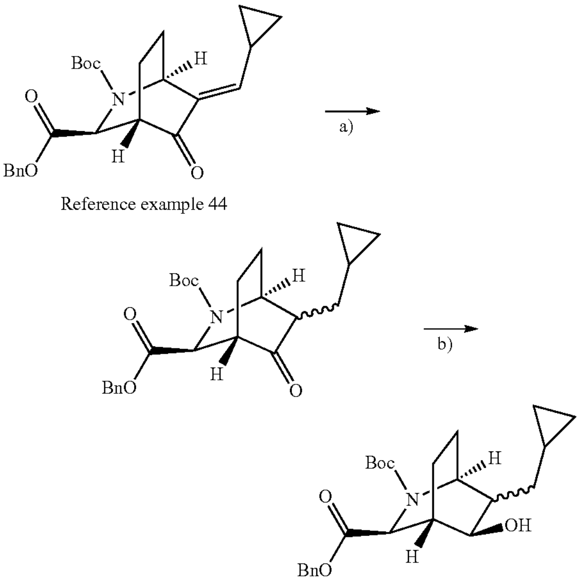

Reference example 45 a) Preparation of 3-benzyl 2-tert-butyl (1S,3S,4S)-6-(cyclopropylmethyl)-5-oxo-2-azabicyclo[2.2.2]octane-2,3-dicarboxylate To a solution of 3-benzyl 2-tert-butyl (1S,3S,4S,6E)-6-(cyclopropylmethylidene)-5-oxo-2-azabicyclo[2.2.2]octane-2,3-dicarboxylate (32.3 g) in tetrahydrofuran (300 mL) was added triphenylphosphine-copper(I) hydride hexamer (38.5 g), and the mixture was stirred at room temperature for 12 hours. The reaction solution was filtered with Celite, and the filtrate was concentrated under reduced pressure. The residue was purified by silica gel column chromatography (hexane/ethyl acetate) to yield the title compound (23.2 g) as a mixture of stereoisomers.

LC-MS; $[M+H]^+$ 414.1/Rt (min) 1.22 (Analytical condition A)

b) Preparation of 3-benzyl 2-tert-butyl (1S,3S,4S,5R)-6-(cyclopropylmethyl)-5-hydroxy-2-azabicyclo[2.2.2]octane-2,3-dicarboxylate (Reference Example 45)

A solution of 3-benzyl 2-tert-butyl (1S,3S,4S)-6-(cyclopropylmethyl)-5-oxo-2-azabicyclo[2.2.2]octane-2,3-dicarboxylate (23.2 g) in methanol (200 mL) was cooled to 0° C., and sodium borohydride (2.12 g) was added to the solution. The mixture was stirred for an hour. The reaction solution was concentrated under reduced pressure, and the residue was purified by silica gel column chromatography (hexane/ethyl acetate) to yield the title compound (10.2 g).

LC-MS; $[M+H]^+$ 416.1/Rt (min) 1.01 (Analytical condition A)

Reference Example 46

(1S,3S,4R,6S)-2-(tert-Butoxycarbonyl)-6-(cyclopropylmethyl)-2-azabicyclo[2.2.2]octane-3-carboxylic acid

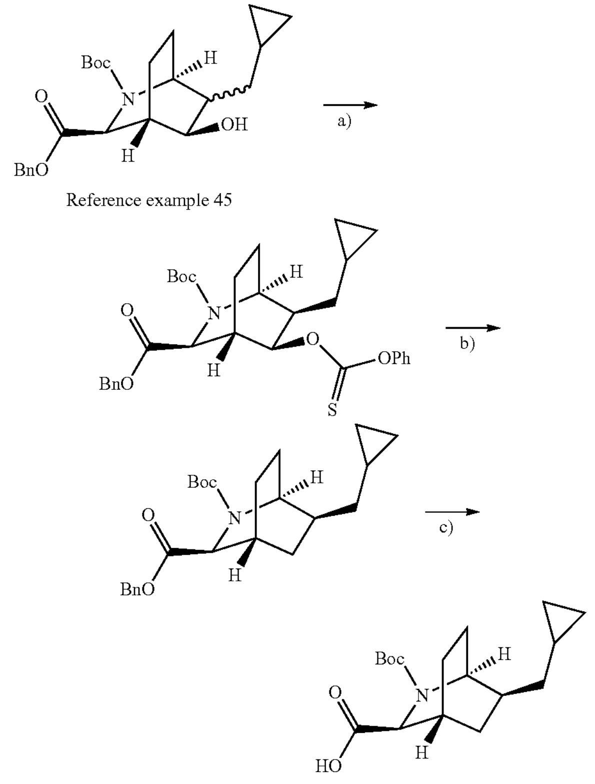

Reference example 45

Reference example 46 a) Preparation of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate A solution of 3-benzyl 2-tert-butyl (1S,3S,4S,5R)-6-(cyclopropylmethyl)-5-hydroxy-2-azabicyclo[2.2.2]octane-2,3-dicarboxylate (7.3 g) in acetonitrile (50 mL) was cooled to 0° C., and 4-(dimethylamino)pyridine (8.6 g) and phenyl chlorothionoformate (4.74 mL) were added to the solution. The mixture was stirred at 50° C. for 12 hours. The reaction solution was cooled to room temperature, and then brine was added to the cooled reaction solution. The mixture was extracted with ethyl acetate. The organic layer was dried over magnesium sulfate and filtered, and the solvent of the filtrate was removed under reduced pressure. The residue was purified by silica gel column chromatography (hexane/ethyl acetate) to yield 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate (1.80 g).

LC-MS; $[M+H]^+$ 552.2/Rt (min) 1.42 (Analytical condition A) b) Preparation of 3-benzyl 2-tert-butyl (1S,3S,4R,6S)-6-(cyclopropylmethyl)-2-azabicyclo[2.2.2]octane-2,3-dicarboxylate A solution of 3-benzyl 2-tert-butyl (1S,3S,4S,5R,6R)-6-(cyclopropylmethyl)-5-[(phenoxycarbonothioyl)oxy]-2-azabicyclo[2.2.2]octane-2,3-dicarboxylate (1.80 g) in toluene (50 mL) was cooled to 0° C., and tris(trimethylsilyl)silane (5.03 mL) and 2,2'-azobis(2-methylpropionitrile) (0.11 g) were added to the solution. The mixture was stirred at 50° C. for 5 hours. The reaction solution was cooled to room temperature, and then brine was added to the cooled reaction solution. The mixture was extracted with ethyl acetate. The organic layer was dried over magnesium sulfate and filtered, and the solvent of the filtrate was removed under reduced pressure. The residue was purified by silica gel column chromatography (hexane/ethyl acetate) to yield the title compound (0.80 g). LC-MS; $[M+H]^+$ 400.2/Rt (min) 1.38 (Analytical condition A)

c) Preparation of (1S,3S,4R,6S)-2-(tert-butoxycarbonyl)-6-(cyclopropylmethyl)-2-azabicyclo[2.2.2]octane-3-carboxylic acid (Reference Example 46)

The title compound (3.90 g) was prepared from 3-benzyl 2-tert-butyl (1S,3S,4R,6S)-6-(cyclopropylmethyl)-2-azabicyclo[2.2.2]octane-2,3-dicarboxylate (5.50 g) according to a similar method to Step b) in Reference example 42.

LC-MS; $[M+H]^+$ 310.2/Rt (min) 1.02 (Analytical condition A)

Reference Example 47 tert-Butyl (3S)-3-[4-(1-{2-[di(propan-2-yl)carbamoyl]-4-fluorophenyl}-1H-pyrrolo[2,3-c]pyridin-3-yl)piperidine-1-carbonyl]-2-azabicyclo[2.2.2]octane-2-carboxylate

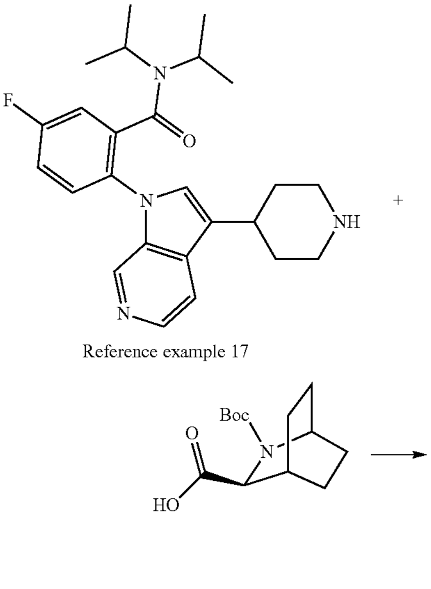

Reference example 17

-continued

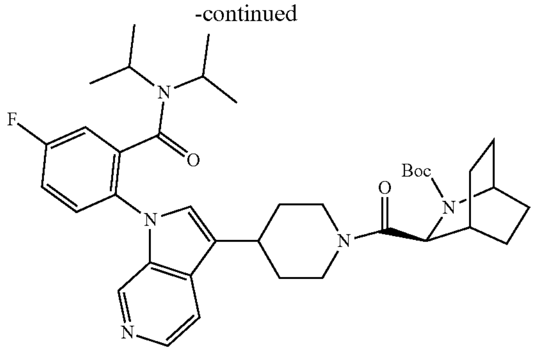

Reference example 47

To a solution of 5-fluoro-2-[3-(piperidin-4-yl)-1H-pyrrolo[2,3-c]pyridin-1-yl]-N,N-di(propan-2-yl)benzamide (150 mg) which was prepared in Reference example 17 in methylene chloride (5.00 mL) were added commercially-available (1S,3S,4R)-2-(tert-butoxycarbonyl)-2-azabicyclo[2.2.2]octane-3-carboxylic acid (109 mg), HATU (270 mg), and triethylamine (0.25 mL), and the mixture was stirred at room temperature for 2 hours. Water was added to the reaction solution, and the mixture was extracted with chloroform. The organic layer was dried over sodium sulfate and filtered, and the solvent of the filtrate was removed under reduced pressure. The residue was purified by silica gel column chromatography (hexane/ethyl acetate) to yield the title compound (245 mg).

LC-MS; $[M+H]^+$ 660.55/Rt (min) 0.970 (Analytical condition A)

Reference Examples 48-72

The following Reference examples 48 to 76 were prepared according to a similar method to Reference example 47 by using each corresponding starting compound.

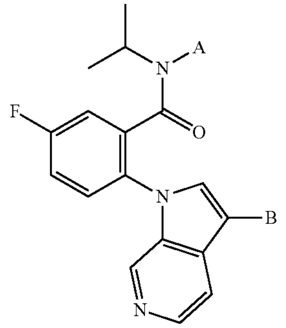

| Reference example | A | B | LC-MS; $[M + H]^+$ or $[M + 2H]^{2+}$ Rt (min) Analytical condition |
|---|---|---|---|
| 48 | Me | 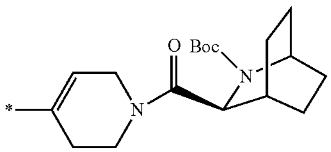 [SMILES: *C1=CCN(C(=O)[C@@H]2C3CCC(CC3)N2C(=O)OC(C)(C)C)CC1] | 630.49/0.829/Analytical condition A |
| 49 | i-Pr | 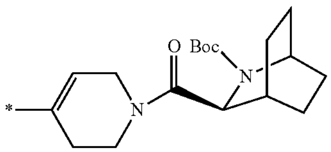 [SMILES: *C1=CCN(C(=O)[C@@H]2C3CCC(CC3)N2C(=O)OC(C)(C)C)CC1] | 658.55/0.816/Analytical condition A |
| 50 | Me | 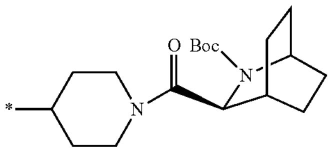 | 632.6/0.822/Analytical condition A |
| 51 | i-Pr | 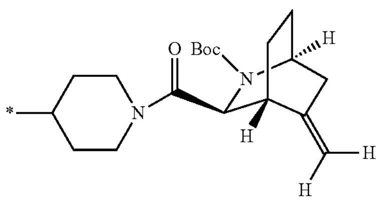 [SMILES: *C1CCN(C(=O)[C@@H]2[C@@H]3CC[C@@H](CC3=C)N2C(=O)OC(C)(C)C)CC1] | 672.5/0.922/Analytical condition A |

-continued
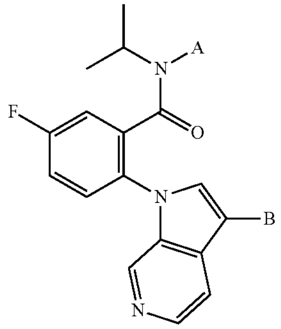
| Reference example | A | B | LC-MS; [M + H]+ or [M + 2H]2+ Rt (min) Analytical condition |
|---|---|---|---|
| 52 | i-Pr | 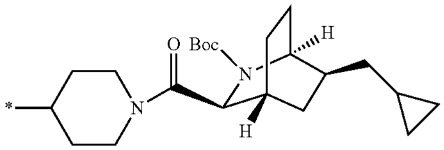 [SMILES: *C1CCN(C(=O)[C@@H]2[C@@H]3CC[C@@H]([C@@H](CC4CC4)C3)N2C(=O)OC(C)(C)C)CC1] | 714.8/1.088/Analytical condition A |
| 53 | Me | 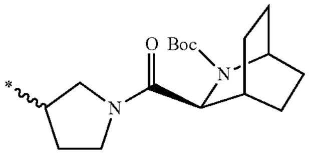 [SMILES: *C1CCN(C(=O)[C@@H]2C3CCC(CC3)N2C(=O)OC(C)(C)C)C1] | 618.49/0.831/Analytical condition A |
| 54 | i-Pr | 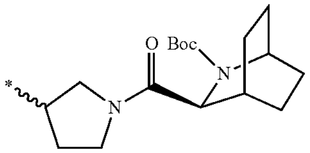 [SMILES: *C1CCN(C(=O)[C@@H]2C3CCC(CC3)N2C(=O)OC(C)(C)C)C1] | 646.60/0.993/Analytical condition A |
| 55 | Me | 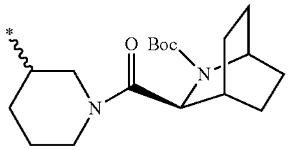 [SMILES: *C1CCCN(C(=O)[C@@H]2C3CCC(CC3)N2C(=O)OC(C)(C)C)C1] | 646.7/0.856/Analytical condition A |
| 56 | Me | 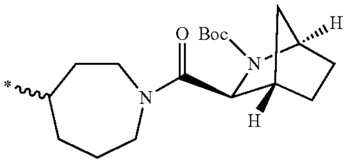 [SMILES: *C1CCCN(C(=O)[C@@H]2[C@H]3CC[C@H](C3)N2C(=O)OC(C)(C)C)CC1] | 632.6/0.794/Analytical condition A |
| 57 | Me | 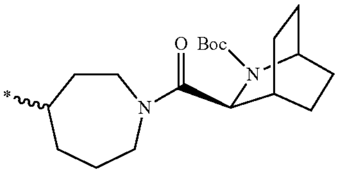 [SMILES: *C1CCCN(C(=O)[C@@H]2C3CCC(CC3)N2C(=O)OC(C)(C)C)CC1] | 646.8/0.787/Analytical condition A |
| 58 | Me | 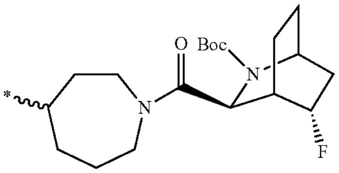 [SMILES: *C1CCCN(C(=O)[C@@H]2C3CCC(C[C@@H]3F)N2C(=O)OC(C)(C)C)CC1] | 664.8/0.738/Analytical condition A |

-continued
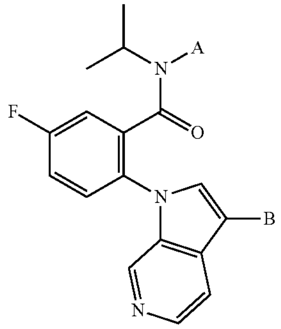
| Reference example | A | B | LC-MS; [M + H]+ or [M + 2H]2+ Rt (min) Analytical condition |
|---|---|---|---|
| 59 | Me | 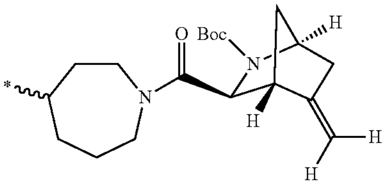 [SMILES: *C1CCCN(C(=O)[C@@H]2[C@@H]3C[C@@H](CC3=C)N2C(=O)OC(C)(C)C)CC1] | 644.5/0.768/Analytical condition A |
| 60 | i-Pr | 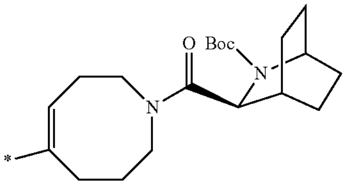 [SMILES: */C1=C/CCN(C(=O)[C@@H]2C3CCC(CC3)N2C(=O)OC(C)(C)C)CCC1] | 686.7/0.951/Analytical condition A |
| 61 | Me | 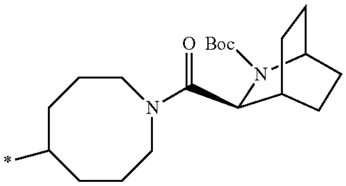 [SMILES: *C1CCCN(C(=O)[C@@H]2C3CCC(CC3)N2C(=O)OC(C)(C)C)CCC1] | 660.55/1.032/Analytical condition A |
| 62 | Me | 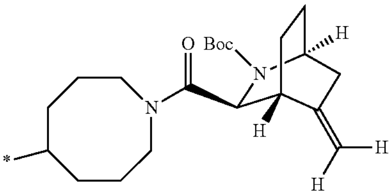 [SMILES: *C1CCCN(C(=O)[C@@H]2[C@@H]3CC[C@@H](CC3=C)N2C(=O)OC(C)(C)C)CCC1] | 672.7/0.982/Analytical condition A |
| 63 | i-Pr | 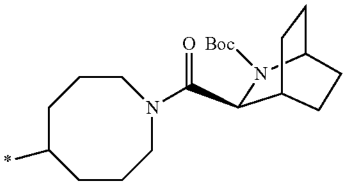 | 688.7/0.871/Analytical condition A |
| 64 | i-Pr | 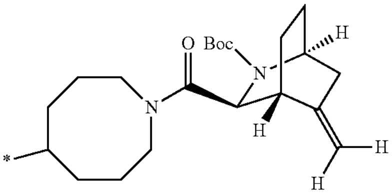 [SMILES: *C1CCCN(C(=O)[C@@H]2[C@@H]3CC[C@@H](CC3=C)N2C(=O)OC(C)(C)C)CCC1] | 700.67/1.163/Analytical condition A |

-continued
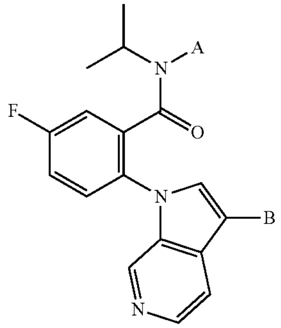
| Reference example | A | B | LC-MS; [M + H]+ or [M + 2H]2+ Rt (min) Analytical condition |
|---|---|---|---|
| 65 | i-Pr | 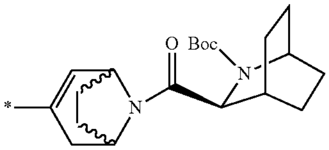 [SMILES: *C1=CC2CCC(C1)N2C(=O)[C@@H]1C2CCC(CC2)N1C(=O)OC(C)(C)C] | 684.7/0.877/Analytical condition A |
| 66 | Me | 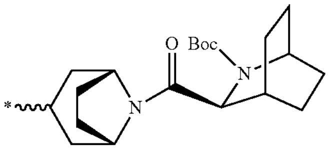 [SMILES: *C1C[C@H]2CC[C@@H](C1)N2C(=O)[C@@H]1C2CCC(CC2)N1C(=O)OC(C)(C)C] | 658.6/0.863/Analytical condition A |
| 67 | Me | 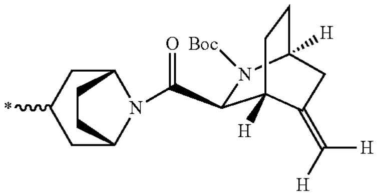 [SMILES: *C1C[C@H]2CC[C@@H](C1)N2C(=O)[C@@H]1[C@@H]2CC[C@@H](CC2=C)N1C(=O)OC(C)(C)C] | 671.61/0.786/Analytical condition A |
| 68 | i-Pr | 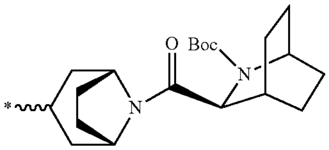 [SMILES: *C1C[C@H]2CC[C@@H](C1)N2C(=O)[C@@H]1C2CCC(CC2)N1C(=O)OC(C)(C)C] | 686.60/1.013/Analytical condition A |
| 69 | i-Pr | 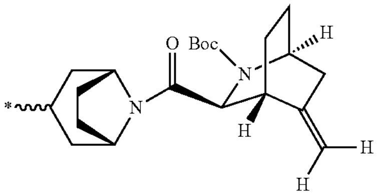 [SMILES: *C1C[C@H]2CC[C@@H](C1)N2C(=O)[C@@H]1[C@@H]2CC[C@@H](CC2=C)N1C(=O)OC(C)(C)C] | 698.72/0.843/Analytical condition A |
| 70 | Me | 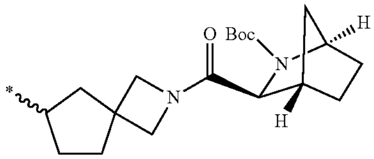 [SMILES: *C1CCC2(C1)CN(C(=O)[C@@H]1[C@H]3CC[C@H](C3)N1C(=O)OC(C)(C)C)C2] | 644.8/0.735/Analytical condition A |

-continued
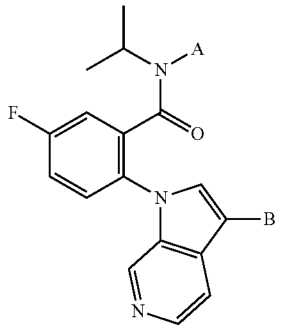
| Reference example | A | B | LC-MS; [M + H]$^{+}$ or [M + 2H]$^{2+}$ Rt (min) Analytical condition |
|---|---|---|---|
| 71 | Me | 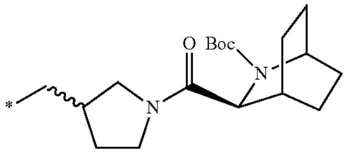 [SMILES: *CC1CCN(C(=O)[C@@H]2C3CCC(CC3)N2C(=O)OC(C)(C)C)C1] | 632.40/0.753/Analytical condition A |
| 72 | Me | 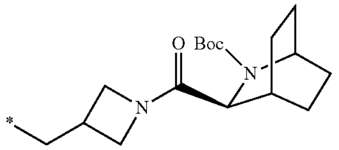 [SMILES: *CC1CN(C(=O)[C@@H]2C3CCC(CC3)N2C(=O)OC(C)(C)C)C1] | 618.7/0.707/Analytical condition A |
| 73 | Me | 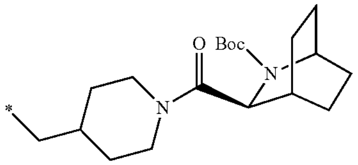 | 645.9/0.878/Analytical condition A |
| 74 | Me | 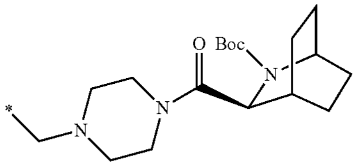 [SMILES: *CN1CCN(C(=O)[C@@H]2C3CCC(CC3)N2C(=O)OC(C)(C)C)CC1] | 647.2/0.626/Analytical condition A |
| 75 | Me | 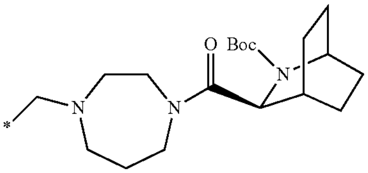 [SMILES: *CN1CCCN(C(=O)[C@@H]2C3CCC(CC3)N2C(=O)OC(C)(C)C)CC1] | 331.4/0.942/Analytical condition A |
| 76 | Me | 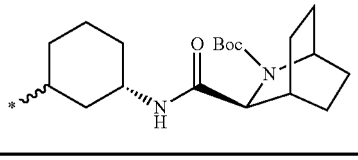 | 646.7/0.856/Analytical condition A |

Example 1

2-(3-{1-[(3S)-2-Azabicyclo[2.2.2]octane-3-carbonyl]piperidin-4-yl}-1H-pyrrolo[2,3-c]pyridin-1-yl)-5-fluoro-N,N-di(propan-2-yl)benzamide

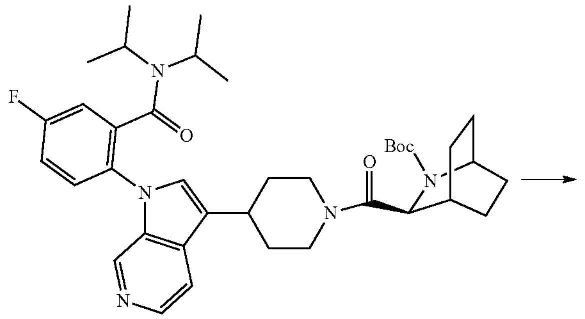

Reference example 47

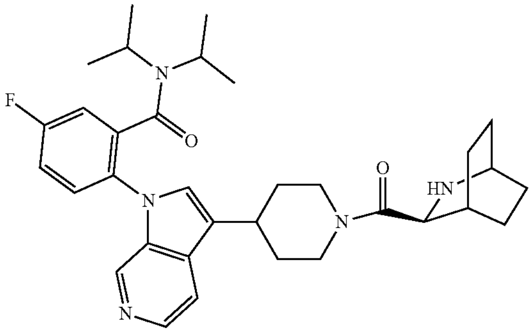

Example 1

To a solution of tert-butyl (3S)-3-[4-(1-{2-[di(propan-2-yl)carbamoyl]-4-fluorophenyl}-1H-pyrrolo[2,3-c]pyridin-3-yl)piperidine-1-carbonyl]-2-azabicyclo[2.2.2]octane-2-carboxylate (245 mg) which was prepared in Reference example 47 in dichloromethane (5.00 mL) was added TFA (2.00 mL) at room temperature, and the mixture was stirred at room temperature for an hour. The solvent was removed from the reaction mixture under reduced pressure, and the residue was purified by amine silica gel column chromatography (ethyl acetate/methanol) to yield the title compound (171 mg).

LC-MS; $[M+H]^+$ 560/Rt (min) 1.443 (Analytical condition B)

$^1$H-NMR (DMSO-D6) δ: 8.64 (1H, s), 8.23 (1H, d, J=5.5 Hz), 7.75-7.68 (2H, m), 7.52-7.41 (2H, m), 7.38 (1H, d, J=4.3 Hz), 4.61 (1H, d, J=11.6 Hz), 3.98-3.88 (2H, m), 3.51-3.11 (3H, m), 2.88-2.80 (2H, m), 2.18-1.99 (2H, m), 1.88-1.27 (15H, m), 1.01-0.92 (6H, m), 0.22 (3H, d, J=4.3 Hz).

Examples 2-30

The following Examples 2 to 30 were prepared according to a similar method to Example 1 by using each corresponding starting compound.

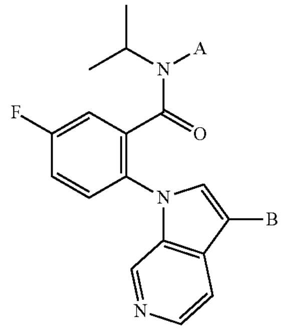

| Example | A | B | LC-MS; $[M + H]^+$ or $[M + 2H]^{2+}$<br>Rt (min)<br>Analytical condition<br>$^1$H-NMR |
|---|---|---|---|
| 2 | Me | 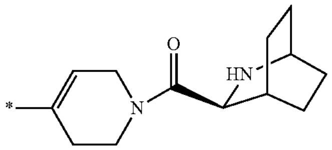 [SMILES: *C1=CCN(C(=O)[C@H]2NC3CCC2CC3)CC1] | 266.14/0.494/Analytical condition A |

-continued

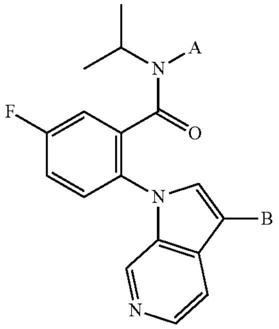

| Example | A | B | LC-MS; [M + H]+ or [M + 2H]2+<br>Rt (min)<br>Analytical condition<br>$^{1}$H-NMR |
|---|---|---|---|
| 3 | i-Pr | 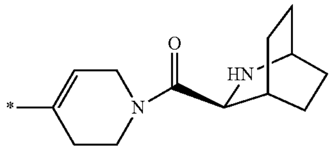 [SMILES: *C1=CCN(C(=O)[C@H]2NC3CCC2CC3)CC1] | 558/1.460/Analytical condition B<br>$^{1}$H-NMR (DMSO-D6) δ: 8.64 (1H, s) , 8.27 (1H, d, J = 5.5 Hz), 7.95-7.88 (1H, m), 7.79-7.72 (1H, m), 7.69-7.62 (1H, m), 7.54-7.40 (2H, m), 6.39-6.26 (1H, m), 4.35-4.08 (2H, m), 3.95 (1H, d, J = 16.5 Hz), 3.71-3.58 (2H, m), 3.51-3.16 (3H, m), 2.84 (1H, s), 2.63-2.41 (2H, m), 1.90-1.38 (8H, m), 1.36 (3H, d, J = 6.1 Hz), 0.96 (3H, d, J = 6.7 Hz), 0.92-0.77 (3H, m), 0.27-0.09 (3H, m). |
| 4 | Me | 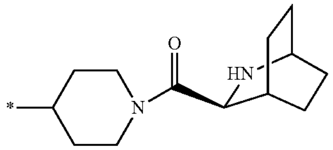 [SMILES: *C1CCN(C(=O)[C@H]2NC3CCC2CC3)CC1] | 266.69/0.530/Analytical condition A<br>$^{1}$H-NMR (DMSO-D6) δ: 8.65-8.51 (1H, m), 8.24-8.18 (1H, m), 7.78-7.65 (2H, m), 7.54-7.44 (2H, m), 7.38-7.31 (1H, m), 4.65-4.49 (1H, m), 3.98-3.83 (2H, m), 3.51-3.09 (2H, m), 2.89-2.76 (2H, m), 2.58-2.33 (3H, m), 2.13-1.95 (2H, m), 1.87-1.33 (12H, m), 1.03-0.89 (3H, m), 0.58-0.08 (3H, m). |
| 5 | i-Pr | 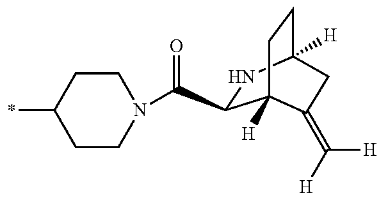 [SMILES: *C1CCN(C(=O)[C@H]2N[C@H]3CC[C@@H]2C(=C)C3)CC1] | 286.8/0.599/Analytical condition A<br>$^{1}$H-NMR (DMSO-D6) δ: 8.64-8.58 (1H, m), 8.25-8.16 (1H, m), 7.74-7.65 (2H, m), 7.50-7.32 (3H, m), 5.00-4.53 (3H, m), 3.93 (1H, s), 3.87-3.73 (1H, m), 3.53-3.09 (5H, m), 3.05 (1H, s), 2.89-2.74 (1H, m), 2.44-2.23 (2H, m), 2.23-1.94 (2H, m), 1.81-1.39 (6H, m), 1.36 (3H, d, J = 6.7 Hz), 1.01-0.85 (6H, m), 0.31-0.14 (3H, m). |

-continued

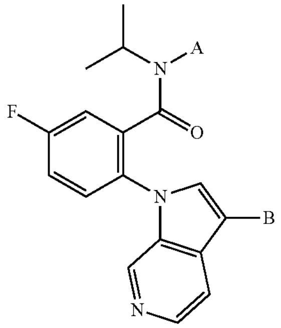

| Example | A | B | LC-MS; $[M + H]^+$ or $[M + 2H]^{2+}$<br>Rt (min)<br>Analytical condition<br>$^1$H-NMR |
|---|---|---|---|
| 6 | i-Pr | 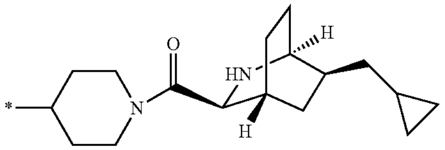 [SMILES: *C1CCN(C(=O)[C@H]2N[C@H]3CC[C@@H]2C[C@@H]3CC2CC2)CC1] | 614/1.555/Analytical condition B<br>$^1$H-NMR (DMSO-D6) δ: 8.62 (1H, s), 8.21 (1H, d, J = 5.5 Hz), 7.70 (2H, dd, J = 26.3, 13.1 Hz) , 7.49-7.39 (2H, m), 7.35 (1H, d, J = 8.6 Hz), 4.65-4.53 (1H, m), 3.98-3.84 (2H, m), 3.49-3.08 (3H, m), 2.85-2.74 (1H, m), 2.71 (1H, s), 2.17-1.95 (4H, m), 1.76-1.21 (12H, m), 1.19-1.02 (2H, m), 1.00-0.85 (6H, m), 0.75-0.63 (1H, m), 0.45-0.36 (2H, m), 0.25-0.15 (3H, m), 0.10--0.03 (2H, m). |
| 7 | Me | 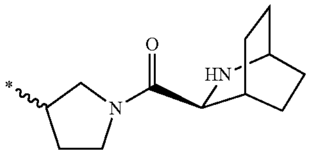 [SMILES: *C1CCN(C(=O)[C@H]2NC3CCC2CC3)C1] | 260.19/0.533/Analytical condition A |
| 8 | i-Pr | 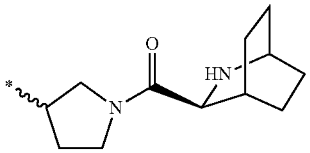 [SMILES: *C1CCN(C(=O)[C@H]2NC3CCC2CC3)C1] | 240.08/0.813/Analytical condition A |
| 9 | Me | 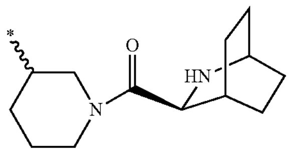 [SMILES: *C1CCCN(C(=O)[C@H]2NC3CCC2CC3)C1] | 266.63/0.524/Analytical condition A |
| 10 | Me | 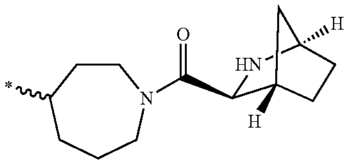 [SMILES: *C1CCCN(C(=O)[C@H]2N[C@@H]3CC[C@H]2C3)CC1] | 532.4/0.477/Analytical condition A<br>$^1$H-NMR ($CDCl_3$) δ: 8.71-8.62 (1H, m), 8.34-8.26 (1H, m), 7.57-7.45 (2H, m), 7.33-7.15 (3H, m), 4.69-4.05 (1H, m), 3.88-3.57 (4H, m), 3.51-2.93 (3H, m), 2.71-2.53 (2H, m), 2.37-2.21 (2H, m), 2.20-1.52 (10H, m), 1.42-1.33 (1H, m), 1.09-0.88 (2H, m), 0.63--0.04 (3H, m). |

-continued
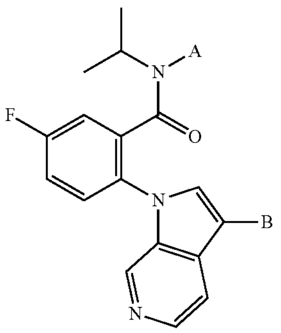
| Example | A | B | LC-MS; $[M + H]^+$ or $[M + 2H]^{2+}$<br>Rt (min)<br>Analytical condition<br>$^1$H-NMR |
|---|---|---|---|
| 11 | Me | 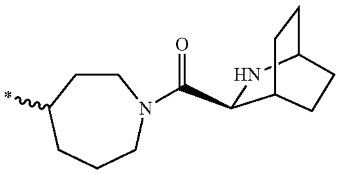 [SMILES: *C1CCCN(C(=O)[C@H]2NC3CCC2CC3)CC1] | 273.8/0.480/Analytical condition A |
| 12 | Me | 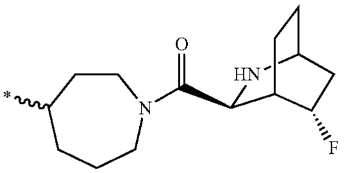 [SMILES: *C1CCCN(C(=O)[C@H]2NC3CCC2[C@@H](F)C3)CC1] | 282.8/0.479/Analytical condition A |
| 13 | Me | 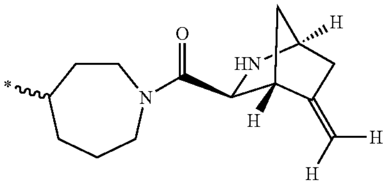 [SMILES: *C1CCCN(C(=O)[C@H]2N[C@@H]3CC(=C)[C@H]2C3)CC1] | 272.8/0.482/Analytical condition A<br>$^1$H-NMR ($CDCl_3$) δ: 8.70-8.60 (1H, m), 8.34-8.20 (1H, m), 7.56-7.43 (2H, m), 7.35-7.14 (3H, m), 5.19-5.08 (1H, m), 4.94-4.86 (1H, m), 4.67-4.50 (1H, m), 4.19-3.91 (2H, m), 3.81-3.35 (3H, m), 3.11-2.84 (4H, m), 2.70-2.61 (2H, m), 2.41-1.49 (10H, m), 1.09-0.86 (3H, m), 0.60-0.07 (3H, m). |
| 14 | i-Pr | 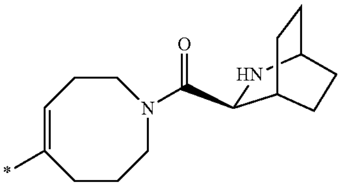 [SMILES: */C1=C/CCN(C(=O)[C@H]2NC3CCC2CC3)CCC1] | 586.35/1.445/Analytical condition B |
| 15 | Me | 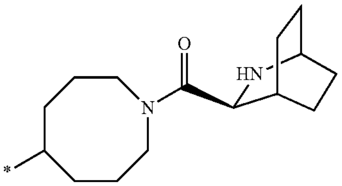 [SMILES: *C1CCCN(C(=O)[C@H]2NC3CCC2CC3)CCC1] | 560/1.50/Analytical condition B |

-continued

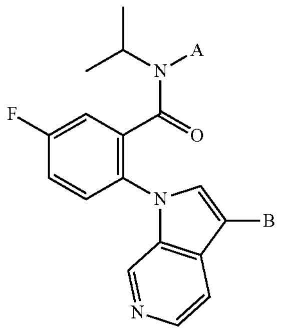

| Example | A | B | LC-MS; [M + H]+ or [M + 2H]2+<br>Rt (min)<br>Analytical condition<br>$^{1}$H-NMR |
|---|---|---|---|
| 16 | Me | 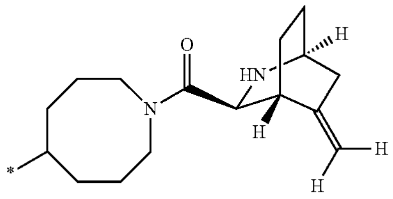 [SMILES: *C1CCCN(C(=O)[C@H]2N[C@H]3CC[C@@H]2C(=C)C3)CCC1] | 572/1.408/Analytical condition B |
| 17 | i-Pr | 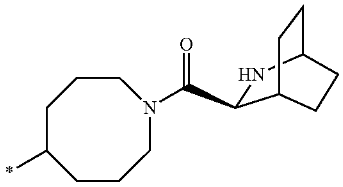 [SMILES: *C1CCCN(C(=O)[C@H]2NC3CCC2CC3)CCC1] | 588/1.50/Analytical condition B |
| 18 | i-Pr | 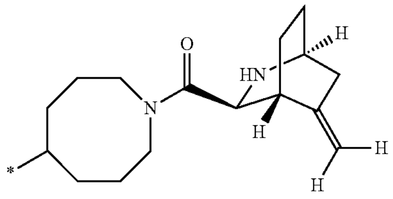 [SMILES: *C1CCCN(C(=O)[C@H]2N[C@H]3CC[C@@H]2C(=C)C3)CCC1] | 600/1.496/Analytical condition B |
| 19a | i-Pr | 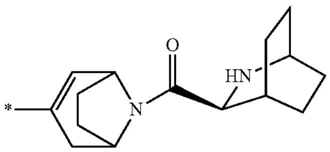<br>The compound is one of the stereoisomers derived from crosslinked part. | 584.35/1.446/Analytical condition B<br>$^{1}$H-NMR ($CDCl_3$) δ: 8.67 (1H, m), 8.34 (1H, m), 7.84-7.64 (1H, m), 7.62-7.41 (2H, m), 7.23 (1H, m), 7.13 (1H, m), 6.58 and 6.46 (total 1H, each m), 5.21 and 4.86 (total 1H, each br s), 4.41 (1H, m), 4.00 (1H, m), 3.64 (0.7H, m), 3.38 (1H, m), 3.28-2.89 (total 3.3H, br m), 2.57-1.34 (total 12H, m), 1.31-1.02 (total 7H, each m), 0.93 (3H, m), 0.05 (3H, m). |

-continued

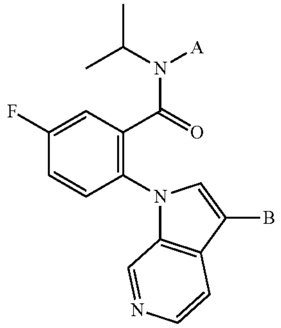

| Example | A | B | LC-MS; [M + H]+ or [M + 2H]2+<br>Rt (min)<br>Analytical condition<br>1H-NMR |
|---|---|---|---|
| 19b | i-Pr | 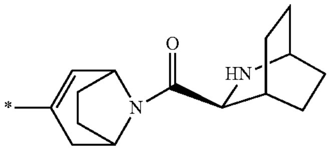<br>The compound is one of the stereoisomers derived from crosslinked part. | 584.35/1.436/Analytical condition B |
| 20 | Me | 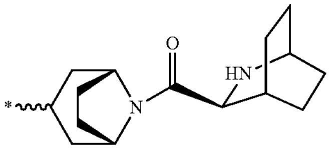 [SMILES: *C1C[C@H]2CC[C@@H](C1)N2C(=O)[C@H]1NC2CCC1CC2] | 279.8/0.614/Analytical condition A<br>$^1$H-NMR (DMSO-D6) δ: 8.66-8.51 (1H, m), 8.25-8.17 (1H, m), 7.78-7.57 (2H, m), 7.55-7.27 (3H, m), 4.81-4.50 (1H, m), 4.42-4.21 (1H, m), 3.88-3.74 (1H, m), 3.56-3.36 (2H, m), 2.88-2.78 (1H, m), 2.58-2.53 (2H, m), 2.41-2.31 (2H, m), 2.11-1.34 (16H, m), 1.07-0.89 (3H, m), 0.57-0.10 (3H, m). |
| 21 | Me | 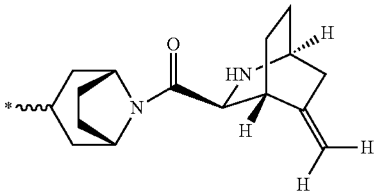 [SMILES: *C1C[C@H]2CC[C@@H](C1)N2C(=O)[C@H]1N[C@H]2CC[C@@H]1C(=C)C2] | 286.5/0.532/Analytical condition A |
| 22 | i-Pr | 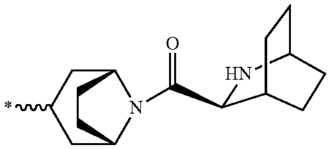 [SMILES: *C1C[C@H]2CC[C@@H](C1)N2C(=O)[C@H]1NC2CCC1CC2] | 586/1.51/Analytical condition B |
| 23 | i-Pr | 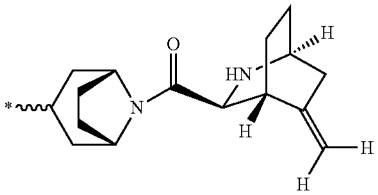 [SMILES: *C1C[C@H]2CC[C@@H](C1)N2C(=O)[C@H]1N[C@H]2CC[C@@H]1C(=C)C2] | 300.54/0.638/Analytical condition A |

-continued
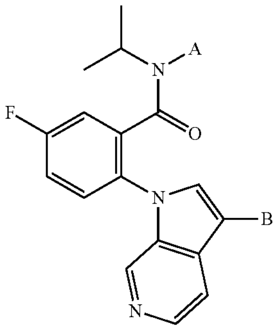
| Example | A | B | LC-MS; [M + H]$^+$ or [M + 2H]$^{2+}$<br>Rt (min)<br>Analytical condition<br>$^1$H-NMR |
|---|---|---|---|
| 24 | Me | 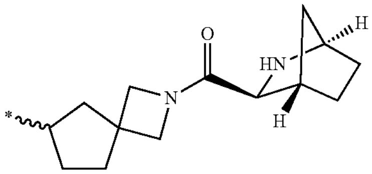 [SMILES: *C1CCC2(C1)CN(C(=O)[C@H]1N[C@@H]3CC[C@H]1C3)C2] | 272.84/0.486/Analytical condition A<br>$^1$H-NMR ($CDCl_3$) δ: 8.63-8.58 (1H, m), 8.27-8.20 (1H, m), 7.51-7.40 (2H, m), 7.25-7.09 (3H, m), 4.65-3.82 (4H, m), 3.74 (1H, s), 3.50-3.21 (2H, m), 2.65-2.57 (2H, m), 2.54-2.45 (1H, m), 2.42-2.29 (1H, m), 2.26-2.11 (3H, m), 2.11-1.84 (4H, m), 1.84-1.39 (5H, m), 1.34-1.25 (1H, m), 1.07-0.81 (3H, m), 0.61--0.05 (3H, m). |
| 25 | Me | 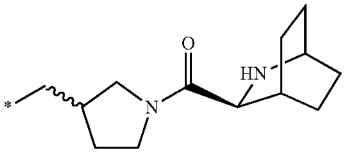 [SMILES: *CC1CCN(C(=O)[C@H]2NC3CCC2CC3)C1] | 267.60/0.424/Analytical condition A<br>$^1$H-NMR (DMSO-D6) δ: 8.50-8.36 (1H, m), 8.10-8.02 (1H, m), 7.61-7.47 (2H, m), 7.40-7.19 (3H, m), 3.61-3.39 (3H, m), 3.39-3.20 (4H, m), 2.80-2.55 (3H, m), 2.50-2.36 (2H, m), 2.24-2.15 (1H, m), 1.90-1.13 (11H, m), 0.88-0.68 (3H, m), 0.42--0.08 (3H, m). |
| 26 | Me | 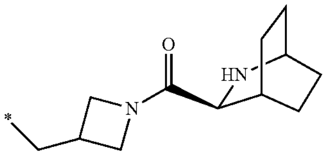 [SMILES: *CC1CN(C(=O)[C@H]2NC3CCC2CC3)C1] | 259.5/0.836/Analytical condition A |
| 27 | Me | 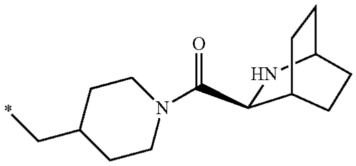 | 273.6/0.623/Analytical condition A |
| 28 | Me | 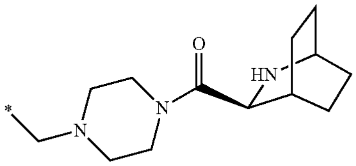 [SMILES: *CN1CCN(C(=O)[C@H]2NC3CCC2CC3)CC1] | 274.1/0.487/Analytical condition A |

-continued

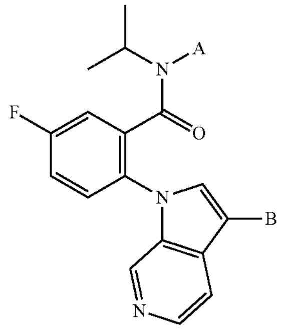

| Example | A | B | LC-MS; [M + H]$^+$ or [M + 2H]$^{2+}$<br>Rt (min)<br>Analytical condition<br>$^1$H-NMR |
|---|---|---|---|
| 29 | Me | 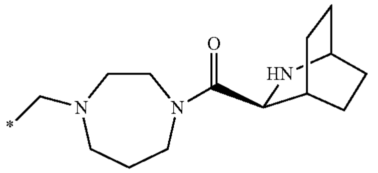 [SMILES: *CN1CCCN(C(=O)[C@H]2NC3CCC2CC3)CC1] | 281.1/0.687/Analytical condition A |
| 30 | Me | 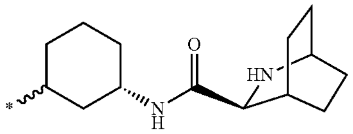 [SMILES: *C1CCC[C@H](NC(=O)[C@H]2NC3CCC2CC3)C1] | 273.7/0.549/Analytical condition A |

Tests

Test 1: Test for Evaluating the Inhibition of Cell Proliferation

MV4; 11 cells were obtained from American Type Culture Collection (ATCC). The cells were cultured at 37° C. in the presence of 5% $CO_2$ in RPMI 1640 medium containing 10% fetal bovine serum and 1% penicillin/streptomycin.

The cells were plated to a 96-well plate in 2000 cells/well, each test compound was added thereto to adjust the final concentration of DMSO to 0.1% of DMSO, and the cells were cultured for 7 days. After the cultivation, the cell viability was calculated with PrestoBlue™ Cell Viability Reagent (Invitrogen, A13261). The $IC_{50}$ value was calculated from a survival curve that corresponds to the concentration of the test compound at which the cell proliferation inhibition rate is 50%.

The results of the evaluation in Test 1 are shown in the following table.

| Example | MV4; 11 $IC_{50}$ (μM) |
|---|---|
| 1 | 0.26 |
| 2 | 0.53 |
| 3 | 0.036 |
| 4 | 0.073 |
| 5 | 0.035 |
| 6 | <0.0030 |
| 7 | 0.052 |
| 8 | 0.024 |
| 9 | 1.7 |
| 10 | 0.089 |
| 11 | <0.030 |
| 12 | <0.030 |
| 13 | 0.13 |

-continued

| Example | MV4; 11 $IC_{50}$ (μM) |
|---|---|
| 14 | 2.2 |
| 15 | 0.42 |
| 16 | 0.24 |
| 17 | 0.83 |
| 18 | 0.73 |
| 19a | <0.030 |
| 19b | 0.14 |
| 20 | 0.085 |
| 21 | 0.43 |
| 22 | 0.064 |
| 23 | 0.28 |
| 24 | 0.058 |
| 25 | 0.029 |
| 26 | 1.7 |
| 27 | 0.78 |
| 28 | 3.2 |
| 29 | 2.9 |
| 30 | 0.55 |

The compounds of Examples 3, 4, 5, 6, 7, 8, 10, 11, 12, 19, 20, 22, 24, and 25 showed the potent cell proliferation inhibition activity as shown in the above table.

Test 2: Test for the hERG Inhibition

To a cultured CHO cell strain which stably expresses hERG (human Ether-a-go-go Related Gene) was added each test compound to adjust the final concentration to 0.0135 to 0.5% of DMSO. The hERG current was measured with QPatch HT (Sophion Inc.), and the concentration at which 50% of the hERG current was inhibited by each test compound ($IC_{50}$ value; μM) was calculated.

The compounds of Examples were tested according to Test example 2. And, the hERG/MV4; 11 was calculated by dividing the compound concentration obtained in Test example 2, at which 50% of the hERG current is inhibited, by the compound concentration obtained in Test example 1, at which 50% of the proliferation of MV4; 11 cells is inhibited. The results are shown in the following table.

| Example | hERG $IC_{50}$ (μM) | hERG/MV4; 11 |
|---|---|---|
| 1 | 30 | 114 |
| 2 | 54 | 102 |
| 3 | 18 | 489 |
| 4 | >100 | >1370 |
| 5 | 21 | 589 |
| 6 | <2.7 | — |
| 7 | 40 | 775 |
| 8 | 9.7 | 404 |
| 9 | 37 | 22 |
| 10 | 55 | 621 |
| 11 | 39 | >1287 |
| 12 | 32 | >1050 |
| 13 | 26 | 198 |
| 14 | 3.2 | 1.5 |
| 15 | 17 | 40 |
| 16 | — | — |
| 17 | 3.0 | 3.6 |
| 18 | — | — |
| 19a | 6.0 | >200 |
| 19b | 4.5 | 32 |
| 20 | 32 | 373 |
| 21 | — | — |
| 22 | 5.8 | 91 |
| 23 | — | — |
| 24 | 67 | 1157 |
| 25 | 9.7 | 334 |
| 26 | >100 | >59 |
| 27 | >100 | >128 |
| 28 | >100 | >31 |
| 29 | >100 | >34 |
| 30 | 7.3 | 13 |

As shown in the above table, there is a more than 100-fold gap between the concentration at which 50% of the proliferation of MV4; 11 cells was inhibited and the concentration at which 50% of the hERG current was inhibited in the compounds of Examples 1, 2, 3, 4, 5, 7, 8, 10, 11, 12, 13, 19, 20, 24, 25, and 27. Especially, it is proved that there is a more than 1000-fold excellent gap between the concentration at which 50% of the proliferation of RS4; 11 cells was inhibited and the concentration at which 50% of the hERG current was inhibited in the compounds of Examples 4, 11, 12, and 24.

INDUSTRIAL APPLICABILITY

The compounds of the present invention can inhibit the binding of a MLL fusion protein and menin to provide the antitumor effect.

The invention claimed is:

1. A compound of formula (1a):

(1a)

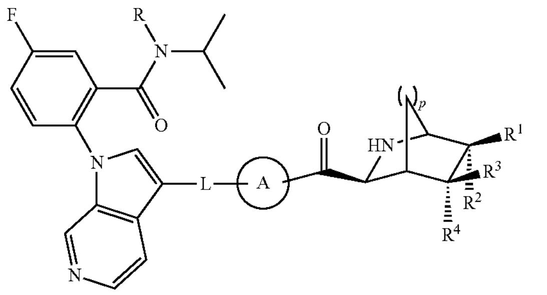

or a pharmaceutically acceptable salt thereof, wherein p is 1 or 2;

$R^1$, $R^2$, $R^3$, and $R^4$ are each independently hydrogen atom, halogen, —$OR^7$, or -M-Q; or $R^1$ and $R^2$ and/or $R^3$ and $R^4$ may be combined together to form each independently =O or =$CR^{12A}R^{13A}$;

M is, each independently if there are plural, $C_{1-6}$ alkylene (which may be substituted with 1 to 5 the same or different substituents selected from the group consisting of fluorine atom, chlorine atom, bromine atom, hydroxy, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenylene, $C_{2-6}$ alkynylene, $C_{3-10}$ cycloalkylene, 3- to 10-membered saturated heterocyclyl, $C_{6-10}$ arylene, or 5- to 12-membered heteroarylene, wherein the alkenylene, the alkynylene, the cycloalkylene, the saturated heterocyclyl, the arylene, and the heteroarylene may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

Q is, each independently if there are plural, hydrogen atom, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano;

$R^7$ is, each independently if there are plural, hydrogen atom, $C_{1-6}$ alkyl (which may be substituted with 1 to 5 the same or different substituents selected from the group consisting of fluorine atom, chlorine atom, bromine atom, hydroxy, phenyl, 5- to 6-membered heteroaryl, $C_{2-4}$ alkynyl, $C_{3-7}$ cycloalkyl, 3- to 7-membered saturated heterocyclyl, $C_{1-3}$ alkoxy, —$CONR^{36A}R^{37A}$, —$NR^{36A}R^{37A}$, —$NR^{36A}COR^{35A}$, —$NR^{36A}SO_2R^{35A}$, —$SO_2R^{35A}$, —$SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano;

$R^{12A}$ and $R^{13A}$ are each independently hydrogen atom, halogen, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano), $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl, wherein the alkenyl, the alkynyl, the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

Ring A is (A-1), (A-2), (A-3), or (A-4):

(A-1)

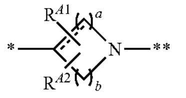

(A-2)

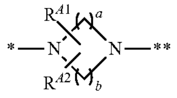

(A-3)

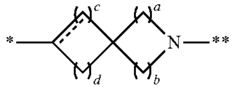

(A-4)

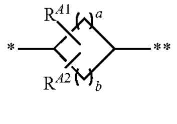

wherein * is a bonding site to L, ** is a bonding site to the carbonyl group, and the dot-line in the ring means that there may be optionally a unsaturated bond in the ring;

$R^{A1}$ and $R^{A2}$ are each independently hydrogen atom or $C_{1-3}$ alkyl, or $R^{A1}$ and $R^{A2}$ may be combined with each carbon atom to which they are attached to form a bridged structure with $C_{1-3}$ alkylene;

a, b, c, and d are each independently 1, 2, or 3;

L is single bond or $—CH_2—$; and

R is methyl or isopropyl.

2. The compound of claim 1 or a pharmaceutically acceptable salt thereof, wherein M is, each independently if there are plural, $C_{1-6}$ alkylene which may be substituted with 1 to 5 the same or different substituents selected from the group consisting of fluorine atom, hydroxy, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano.

3. The compound of claim 1 or a pharmaceutically acceptable salt thereof, wherein Q is, each independently if there are plural, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano.

4. The compound of claim 1 or a pharmaceutically acceptable salt thereof, wherein $R^7$ is, each independently if there are plural, hydrogen atom, $C_{1-6}$ alkyl (which may be substituted with 1 to 5 the same or different substituents selected from the group consisting of fluorine atom, phenyl, $C_{3-7}$ cycloalkyl, and 3- to 7-membered saturated heterocyclyl), $C_{2-6}$ alkenyl, $C_{2-6}$ alkynyl, $C_{3-10}$ cycloalkyl, 3- to 10-membered saturated heterocyclyl (wherein the cycloalkyl and the saturated heterocyclyl may be each independently substituted with 1 to 5 the same or different substituents selected from the group consisting of fluorine atom and $C_{1-3}$ alkyl), $C_{6-10}$ aryl, or 5- to 12-membered heteroaryl, wherein the aryl and the heteroaryl may be each independently substituted with 1 to 5 the same or different substituents selected from the group consisting of fluorine atom, chlorine atom, bromine atom, and $C_{1-3}$ alkyl.

5. The compound of claim 1 or a pharmaceutically acceptable salt thereof, wherein $R^{12A}$ and $R^{13A}$ are each independently hydrogen atom, $C_{1-6}$ alkyl (which may be substituted with 1 to 5 the same or different substituents selected from the group consisting of fluorine atom, chlorine atom, bromine atom, hydroxy, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano), $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 5 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are each attached to form 3- to 8-membered saturated carbocycle.

6. The compound of claim 1 or a pharmaceutically acceptable salt thereof, wherein $R^1$, $R^2$, $R^3$, and $R^4$ are each independently hydrogen atom, halogen, $—OR^7$, or -M-Q; or $R^1$ and $R^2$ and/or $R^3$ and $R^4$ may be combined together to form each independently $=O$ or $=CR^{12A}R^{13A}$;

M is, each independently if there are plural, $C_{1-6}$ alkylene which may be substituted with 1 to 3 the same or different substituents selected from the group consisting of fluorine atom, hydroxy, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano;

Q is, each independently if there are plural, $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 3 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}SO_2R^{35A}$, $—SO_2NR^{36A}R^{37A}$, and cyano;

$R^7$ is, each independently if there are plural, hydrogen atom, $C_{1-6}$ alkyl (which may be substituted with one phenyl), or $C_{2-6}$ alkenyl;

$R^{12A}$ and $R^{13A}$ are each independently hydrogen atom, $C_{1-6}$ alkyl (which may be substituted with 1 to 3 the same or different substituents selected from the group consisting of fluorine atom, chlorine atom, bromine atom, hydroxy, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano), $C_{3-10}$ cycloalkyl, 3- to 10-membered saturated heterocyclyl, $C_{6-10}$ aryl, or 5- to 12-membered heteroaryl, wherein the cycloalkyl, the saturated heterocyclyl, the aryl, and the heteroaryl may be each independently substituted with 1 to 3 the same or different substituents selected from the group consisting of fluorine atom, chlorine atom, bromine atom, hydroxy, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{37A}$, $—NR^{36A}SO_2R^{35A}$, $—SO_2R^{35A}$, $—SO_2NR^{37A}R^{37A}$, and cyano, and if there are plural $R^{12A}$ or $R^{13A}$, each $R^{12A}$ or $R^{13A}$ may be the same or different, or when $R^{12A}$ and $R^{13A}$ are both $C_{1-6}$ alkyl, they may be combined with the carbon atom to which they are attached to form 3- to 8-membered saturated carbocycle;

$R^{35A}$ is, each independently if there are plural, $C_{1-6}$ alkyl;

$R^{36A}$ and $R^{37A}$ are each independently hydrogen atom or $C_{1-6}$ alkyl, and if there are plural $R^{36A}$ or $R^{37A}$, each $R^{36A}$ or $R^{37A}$ may be the same or different, or when $R^{36A}$ and $R^{37A}$ are both $C_{1-6}$ alkyl, they may be combined with the nitrogen atom to which they are attached to form 3- to 6-membered nitrogen-containing saturated heterocycle;

Ring A is (A-1), (A-2), or (A-3);

a, b, c, and d are independently 1, 2, or 3;

L is single bond or $—CH_2—$; and

R is methyl or isopropyl.

7. The compound of claim 1 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=O$ or $=CR^{12A}R^{13A}$.

8. The compound of claim 1 or a pharmaceutically acceptable salt thereof, wherein M is, each independently if there are plural, $C_{1-3}$ alkylene which may be substituted with 1 to 3 the same or different substituents selected from the group consisting of fluorine atom, $C_{2-4}$ alkynyl, $C_{1-3}$ alkoxy, $—NR^{36A}R^{37A}$, and cyano.

9. The compound of claim 1 or a pharmaceutically acceptable salt thereof, wherein Q is, each independently if there are plural, $C_{3-6}$ cycloalkyl, 3- to 6-membered saturated heterocyclyl, phenyl, or 5- to 6-membered heteroaryl, wherein the cycloalkyl, the saturated heterocyclyl, the phenyl, and the heteroaryl may be each independently substituted with 1 to 3 the same or different substituents selected from the group consisting of fluorine atom, chlorine atom, bromine atom, $C_{1-3}$ alkyl, $C_{2-4}$ alkynyl, $C_{1-3}$ alkoxy, $—CONR^{36A}R^{37A}$, $—NR^{36A}R^{37A}$, $—NR^{36A}COR^{35A}$, $—NR^{36A}SO_2R^{35A}$, $—SO_2R^{35A}$, $—SO_2NR^{36A}R^{37A}$, and cyano.

10. The compound of claim 1 or a pharmaceutically acceptable salt thereof, wherein $R^{12A}$ and $R^{13A}$ are each independently hydrogen atom, $C_{1-6}$ alkyl (which may be substituted with 1 to 3 the same or different substituents selected from the group consisting of fluorine atom, $—NR^{36A}SO_2R^{35A}$, $—SO_2NR^{36A}R^{37A}$, and cyano), $C_{3-10}$ cycloalkyl (which may be substituted with 1 to 3 the same or different substituents selected from the group consisting of fluorine atom, $C_{1-3}$ alkyl, $—NR^{36A}SO_2R^{35A}$, $—SO_2NR^{36A}R^{37A}$, and cyano), and if there are plural $R^{12A}$ or $R^{13A}$, each $R^{12A}$ or $R^{13A}$ may be the same or different, or when $R^{12A}$ and $R^{13A}$ are both $C_{1-3}$ alkyl, they may be combined with the carbon atom to which they are attached to form 3- to 6-membered saturated carbocycle.

11. The compound of claim 1 or a pharmaceutically acceptable salt thereof, wherein Ring A is (A-1) or (A-3).

12. The compound of claim 1 or a pharmaceutically acceptable salt thereof, wherein L is single bond or methylene.

13. The compound of claim 1 or a pharmaceutically acceptable salt thereof, wherein Ring A is (A-1), and L is single bond.

14. The compound of claim 1 or a pharmaceutically acceptable salt thereof, wherein Ring A is (A-1), and L is methylene.

15. The compound of claim 1 or a pharmaceutically acceptable salt thereof, wherein Ring A is (A-3), and L is single bond.

16. The compound of claim 1 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form each independently $=CR^{12A}R^{13A}$.

17. The compound of claim 1 or a pharmaceutically acceptable salt thereof, wherein M is methylene.

18. The compound of claim 1 or a pharmaceutically acceptable salt thereof, wherein Q is, each independently if there are plural, $C_{3-6}$ cycloalkyl which may be substituted with 1 to 3 the same or different substituents selected from the group consisting of fluorine atom and $C_{1-3}$ alkyl.

19. The compound of claim 1 or a pharmaceutically acceptable salt thereof, wherein Q is, each independently if there are plural, $C_{3-6}$ cycloalkyl.

20. The compound of claim 1 or a pharmaceutically acceptable salt thereof, wherein $R^{12A}$ and $R^{13A}$ are hydrogen atom.

21. The compound of claim 1 or a pharmaceutically acceptable salt thereof, wherein $R^1$, $R^2$, $R^3$, and $R^4$ are each independently hydrogen atom, fluorine atom, or -M-Q; or $R^1$ and $R^2$ and/or $R^3$ and $R^4$ may be combined together to form $=CH_2$;

M is, each independently if there are plural, methylene; and

Q is, each independently if there are plural, $C_{3-6}$ cycloalkyl.

22. The compound of claim 1 or a pharmaceutically acceptable salt thereof, wherein $R^1$ and $R^2$ are hydrogen atom; and $R^3$ and $R^4$ are each independently hydrogen atom or fluorine atom;

provided that both $R^3$ and $R^4$ are not simultaneously hydrogen atom.

23. The compound of claim 1 or a pharmaceutically acceptable salt thereof, wherein $R^1$ and $R^2$ are each independently hydrogen atom or -M-Q; and $R^3$ and $R^4$ are each independently hydrogen atom or fluorine atom;

provided that both $R^1$ and $R^2$ are not simultaneously hydrogen atom.

24. The compound of claim 1 or a pharmaceutically acceptable salt thereof, wherein $R^1$ is -M-Q, $R^2$ is hydrogen atom, $R^3$ is hydrogen atom or fluorine atom, and $R^4$ is hydrogen atom.

25. The compound of claim 1 or a pharmaceutically acceptable salt thereof, wherein $R^1$, $R^2$, $R^3$, and $R^4$ are each independently hydrogen atom; or $R^1$ and $R^2$ and/or $R^3$ and $R^4$ may be combined together to form $=CH_2$;

provided that all of $R^1$, $R^2$, $R^3$ and $R^4$ are not simultaneously hydrogen atom.

26. The compound of claim 1 or a pharmaceutically acceptable salt thereof, wherein $R^1$ and $R^2$ are hydrogen atom; and $R^3$ and $R^4$ are combined together to form $=CH_2$.

27. The compound of claim 1 or a pharmaceutically acceptable salt thereof, wherein the sum of a and b is 2, 3, 4, 5 or 6.

28. The compound of claim 1 or a pharmaceutically acceptable salt thereof, wherein p is 1.

29. The compound of claim 1 or a pharmaceutically acceptable salt thereof, wherein p is 2.

30. The compound of claim 1 or a pharmaceutically acceptable salt thereof, selected from:

2-(3-{1-[(3S)-2-azabicyclo[2.2.2]octane-3-carbonyl]piperidin-4-yl}-1H-pyrrolo[2,3-c]pyridin-1-yl)-5-fluoro-N,N-di(propan-2-yl)benzamide, 2-(3-{1-[(3S)-2-azabicyclo[2.2.2]octane-3-carbonyl]-1,2,3,6-tetrahydropyridin-4-yl}-1H-pyrrolo[2,3-c]pyridin-1-yl)-5-fluoro-N-methyl-N-(propan-2-yl)benzamide, 2-(3-{1-[(3S)-2-azabicyclo[2.2.2]octane-3-carbonyl]-1,2,3,6-tetrahydropyridin-4-yl}-1H-pyrrolo[2,3-c]pyridin-1-yl)-5-fluoro-N,N-di(propan-2-yl)benzamide, 2-(3-{1-[(3S)-2-azabicyclo[2.2.2]octane-3-carbonyl]piperidin-4-yl}-1H-pyrrolo[2,3-c]pyridin-1-yl)-5-fluoro-N-methyl-N-(propan-2-yl)benzamide, 5-fluoro-2-(3-{1-[(1S,3S,4R)-5-methylidene-2-azabicyclo[2.2.2]octane-3-carbonyl]piperidin-4-yl}-1H-pyrrolo[2,3-c]pyridin-1-yl)-N,N-di(propan-2-yl)benzamide, 2-(3-{1-[(1S,3S,4R,6S)-6-(cyclopropylmethyl)-2-azabicyclo[2.2.2]octane-3-carbonyl]piperidin-4-yl}-1H-pyrrolo[2,3-c]pyridin-1-yl)-5-fluoro-N,N-di(propan-2-yl)benzamide, 2-(3-{1-[(3S)-2-azabicyclo[2.2.2]octane-3-carbonyl]pyrrolidin-3-yl}-1H-pyrrolo[2,3-c]pyridin-1-yl)-5-fluoro-N-methyl-N-(propan-2-yl)benzamide, 2-(3-{1-[(3S)-2-azabicyclo[2.2.2]octane-3-carbonyl]pyrrolidin-3-yl}-1H-pyrrolo[2,3-c]pyridin-1-yl)-5-fluoro-N,N-di(propan-2-yl)benzamide, 2-(3-{1-[(3S)-2-azabicyclo[2.2.2]octane-3-carbonyl]piperidin-3-yl}-1H-pyrrolo[2,3-c]pyridin-1-yl)-5-fluoro-N-methyl-N-(propan-2-yl)benzamide, 2-(3-{1-[(1R,3S,4S)-2-azabicyclo[2.2.1]heptane-3-carbonyl]azepan-4-yl}-1H-pyrrolo[2,3-c]pyridin-1-yl)-5-fluoro-N-methyl-N-(propan-2-yl)benzamide, 2-(3-{1-[(3S)-2-azabicyclo[2.2.2]octane-3-carbonyl]azepan-4-yl}-1H-pyrrolo[2,3-c]pyridin-1-yl)-5-fluoro-N-methyl-N-(propan-2-yl)benzamide, 5-fluoro-2-(3-{1-[(1S,3S,4S,5S)-5-fluoro-2-azabicyclo[2.2.2]octane-3-carbonyl]azepan-4-yl}-1H-pyrrolo[2,3-c]pyridin-1-yl)-N-methyl-N-(propan-2-yl)benzamide, 5-fluoro-N-methyl-2-(3-{1-[(1S,3S,4R)-5-methylidene-2-azabicyclo[2.2.1]heptane-3-carbonyl]azepan-4-yl}-1H-pyrrolo[2,3-c]pyridin-1-yl)-N-(propan-2-yl)benzamide, 2-(3-{1-[(3S)-2-azabicyclo[2.2.2]octane-3-carbonyl]-1,2,3,4,7,8-hexahydroazocin-5-yl}-1H-pyrrolo[2,3-c]pyridin-1-yl)-5-fluoro-N,N-di(propan-2-yl)benzamide, 2-(3-{1-[(3S)-2-azabicyclo[2.2.2]octane-3-carbonyl]azocan-5-yl}-1H-pyrrolo[2,3-c]pyridin-1-yl)-5-fluoro-N-methyl-N-(propan-2-yl)benzamide, 5-fluoro-N-methyl-2-(3-{1-[(1S,3S,4R)-5-methylidene-2-azabicyclo[2.2.2]octane-3-carbonyl]azocan-5-yl}-1H-pyrrolo[2,3-c]pyridin-1-yl)-N-(propan-2-yl)benzamide, 2-(3-{1-[(3S)-2-azabicyclo[2.2.2]octane-3-carbonyl]azocan-5-yl}-1H-pyrrolo[2,3-c]pyridin-1-yl)-5-fluoro-N,N-di(propan-2-yl)benzamide, 5-fluoro-2-(3-{1-[(1S,3S,4R)-5-methylidene-2-azabicyclo[2.2.2]octane-3-carbonyl]azocan-5-yl}-1H-pyrrolo[2,3-c]pyridin-1-yl)-N,N-di(propan-2-yl)benzamide, 2-(3-{8-[(3S)-2-azabicyclo[2.2.2]octane-3-carbonyl]-8-azabicyclo[3.2.1]oct-2-en-3-yl}-1H-pyrrolo[2,3-c]pyridin-1-yl)-5-fluoro-N,N-di(propan-2-yl)benzamide, 2-(3-{8-[(3S)-2-azabicyclo[2.2.2]octane-3-carbonyl]-8-azabicyclo[3.2.1]oct-2-en-3-yl}-1H-pyrrolo[2,3-c]pyridin-1-yl)-5-fluoro-N,N-di(propan-2-yl)benzamide, 2-(3-{8-[(3S)-2-azabicyclo[2.2.2]octane-3-carbonyl]-8-azabicyclo[3.2.1]octan-3-yl}-1H-pyrrolo[2,3-c]pyridin-1-yl)-5-fluoro-N-methyl-N-(propan-2-yl)benzamide, 5-fluoro-N-methyl-2-(3-{8-[(1S,3S,4R)-5-methylidene-2-azabicyclo[2.2.2]octane-3-carbonyl]-8-azabicyclo[3.2.1]octan-3-yl}-1H-pyrrolo[2,3-c]pyridin-1-yl)-N-(propan-2-yl)benzamide, 2-(3-{8-[(3S)-2-azabicyclo[2.2.2]octane-3-carbonyl]-8-azabicyclo[3.2.1]octan-3-yl}-1H-pyrrolo[2,3-c]pyridin-1-yl)-5-fluoro-N,N-di(propan-2-yl)benzamide, 5-fluoro-2-(3-{8-[(1S,3S,4R)-5-methylidene-2-azabicyclo[2.2.2]octane-3-carbonyl]-8-azabicyclo[3.2.1]octan-3-yl}-1H-pyrrolo[2,3-c]pyridin-1-yl)-N,N-di(propan-2-yl)benzamide, 2-(3-{2-[(1R,3S,4S)-2-azabicyclo[2.2.1]heptane-3-carbonyl]-2-azaspiro[3.4]octan-6-yl}-1H-pyrrolo[2,3-c]pyridin-1-yl)-5-fluoro-N-methyl-N-(propan-2-yl)benzamide, 2-[3-({1-[(3S)-2-azabicyclo[2.2.2]octane-3-carbonyl]pyrrolidin-3-yl}methyl)-1H-pyrrolo[2,3-c]pyridin-1-yl]-5-fluoro-N-methyl-N-(propan-2-yl)benzamide, 2-[3-({1-[(3S)-2-azabicyclo[2.2.2]octane-3-carbonyl]azetidin-3-yl}methyl)-1H-pyrrolo[2,3-c]pyridin-1-yl]-5-fluoro-N-methyl-N-(propan-2-yl)benzamide, 2-[3-({1-[(3S)-2-azabicyclo[2.2.2]octane-3-carbonyl]piperidin-4-yl}methyl)-1H-pyrrolo[2,3-c]pyridin-1-yl]-5-fluoro-N-methyl-N-(propan-2-yl)benzamide, 2-[3-({4-[(3S)-2-azabicyclo[2.2.2]octane-3-carbonyl]piperazin-1-yl}methyl)-1H-pyrrolo[2,3-c]pyridin-1-yl]-5-fluoro-N-methyl-N-(propan-2-yl)benzamide, 2-[3-({4-[(3S)-2-azabicyclo[2.2.2]octane-3-carbonyl]-1,4-diazepan-1-yl}methyl)-1H-pyrrolo[2,3-c]pyridin-1-yl]-5-fluoro-N-methyl-N-(propan-2-yl)benzamide, and (3S)—N-[(1S)-3-(1-{4-fluoro-2-[methyl(propan-2-yl)carbamoyl]phenyl}-1H-pyrrolo[2,3-c]pyridin-3-yl)cyclohexyl]-2-azabicyclo[2.2.2]octane-3-carboxamide.

31. The compound of claim 1 or a pharmaceutically acceptable salt thereof, selected from:

5-fluoro-2-(3-{1-[(1S,3S,4R)-5-methylidene-2-azabicyclo[2.2.2]octane-3-carbonyl]piperidin-4-yl}-11H-pyrrolo[2,3-c]pyridin-1-yl)-N,N-di(propan-2-yl)benzamide, 2-(3-{1-[(1S,3S,4R,6S)-6-(cyclopropylmethyl)-2-azabicyclo[2.2.2]octane-3-carbonyl]piperidin-4-yl-}1H-pyrrolo[2,3-c]pyridin-1-yl)-5-fluoro-N,N-di(propan-2-yl)benzamide, 5-fluoro-N-methyl-2-(3-{1-[(1S,3S,4R)-5-methylidene-2-azabicyclo[2.2.1]heptane-3-carbonyl]azepan-4-yl}-1H-pyrrolo[2,3-c]pyridin-1-yl)-N-(propan-2-yl)benzamide, and 2-[3-({1-[(3S)-2-azabicyclo[2.2.2]octane-3-carbonyl]pyrrolidin-3-yl}methyl)-1H-pyrrolo[2,3-c]pyridin-1-yl]-5-fluoro-N-methyl-N-(propan-2-yl)benzamide.

32. A pharmaceutical composition comprising the compound of claim 1 or a pharmaceutically acceptable salt thereof as an active ingredient, and a pharmaceutically acceptable additive agent.

33. A method for treating a tumor comprising administrating the compound of claim 1 or a pharmaceutically acceptable salt thereof to a patient in need thereof.

34. The method of claim 33, wherein the tumor is involved in Menin-MLL.

35. A pharmaceutical composition comprising the compound of claim 1 or a pharmaceutically acceptable salt thereof in combination with at least one different agent, wherein the different agent is at least one agent selected from the group consisting of an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, an biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

36. The method of claim 33 which comprises also administering at least one different agent, wherein the different agent is at least one agent selected from an antitumor alkylating agent, an antitumor antimetabolite, an antitumor antibiotic, a plant-derived antitumor medicament, an antitumor platinum complex compound, an antitumor camptothecin derivative, an antitumor tyrosine kinase inhibitor, an antitumor serine/threonine kinase inhibitor, an antitumor phospholipid kinase inhibitor, an antitumor monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

37. The compound or pharmaceutically acceptable salt thereof of claim 1, which is 5-fluoro-2-(3-{1-[(1S,3S,4R)-5-methylidene-2-azabicyclo[2.2.2]octane-3-carbonyl]piperidin-4-yl}-1H-pyrrolo[2,3-c]pyridin-1-yl)-N,N-di(propan-2-yl)benzamide or a pharmaceutically acceptable salt thereof.

38. The compound or pharmaceutically acceptable salt thereof of claim 1, which is 2-(3-{1-[(1S,3S,4R,6S)-6-(cyclopropylmethyl)-2-azabicyclo[2.2.2]octane-3-carbonyl]piperidin-4-yl}-1H-pyrrolo[2,3-c]pyridin-1-yl)-5-fluoro-N,N-di(propan-2-yl)benzamide or a pharmaceutically acceptable salt thereof.

39. The compound or pharmaceutically acceptable salt thereof of claim 1, which is 5-fluoro-N-methyl-2-(3-{1-[(1S,3S,4R)-5-methylidene-2-azabicyclo[2.2.1]heptane-3-carbonyl]azepan-4-yl}-1H-pyrrolo[2,3-c]pyridin-1-yl)-N-(propan-2-yl)benzamide or a pharmaceutically acceptable salt thereof.

40. The compound or pharmaceutically acceptable salt thereof of claim 1, which is 2-[3-({1-[(3S)-2-azabicyclo[2.2.2]octane-3-carbonyl]pyrrolidin-3-yl}methyl)-1H-pyrrolo[2,3-c]pyridin-1-yl]-5-fluoro-N-methyl-N-(propan-2-yl)benzamide or a pharmaceutically acceptable salt thereof.

* * * * *